(12) United States Patent
Hewitt et al.

(10) Patent No.: US 9,955,976 B2
(45) Date of Patent: May 1, 2018

(54) FILAMENTARY DEVICES FOR TREATMENT OF VASCULAR DEFECTS

(71) Applicant: SEQUENT MEDICAL, INC., Aliso Viejo, CA (US)

(72) Inventors: Todd J Hewitt, Laguna Niguel, CA (US); Brian Merritt, San Clemente, CA (US); William R Patterson, Huntington Beach, CA (US); James M Thompson, Lake Forest, CA (US); Claudio Plaza, Rancho Santa Margarita, CA (US); Hung P Tran, Westminster, CA (US)

(73) Assignee: Sequent Medical, Inc., Aliso Viejo, CA (US)

( * ) Notice: Subject to any disclaimer, the term of this patent is extended or adjusted under 35 U.S.C. 154(b) by 197 days.

(21) Appl. No.: 14/684,079

(22) Filed: Apr. 10, 2015

(65) Prior Publication Data

US 2016/0249934 A1 Sep. 1, 2016

Related U.S. Application Data

(63) Continuation-in-part of application No. 14/459,638, filed on Aug. 14, 2014, now Pat. No. 9,078,658.
(Continued)

(51) Int. Cl.
*A61M 29/00* (2006.01)
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12145* (2013.01);
(Continued)

(58) Field of Classification Search
CPC ........ A61B 17/12113; A61B 17/12172; A61B 2017/1205
See application file for complete search history.

(56) References Cited

U.S. PATENT DOCUMENTS

| | | |
|---|---|---|
| 3,874,388 A | 4/1975 | King et al. |
| 4,282,875 A | 8/1981 | Serbinenko |

(Continued)

FOREIGN PATENT DOCUMENTS

| | | |
|---|---|---|
| AU | 2009242528 | 3/2016 |
| CA | 2722037 | 10/2009 |

(Continued)

OTHER PUBLICATIONS

A Complete Microcatheter Portfolio; A Broad Selection of Microcatheters. Boston Scientific Brochure 2007.
(Continued)

*Primary Examiner* — Julian W Woo
(74) *Attorney, Agent, or Firm* — O'Melveny & Myers LLP

(57) ABSTRACT

Devices and methods for treatment of a patient's vasculature are described. The devices include implants made of woven braided mesh having a variable mesh density, i.e., the average size of pores in one region are a different than the average size of pores in another region. Additionally, there is a transition zone between the two regions. The implants have a low profile radially constrained state and an expanded state that is axially shortened. Methods of using the device to treat a cerebral aneurysm are also described. Methods of forming a tubular braid are also described. Methods of forming a tubular braid with variable braid densities are described. Methods of forming a tubular braid using a castellated mandrel are also described.

20 Claims, 56 Drawing Sheets

Related U.S. Application Data

(60) Provisional application No. 61/866,993, filed on Aug. 16, 2013, provisional application No. 62/093,313, filed on Dec. 17, 2014, provisional application No. 61/979,416, filed on Apr. 14, 2014.

(52) U.S. Cl.
CPC .. *A61B 17/12172* (2013.01); *A61B 17/12177* (2013.01); *A61B 17/12186* (2013.01); *A61B 2017/00292* (2013.01); *A61B 2017/00526* (2013.01); *A61B 2017/00778* (2013.01); *A61B 2017/00862* (2013.01); *A61B 2017/1205* (2013.01); *A61B 2017/12068* (2013.01)

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Molgaard-Nielsen |
| 4,675,361 A | 6/1987 | Ward |
| 4,729,278 A | 3/1988 | Graeff |
| 4,755,184 A * | 7/1988 | Silverberg ............... A61F 2/28 433/201.1 |
| 4,998,539 A | 3/1991 | Delsanti |
| 5,061,275 A | 10/1991 | Wallstén et al. |
| 5,071,407 A | 12/1991 | Termin et al. |
| 5,108,407 A | 4/1992 | Geremia et al. |
| 5,122,136 A | 6/1992 | Guglielmi et al. |
| 5,154,705 A | 10/1992 | Fleischhacker et al. |
| 5,158,545 A | 10/1992 | Trudell et al. |
| 5,165,421 A | 11/1992 | Fleischhacker et al. |
| 5,263,963 A | 11/1993 | Garrison |
| 5,334,210 A | 8/1994 | Gianturco |
| 378,239 A | 1/1995 | Terrnin |
| 5,536,247 A | 7/1996 | Thornton |
| 5,569,245 A | 10/1996 | Guglielmi et al. |
| 5,578,074 A | 11/1996 | Mirigian |
| 5,591,222 A | 1/1997 | Susawa et al. |
| 5,601,595 A | 2/1997 | Smith |
| 5,630,840 A | 5/1997 | Mayer |
| D380,266 S | 6/1997 | Boatman et al. |
| 5,645,559 A | 7/1997 | Hachtman et al. |
| 5,725,552 A | 3/1998 | Kotula |
| 5,725,570 A | 3/1998 | Heath |
| 5,733,294 A | 3/1998 | Forber |
| 5,749,883 A | 5/1998 | Halpern |
| 5,759,161 A | 6/1998 | Ogawa |
| 5,766,219 A | 6/1998 | Horton |
| 5,846,261 A | 12/1998 | Kotula et al. |
| 5,873,907 A | 2/1999 | Frantzen |
| 5,907,893 A | 6/1999 | Zadno-Azizi |
| 5,916,235 A | 7/1999 | Guglielmi |
| 5,925,060 A | 7/1999 | Forber |
| 5,927,345 A | 7/1999 | Samson |
| 5,928,260 A | 7/1999 | Chin et al. |
| 5,935,148 A | 8/1999 | Villar et al. |
| 5,944,733 A | 8/1999 | Engelson |
| 5,944,738 A | 8/1999 | Amplatz |
| 5,951,599 A | 9/1999 | McCrory |
| 5,964,797 A | 10/1999 | Ho |
| 5,980,554 A | 11/1999 | Lenker et al. |
| 5,984,929 A | 11/1999 | Bashiri et al. |
| 5,989,242 A | 11/1999 | Saadat et al. |
| 6,033,423 A | 3/2000 | Ken et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,123,715 A | 9/2000 | Amplatz |
| 6,139,564 A | 10/2000 | Teoh et al. |
| 6,142,975 A | 11/2000 | Jalisi et al. |
| 6,152,144 A | 11/2000 | Lesh et al. |
| 6,156,061 A | 12/2000 | Wallace et al. |
| 6,159,206 A | 12/2000 | Ogawa |
| 6,168,615 B1 | 1/2001 | Ken et al. |
| 6,168,618 B1 | 1/2001 | Frantzen |
| 6,168,622 B1 | 1/2001 | Mazzocchi |
| 6,190,402 B1 | 2/2001 | Horton et al. |
| 6,193,708 B1 | 2/2001 | Ken et al. |
| 6,203,779 B1 | 3/2001 | Ricci et al. |
| 6,221,086 B1 | 4/2001 | Forber |
| 6,277,126 B1 | 8/2001 | Barry et al. |
| 6,290,721 B1 | 9/2001 | Heath |
| 6,315,709 B1 | 11/2001 | Garibaldi et al. |
| 6,325,815 B1 | 12/2001 | Kusleika |
| 6,342,068 B1 | 1/2002 | Thompson |
| 6,344,048 B1 | 2/2002 | Chin et al. |
| 6,346,117 B1 | 2/2002 | Greenhalgh |
| 6,350,270 B1 | 2/2002 | Roue |
| 6,368,338 B1 | 4/2002 | Konya |
| 6,368,339 B1 | 4/2002 | Amplatz |
| 6,375,668 B1 | 4/2002 | Gifford et al. |
| 6,375,670 B1 | 4/2002 | Greenhalgh |
| 6,383,174 B1 | 5/2002 | Eder |
| 6,391,037 B1 | 5/2002 | Greenhalgh |
| 6,425,914 B1 | 7/2002 | Wallace et al. |
| 6,428,558 B1 | 8/2002 | Jones et al. |
| 6,447,531 B1 | 9/2002 | Amplatz |
| 6,454,780 B1 | 9/2002 | Wallace |
| 6,461,370 B1 | 10/2002 | Gray et al. |
| 6,463,317 B1 | 10/2002 | Kucharczyk |
| 6,468,266 B1 | 10/2002 | Bashiri et al. |
| 6,478,773 B1 | 11/2002 | Gandhi et al. |
| 6,500,149 B2 | 12/2002 | Gandhi et al. |
| 6,506,204 B2 | 1/2003 | Mazzocchi |
| 6,511,468 B1 | 1/2003 | Cragg et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,539 B1 | 8/2003 | Hayashi et al. |
| 6,613,074 B1 | 9/2003 | Mitelberg |
| 6,632,241 B1 | 10/2003 | Hancock |
| 6,635,068 B1 | 10/2003 | Dubrul et al. |
| 6,638,257 B2 | 10/2003 | Amplatz |
| 6,652,556 B1 | 11/2003 | Van Tassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,150 B1 | 2/2004 | Van Tassel |
| 6,689,486 B2 | 2/2004 | Ho et al. |
| 6,719,778 B1 | 4/2004 | Van Tassel et al. |
| 6,730,119 B1 | 5/2004 | Smalling |
| 6,743,236 B2 | 6/2004 | Barry et al. |
| 6,743,251 B1 | 6/2004 | Eder |
| 6,746,468 B1 | 6/2004 | Sepetka et al. |
| 6,746,890 B2 | 6/2004 | Gupta et al. |
| 6,752,826 B2 | 6/2004 | Holloway et al. |
| 6,780,196 B2 | 8/2004 | Chin et al. |
| 6,811,560 B2 | 11/2004 | Jones et al. |
| 6,855,153 B2 | 2/2005 | Saadt |
| 6,855,154 B2 | 2/2005 | Abdel-Gawwad |
| 6,878,384 B2 | 4/2005 | Cruise et al. |
| 6,936,055 B1 | 8/2005 | Ken et al. |
| 6,940,209 B2 | 9/2005 | Henderson |
| 6,953,472 B2 | 10/2005 | Palmer et al. |
| 6,953,473 B2 | 10/2005 | Porter |
| 6,966,892 B2 | 11/2005 | Gandhi et al. |
| 6,994,092 B2 | 2/2006 | van der Berg et al. |
| 7,001,409 B2 | 2/2006 | Amplatz |
| 7,004,962 B2 | 2/2006 | Stinson |
| 7,011,671 B2 | 3/2006 | Welch |
| 7,044,958 B2 | 5/2006 | Douk et al. |
| 7,052,513 B2 | 5/2006 | Thompson |
| 7,083,632 B2 | 8/2006 | Avellanet et al. |
| 7,101,390 B2 | 9/2006 | Nelson |
| 7,122,043 B2 | 10/2006 | Greenhalgh et al. |
| 7,128,736 B1 | 10/2006 | Abrams et al. |

(56) References Cited

U.S. PATENT DOCUMENTS

| | | | |
|---|---|---|---|
| 7,179,276 B2 | 2/2007 | Barry et al. | |
| 7,182,774 B2 | 2/2007 | Barry et al. | |
| 7,195,636 B2 | 3/2007 | Avellanet et al. | |
| 7,198,613 B2 | 4/2007 | Gandhi et al. | |
| 7,201,918 B2 | 4/2007 | Cruise | |
| 7,229,454 B2 | 6/2007 | Tran | |
| 7,229,461 B2 | 7/2007 | Chin et al. | |
| 7,275,471 B2 | 10/2007 | Nishri et al. | |
| 7,326,225 B2 | 2/2008 | Ferrera et al. | |
| 7,329,279 B2 | 2/2008 | Haug et al. | |
| 7,331,980 B2 | 2/2008 | Dubrul | |
| 7,410,482 B2 | 8/2008 | Murphy | |
| 7,419,503 B2 | 9/2008 | Pulnev et al. | |
| 7,490,396 B2 | 2/2009 | Bradley | |
| 7,524,319 B2 | 4/2009 | Dubrul | |
| 7,569,066 B2 | 8/2009 | Gerberding | |
| 7,573,382 B2 | 8/2009 | Choubey et al. | |
| 7,575,582 B2 | 8/2009 | Gandhi et al. | |
| 7,578,826 B2 | 8/2009 | Gandhi et al. | |
| 7,597,704 B2 | 10/2009 | Frazier et al. | |
| 7,648,532 B2 | 1/2010 | Greenhalgh et al. | |
| 7,695,488 B2 | 4/2010 | Berenstein | |
| 7,722,637 B2 | 5/2010 | Barry et al. | |
| 7,745,732 B2 | 6/2010 | Michael et al. | |
| 7,806,919 B2 | 10/2010 | Bloom et al. | |
| 7,862,577 B2 | 1/2011 | Gray et al. | |
| 7,942,925 B2 | 5/2011 | Yodfat | |
| 7,989,703 B2 | 8/2011 | Schaffer | |
| 8,043,326 B2 * | 10/2011 | Hancock | A61B 17/12022 606/200 |
| 8,043,329 B2 | 10/2011 | Khairkhahan | |
| 8,066,757 B2 | 11/2011 | Ferrera et al. | |
| 8,142,456 B2 | 3/2012 | Rosqueta et al. | |
| 8,182,506 B2 | 5/2012 | Fitz et al. | |
| 8,192,480 B2 | 6/2012 | Tieu et al. | |
| 8,313,505 B2 | 11/2012 | Amplatz et al. | |
| 8,398,670 B2 | 3/2013 | Amplatz | |
| 8,430,012 B1 | 4/2013 | Marchand | |
| 8,506,619 B2 | 8/2013 | Ortiz et al. | |
| 8,551,132 B2 | 10/2013 | Eskridge et al. | |
| 8,597,320 B2 | 12/2013 | Sepetka et al. | |
| 8,597,323 B1 | 12/2013 | Plaza et al. | |
| 8,690,907 B1 | 4/2014 | Janardhan | |
| 8,715,338 B2 | 5/2014 | Frid | |
| 8,728,117 B1 | 5/2014 | Janardhan et al. | |
| 8,758,395 B2 * | 6/2014 | Kleshinski | A61B 17/0057 606/151 |
| 8,840,735 B2 | 9/2014 | Schaffer | |
| 8,845,679 B1 | 9/2014 | Janardhan et al. | |
| 9,078,658 B2 | 7/2015 | Hewitt et al. | |
| 9,179,918 B2 | 11/2015 | Levy et al. | |
| 9,198,668 B2 | 12/2015 | Theobald et al. | |
| 9,198,670 B2 | 12/2015 | Hewitt et al. | |
| 9,242,070 B2 | 1/2016 | Tieu | |
| 9,259,337 B2 | 2/2016 | Cox et al. | |
| 9,272,323 B2 | 3/2016 | Schaffer | |
| 9,295,473 B2 | 3/2016 | Hewitt et al. | |
| 9,492,174 B2 | 11/2016 | Hewitt et al. | |
| 9,504,588 B2 | 11/2016 | Sadisivan et al. | |
| 9,687,245 B2 | 6/2017 | Molaei et al. | |
| 9,855,047 B2 * | 1/2018 | Berez | A61B 17/12109 |
| 2001/0031981 A1 | 10/2001 | Evans et al. | |
| 2002/0065552 A1 | 5/2002 | Jayaraman et al. | |
| 2002/0103542 A1 | 8/2002 | Bilbo | |
| 2002/0143349 A1 | 10/2002 | Gifford, III et al. | |
| 2002/0143361 A1 | 10/2002 | Douk et al. | |
| 2002/0156499 A1 | 10/2002 | Konya et al. | |
| 2002/0169473 A1 | 11/2002 | Sepetka et al. | |
| 2002/0183787 A1 | 12/2002 | Wahr et al. | |
| 2002/0187288 A1 | 12/2002 | Lim et al. | |
| 2003/0012816 A1 | 1/2003 | West et al. | |
| 2003/0028209 A1 | 2/2003 | Teoh et al. | |
| 2003/0171739 A1 | 9/2003 | Murphy et al. | |
| 2003/0171774 A1 | 9/2003 | Freudenthal et al. | |
| 2003/0181942 A1 | 9/2003 | Sutton et al. | |
| 2003/0187473 A1 | 10/2003 | Berenstein et al. |
| 2003/0199913 A1 | 10/2003 | Dubrul et al. |
| 2004/0059370 A1 | 3/2004 | Greene et al. |
| 2004/0098027 A1 | 5/2004 | Teoh et al. |
| 2004/0111147 A1 | 6/2004 | Rabkin et al. |
| 2004/0122367 A1 | 6/2004 | Van Tassel et al. |
| 2004/0143239 A1 | 7/2004 | Zhou et al. |
| 2004/0158311 A1 | 8/2004 | Berhow |
| 2004/0172053 A1 | 9/2004 | Barry et al. |
| 2004/0186562 A1 | 9/2004 | Cox |
| 2004/0193206 A1 | 9/2004 | Gerberding et al. |
| 2004/0193208 A1 | 9/2004 | Talpade et al. |
| 2004/0220563 A1 | 11/2004 | Eder |
| 2004/0260333 A1 | 12/2004 | Dubrul et al. |
| 2005/0021075 A1 | 1/2005 | Bonnette et al. |
| 2005/0033408 A1 | 2/2005 | Jones et al. |
| 2005/0053782 A1 | 3/2005 | Sen et al. |
| 2005/0096728 A1 | 5/2005 | Ramer |
| 2005/0112349 A1 | 5/2005 | Laurencin et al. |
| 2005/0113868 A1 | 5/2005 | Devellian et al. |
| 2005/0119684 A1 | 6/2005 | Guterman et al. |
| 2005/0133046 A1 | 6/2005 | Becker et al. |
| 2005/0149173 A1 | 7/2005 | Hunter et al. |
| 2005/0216052 A1 | 9/2005 | Mazzocchi et al. |
| 2005/0222489 A1 | 10/2005 | Rahdert et al. |
| 2005/0228422 A1 | 10/2005 | Machold et al. |
| 2005/0228434 A1 | 10/2005 | Amplatz et al. |
| 2005/0267516 A1 | 12/2005 | Soleimani et al. |
| 2005/0277978 A1 | 12/2005 | Greenhalgh |
| 2006/0009798 A1 | 1/2006 | Callister et al. |
| 2006/0009799 A1 | 1/2006 | Kleshinski et al. |
| 2006/0009800 A1 | 1/2006 | Christianson et al. |
| 2006/0052815 A1 | 3/2006 | Fitz et al. |
| 2006/0052816 A1 | 3/2006 | Bates et al. |
| 2006/0064151 A1 | 3/2006 | Guterman et al. |
| 2006/0083721 A1 | 4/2006 | Cohen et al. |
| 2006/0116708 A1 | 6/2006 | Ogawa et al. |
| 2006/0135947 A1 | 6/2006 | Soltesz et al. |
| 2006/0155323 A1 | 7/2006 | Porter et al. |
| 2006/0178694 A1 | 8/2006 | Greenhalgh et al. |
| 2006/0200192 A1 | 9/2006 | Fitz et al. |
| 2006/0200234 A1 | 9/2006 | Hines |
| 2006/0212055 A1 | 9/2006 | Karabey et al. |
| 2006/0217799 A1 | 9/2006 | Mailander et al. |
| 2006/0235464 A1 | 10/2006 | Avellanet et al. |
| 2006/0247680 A1 | 11/2006 | Amplatz et al. |
| 2006/0252984 A1 | 11/2006 | Rahdert et al. |
| 2006/0253149 A1 | 11/2006 | Gandhi et al. |
| 2006/0271086 A1 | 11/2006 | Ramzipoor et al. |
| 2007/0021816 A1 | 1/2007 | Rudin |
| 2007/0031584 A1 | 2/2007 | Roth |
| 2007/0061006 A1 | 3/2007 | Desatnik et al. |
| 2007/0088387 A1 | 4/2007 | Eskridge et al. |
| 2007/0100419 A1 | 5/2007 | Licata et al. |
| 2007/0106323 A1 | 5/2007 | Barry et al. |
| 2007/0112380 A1 | 5/2007 | Figulla |
| 2007/0142906 A1 | 6/2007 | Figulla |
| 2007/0144124 A1 | 6/2007 | Schewe et al. |
| 2007/0167911 A1 | 7/2007 | Gandhi et al. |
| 2007/0167980 A1 | 7/2007 | Figulla et al. |
| 2007/0173928 A1 | 7/2007 | Morsi |
| 2007/0203062 A1 | 8/2007 | Ellis-Behnke et al. |
| 2007/0208373 A1 | 9/2007 | Zaver et al. |
| 2007/0208376 A1 | 9/2007 | Meng |
| 2007/0225760 A1 | 9/2007 | Moszner |
| 2007/0233186 A1 | 10/2007 | Meng |
| 2007/0255388 A1 | 11/2007 | Rudakov et al. |
| 2007/0265656 A1 | 11/2007 | Amplatz et al. |
| 2007/0288083 A1 | 12/2007 | Hines |
| 2008/0033341 A1 | 2/2008 | Grad |
| 2008/0033366 A1 | 2/2008 | Matson et al. |
| 2008/0033475 A1 | 2/2008 | Meng |
| 2008/0033478 A1 | 2/2008 | Meng |
| 2008/0119886 A1 | 5/2008 | Greenhalgh et al. |
| 2008/0195139 A1 | 8/2008 | Donald et al. |
| 2008/0200945 A1 | 8/2008 | Amplatz et al. |
| 2008/0221600 A1 | 9/2008 | Deck et al. |
| 2008/0228215 A1 | 9/2008 | Strauss et al. |
| 2009/0025820 A1 | 1/2009 | Adams |

(56) References Cited

U.S. PATENT DOCUMENTS

| | | |
|---|---|---|
| 2009/0062812 A1 | 3/2009 | Fitz et al. |
| 2009/0062834 A1 | 3/2009 | Moftakhar |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112305 A1 | 4/2009 | Goldmann et al. |
| 2009/0132024 A1 | 5/2009 | Berkhoff |
| 2009/0163780 A1 | 6/2009 | Tieu |
| 2009/0227976 A1 | 9/2009 | Calabria |
| 2009/0275974 A1 | 11/2009 | Marchand |
| 2009/0287291 A1 | 11/2009 | Becking et al. |
| 2009/0287294 A1 | 11/2009 | Rosqueta et al. |
| 2009/0318948 A1 | 12/2009 | Linder et al. |
| 2010/0023048 A1 | 1/2010 | Mach |
| 2010/0023105 A1 | 1/2010 | Levy et al. |
| 2010/0069948 A1 | 3/2010 | Veznedaroglu |
| 2010/0094409 A1 | 4/2010 | Barker et al. |
| 2010/0106235 A1 | 4/2010 | Kariniemi et al. |
| 2011/0022149 A1 | 1/2011 | Cox |
| 2011/0029008 A1 | 2/2011 | Gesswein |
| 2011/0046658 A1 | 2/2011 | Connor et al. |
| 2011/0046719 A1 | 2/2011 | Frid |
| 2011/0054515 A1 | 3/2011 | Bridgeman |
| 2011/0082493 A1 | 4/2011 | Samson et al. |
| 2011/0152823 A1 | 6/2011 | Mohiuddin |
| 2011/0152993 A1 | 6/2011 | Marchand |
| 2011/0202085 A1 | 8/2011 | Loganathan et al. |
| 2011/0208227 A1 | 8/2011 | Becking |
| 2011/0208233 A1 | 8/2011 | McGuckin |
| 2011/0224776 A1 | 9/2011 | Sepetka et al. |
| 2011/0295298 A1 | 12/2011 | Moszner |
| 2011/0319926 A1 | 12/2011 | Becking |
| 2012/0143237 A1 | 6/2012 | Cam |
| 2012/0165919 A1 | 6/2012 | Cox |
| 2012/0197283 A1 | 8/2012 | Marchand et al. |
| 2012/0271337 A1 | 10/2012 | Figulla et al. |
| 2012/0283768 A1 | 11/2012 | Cox |
| 2012/0296362 A1 | 11/2012 | Cam |
| 2013/0066357 A1 | 3/2013 | Aboytes et al. |
| 2013/0116722 A1 | 5/2013 | Aboytes et al. |
| 2013/0123830 A1 | 5/2013 | Becking et al. |
| 2013/0211495 A1 | 8/2013 | Halden et al. |
| 2013/0245667 A1 | 9/2013 | Marchand et al. |
| 2013/0253572 A1 | 9/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2014/0005713 A1 | 1/2014 | Bowman |
| 2014/0005714 A1* | 1/2014 | Quick .................. A61L 31/022 606/200 |
| 2014/0018841 A1 | 1/2014 | Peiffer et al. |
| 2014/0052233 A1 | 2/2014 | Cox et al. |
| 2014/0074151 A1 | 3/2014 | Tischler et al. |
| 2014/0135734 A1 | 5/2014 | Dakin et al. |
| 2014/0135817 A1 | 5/2014 | Tischler et al. |
| 2015/0182674 A1 | 7/2015 | Schaffer |
| 2016/0030052 A1 | 2/2016 | Cragg et al. |
| 2016/0192941 A1 | 7/2016 | Hewitt et al. |
| 2016/0262769 A1 | 9/2016 | Cragg et al. |
| 2016/0324528 A1 | 11/2016 | Hebert et al. |
| 2016/0335757 A1 | 11/2016 | Florent et al. |
| 2017/0245862 A1 | 8/2017 | Cox et al. |

FOREIGN PATENT DOCUMENTS

| | | |
|---|---|---|
| CN | 106974691 | 7/2017 |
| EP | 0706876 | 7/2000 |
| EP | 1400219 | 3/2004 |
| EP | 0808138 | 5/2005 |
| EP | 1576929 | 9/2005 |
| EP | 1844717 | 10/2007 |
| EP | 1923019 | 5/2008 |
| EP | 2055263 | 6/2009 |
| EP | 2258275 | 12/2011 |
| EP | 2157937 | 3/2017 |
| JP | 52141092 | 11/1977 |
| JP | H4-47415 | 4/1992 |
| JP | 6124952 | 4/2017 |
| WO | WO 1996/01591 | 1/1996 |
| WO | WO 1997/26939 | 7/1997 |
| WO | WO 1999/03404 | 1/1999 |
| WO | WO 1999/05977 | 2/1999 |
| WO | WO 1999/62432 | 12/1999 |
| WO | WO 2002/00139 | 6/2000 |
| WO | WO 2001/45571 | 6/2001 |
| WO | WO 2001/93782 | 12/2001 |
| WO | WO 2003/011151 | 2/2003 |
| WO | WO 2003/032818 | 4/2003 |
| WO | WO 2003/063732 | 8/2003 |
| WO | WO 2004/047649 | 6/2004 |
| WO | WO 2004/093742 | 11/2004 |
| WO | WO 2005/117718 | 12/2005 |
| WO | WO 2006/026744 | 3/2006 |
| WO | WO 2006/055683 | 5/2006 |
| WO | WO 2007/096183 | 8/2007 |
| WO | WO 2008/151204 | 12/2008 |
| WO | WO 2009/121006 | 1/2009 |
| WO | WO 2009/036219 | 3/2009 |
| WO | WO 2009/126747 | 10/2009 |
| WO | WO 2009/132045 | 10/2009 |
| WO | WO 2009/134337 | 11/2009 |
| WO | WO 2009/135166 | 11/2009 |
| WO | WO 2010/134914 | 11/2010 |
| WO | WO 2011/057002 | 5/2011 |
| WO | WO 2013/159065 | 10/2013 |
| WO | WO 2014/087245 | 6/2014 |
| WO | WO 2014/169261 | 10/2014 |
| WO | WO 2015/171268 | 11/2015 |
| WO | WO 2015/192019 | 12/2015 |
| WO | WO 2017/156275 | 9/2017 |

OTHER PUBLICATIONS

Allen et al., "Mioromachine Wedge Stepping Motor," pp. 1-6, Nov. 12-20, 1998 ASME International Mechanical Engineering Congress, Anaheim, CA.

Altes et al., "Creation of Saccular Aneurysms in the Rabbit: A model Suitable for Testing Endovascular Devices," American Roentgen Ray Society, Feb. 2000.

Ansari et al., "Thrombosis of a Fusiform Intracranial Aneurysm Induced by Overlapping Neuroform Stents: Case Report," *Neurosurgery*, E950-E951 vol. 60, No. 5, May 2007.

Atritech Press Release, Minneapolis, Jun. 18, 2007 "Atritech Announces Intellectual Property Acquisition, Transaction Establishes Company as leader in Left Atrial Appendage Market".

Caroff, J. et al., "Role of C-Arrn VasoCT in the Use of Endovascular WEB Flow Disruption in Intracranial Aneurysm Treatment," *AJNR Am. J. Neuroradiol.* 35(7):1353-1357 (Jul. 2014).

Caroof, J. et al., "Woven Endobridge (WEB) Device for endovascular treatment of ruptured intracranial wide-neck aneurysms: a single-center experience," *Neuroradiology*, 56(9):755-761 (Sep. 2014).

Colla, R. et al, "Treatment of Wide-Neck Basilar Tip Aneurysms Using the Web II Device," *The Neuroradiology Journal* 26(6):669-677 (Dec. 2013).

De Backer, O. et al., "Percutaneous left atrial appendage occlusion for stroke prevention in atrial fibrillation: an update," *Open Heart*, 4:1-14 (2013).

Ding, Y.H. et al., "The Woven EndoBridge: A New Aneurysm Occlusion Device," *AJNR Am. J. Neruradiol.* 32:607-611 (Mar. 2011).

Duerig, T.W., "The Use of Superelasticity in Modern Medicine" MRS Bulletin, pp. 101-104 (Feb. 2002).

Fiorella, D. et al., "Interobserver variability in the assessment of aneurysm occlusion with the WEB aneurysm embolization system," *J. NeuroIntervent. Surg.* Jul. 1, 2014, pii: neurintsurg-2014-011251. doi: 10.1136/neurintsurg-2014-011251 [Epub ahead of print].

(56) References Cited

OTHER PUBLICATIONS

Fort Wayne Metals HHS Tube brochure, p. 28-29 (2009), Fort Wayne, Indiana, www.oldsite.fwmetals.com.
Grabenwoger et al., "Endothelialization of Biosynthetic vascular Prosthesis After Laser Perforation," *Ann Thorac Surg*, 1998;66:S110-S114.
Guider Softip XF Guide Catheters Brochure, Boston Scientific Corporation 2004.
Gupta et al., "Nitinol Thin Film Three Dimensional Devices—Fabrication and Applications," From: SMST-2003: Proceedings of the International Conference on Shape Memory and Superelastic Technologies Published: 2004.
Hill et al., "Initial Results of the AMPLATZER® Vascular Plug in the treatment of Congenital Heart Disease," Technology and Services, *Business Briefing: US Cardiology*, pp. 1-3 (2004).
Jeffree et al., "The Porus, Guidewire-Directed, Detachable Aneurysm Liner: A New Concept in the Endovascular Treatment of Intracranial Aneurysms," *AJNR Am J Neuradiol* 20:774-779, May 1999.
Kallmes et al., "A New Endoluminal, Flow-Disrupting Device for Treatment of Saccular Eneurysms," *Stroke, Journal of the American Heart Association* 2007; 38;1-7.
Klisch, J. et al., "The Woven EndoBridge Cerebral Aneurysm Embolization Device (WEB II): initial clinical experience," *Neuroradiology* 53:599-607 (2011).
Kónya, A. and Wright, K.C., "Preliminary Results with a New Vascular Basket Occluder in Swine," *JVIR*, 10(8):1043-1049 (1999).
Kwon et al., "Preliminary Results of the Luna Aneurysm Embolization System in a Rabbit Model: A New Intrasaccular Aneurysm Occlusion Device," *AJNR Am J Neuroradiol*, 32:602-606 (Mar. 2011).
Lendlein, A. and Kelch, S., "Shape—Memory Polymers," *Angew. Chem. Int. Ed.*, 41:2034-2057 (2002).
Lendlein, A. and Langer, R., "Biodegradable, Elastic Shape—Memory Polymers for Potential Biomedical Applications," *Science* 296:1673-1676 (May 31, 2002).
Lieber, B.B. et al., "The Role of Blood Impulse in Cerebral Aneurysm Coil Compaction: Effect of Aneurysm Neck Size," IMECE2003-13099, *Proceedings of IMECE'03*, 2003 ASME international Mechanical Engineering Congress, Washington, D.C. (Nov. 15-21, 2003).
Liu, C. et al., "Review of progress in shape—memory polymers," *J. Mater. Chem.* 17:1543-1558 (2007).
Lubicz, B. et al., "WEB Device for Endovascular Treatment of Wide-Neck Bifurcation Aneurysms," *AJNR Am. J. Neuroradiol.* 34(6):1209-1214 (Jun.-Jul. 2013).
Lubicz, B. et al., "WEB—DL Endovascular Treatment of Wide-Neck Bifurcation Aneurysms: Short- and Midterm Results in a European Study," *AJNR Am. J. Neuroradiol.* 35(3):432-438 (Mar. 2014). doi: 10.3174/ajnr.A3869. Epub Jan. 23, 2014.
Major, S. and Hubalovsky, S., "Life of Nitinol Drawn Filed Wires with Ag or Au Core for Medical Application," *International Journal of Mechanics* 2(7):73-80 (2013).
Matinlinna et al., "An Introduction to Silanes and Their Clinical Applications in Dentistry," *The International Journal of Prosthodontics*, 17(2):155-164 (2004).
Mine et al., "Intrasaccular flow-diversion for treatment of intracranial aneurysms: the Woven EndoBridge," *Expert Rev. Med. Devices* 11(3): 315-325 (May 2014). doi: 10.1586/1743440.2014.907741. Epub Apr. 2, 2014.
Nakayama et al., "Development of Microporous Covered Stents: Geometrical Design of the Luminal Surface," *The International Journal of Artificial Organs*, 28(6):600-608 (2005).
Nemat-Nasser, S. and Guo, W.-G., "Superelastic and cyclic response of NiTi SMA at various strain rates and temperatures," *Mechanics of Materials* 38:463-474 (2006).
Nishi et al., "Embolization of experimental aneurysms using a heparin-loaded stent graft with micropores," *Cardiovascular Radiation Medicine* 4:29-33 (2003).

Nishi et al., "Occlusion of Experimental Aneurysms with Heparin-Loaded, Microporous Stent Grafts," *Neurosurgery*, 53(6):1397-1405 (Dec. 2003).
Papagiannaki, C. et al., "WEB Intrasaccular Flow Disruptor—Prospective, Multicenter Experience in 83 Patients with 85 Aneurysms," *AJNR Am. J. Neuroradiol.* 35(11):2106-2111 (Nov.-Dec. 2014). 35(11):2106-11. doi: 10.3174/ajnr.A4028. Epub Jul. 3, 2014.
Park, J. et al., "Percutaneous Left Atrial Appendage Transcatheter Occlusion (PLAATO) for Stroke Prevention in Atrial Fibrillation: 2-Year Outcome," *J Invasive Cardiol* 21:446-450 (2009).
Pelton, A.R. et al., "Optimisation of processing and properties of medical grade Nitinol wire," *Min. Invas. Ther. & Allied Technol.* 9(1):107-118 (2000).
Pham, Q. et al., "Electrospinning of Polymeric Nanofibers for Tissue Engineering Applications: A Review, *Tissue Engr.*, 12(5):1197-1211 (2006).
Pierot, L. et al, "WEB Treatment of Intracranial Aneurysms: Feasibility, Complications, and 1-Month Safety Results with the WEB DL and WEB SL/SLS in the French Observatory," *AJNR Am J Neuroradiol* . Feb. 5, 2015 [Epub ehead ofprint].
Pierot, L. et al., "Endovascular WEB Flow Disruption in Middle Cerebral Artery Aneurysms: Preliminary Feasibility, Clinical, and Anatomical Results in a Multicenter Study," *Neurosurgery* 73(1):27-35 (Jul. 2013).
Pierot, L. et al., "Intrasaccular Flow-Disruption Treatment of Intracranial Aneurysms: Preliminary Results of a Multicenter Clinical Study," *AJNR Am J Neuroradiol*. 33(7):1232-1238 (Aug. 2012). doi: 10.3174/ajnr.A3191. Epub Jun. 7, 2012.
Pierot, L. et al., "Role, safety, and efficacy of WEB flow disruption: a review," *EJMINT* Invited Review, 2014: 1419000139 (May 8, 2014).
Romero, J. et al., "Left Atrial Appendage Closure Devices," *Clinical Medicine Insights: Cardiology*, 8:45-52 (2014).
Rottiers, W. et al., "Shape Memory Materials and their applications," In Korolev's readings: conference proceedings, pp. 250-251 (2011).
Salamat et al., "Experimental Evaluation of a New Transcatheter Vascular Embolization Device in the Swine Model," *J Vasc Interv Radiol.*, 12:301-311 (2002).
Schaffer, J.E. and Gordon, R., "Engineering Characteristics of Drawn Filled Nitinol Tube," *SMST-2003: Proceedings of the International Conference on Shape Memory and Superelastic Technologies (ASM International)*, p. 109-118 (2004).
Schmitz-Rode, T. et al., "Self-expandable spindle for transcatheter vascular occlusion: in vivo experiments. Work in progress." *Radiology* 188:95-100 (Jul. 1993).
Simgen, A. et al., "Evaluation of a newly designed flow diverter for the treatment of intracranial aneurysms in an elastase-induced aneurysm model, in New Zealand white rabbits," *Neuroradiology* 56:129-137 (2014).
Spelle, L. and Liebig, T., "Letter to the Editor," *Neuroradiol J.* Jun. 2014; 27(3):369. doi: 10.15274/NRJ-2014-10048. Epub Jun. 17, 2014.
Stoeckel, D. et al., "Self-expanding nitinol stents: material and design considerations," *Eur. Radiol.* 14:292-301 (2004).
Turk, A. et al., "Evaluation of the TriSpan Neck Bridge Device for the Treatment of Wide-Necked Aneurysms: An Experimental Study in Canines, Editorial Comment: An Experimental Study in Canines," *Stroke* 32:492-497 (Feb. 2001).
Wallner, A.K. et al., "Coiling after Treatment with the Woven EndoBridge Cerebral Aneurysm Embolization Device," *Interventional Neuroradiology* 18:208-212 (2012).
Yeow, W.L. and Kar, S., "Device- and LAA-Specific Characteristics for Successful LAA Closures: Tips and Tricks," *Intervent. Cardiol. Clin.*, 3:239-254 (2014).
Zimmermann et al., "Patent Foramen Oval Closure With the SeptRx Device, Initial Experience with the First "In-Tunnel" Device," *J Am Coll Cardiol Intv*, 3(9):963-967 (2010).
International Preliminary Report on Patentability dated Dec. 7, 2009 for International Application No. PCT/US2008/065694 filed on Jun. 3, 2008 and published as: WO/2008/151204 on Dec. 11, 2008.

(56) References Cited

OTHER PUBLICATIONS

International Search Report and Written Opinion dated Oct. 31, 2008 for International Application No. PCT/US2008/065694 filed on Jun. 3, 2008.
International Preliminary Report on Patentability dated Nov. 2, 2010 for International Application No. PCT/US2009/042592 filed on May 1, 2009 and published as: WO/2009/135166 on Nov. 5, 2009.
International Search Report and Written Opinion dated Nov. 26, 2009 for International Application No. PCT/US2009/042592 filed on May 1, 2009.
International Search Report and Written Opinion dated Jul. 28, 2011 for International Application No. PCT/US2010/055494 filed on Nov. 4, 2010 and published as WO/2011/057002 on May 12, 2011.
Extended European Search Report dated Apr. 24, 2014, in EP Appl No. EP 08770070 filed Jun. 3, 2008.
Extended European Search Report dated Jul. 30, 2014, in EP Appl No. EP 10829110 filed Nov. 4, 2010.
International Search Report dated Jul. 21, 2015, for International Application No. PCT/US2015/025609.
International Search Report dated Jan. 11, 2016, for International Application No. PCT/US2015/025613.
Extended European Search Report dated Dec. 13, 2017, in EP Appl No. EP 15789225 filed Nov. 7, 2016.

\* cited by examiner

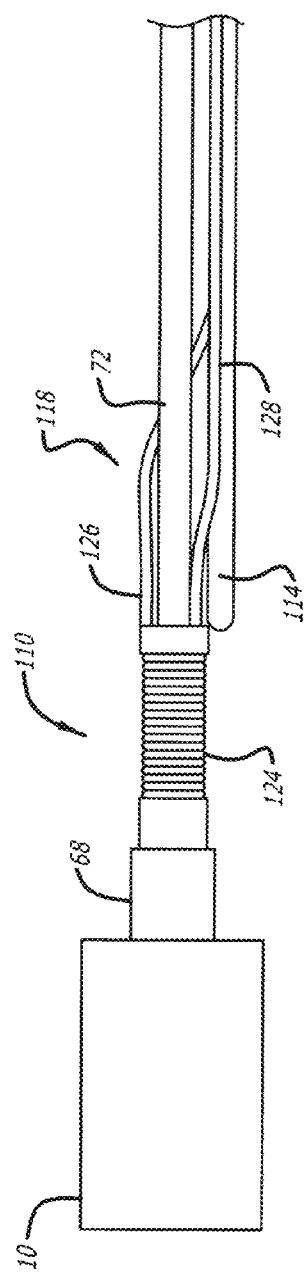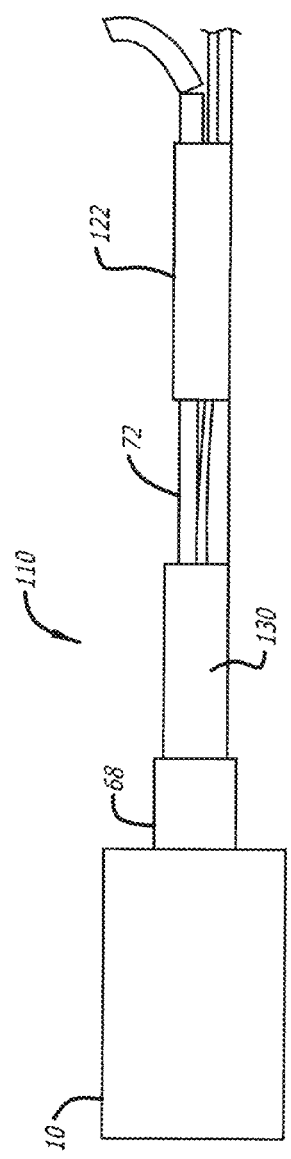

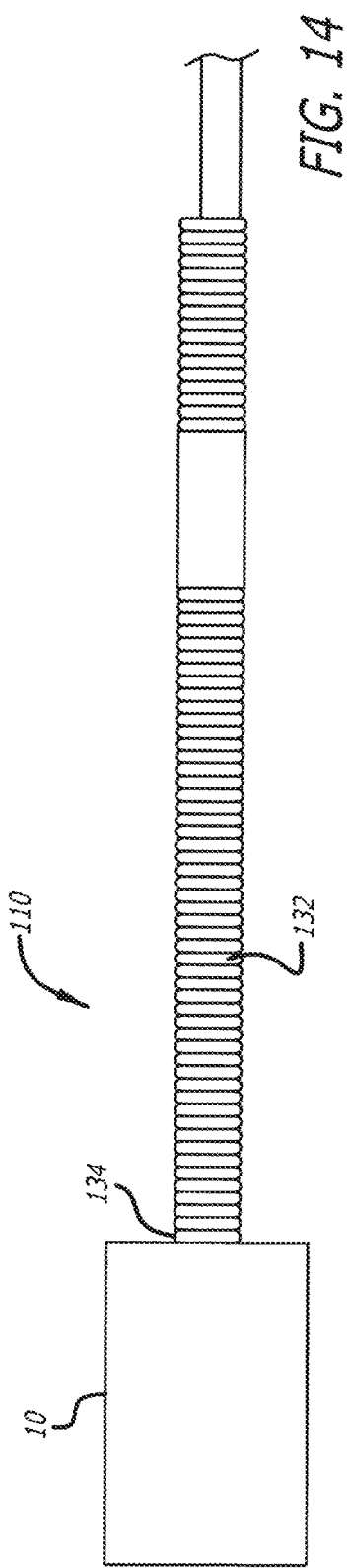
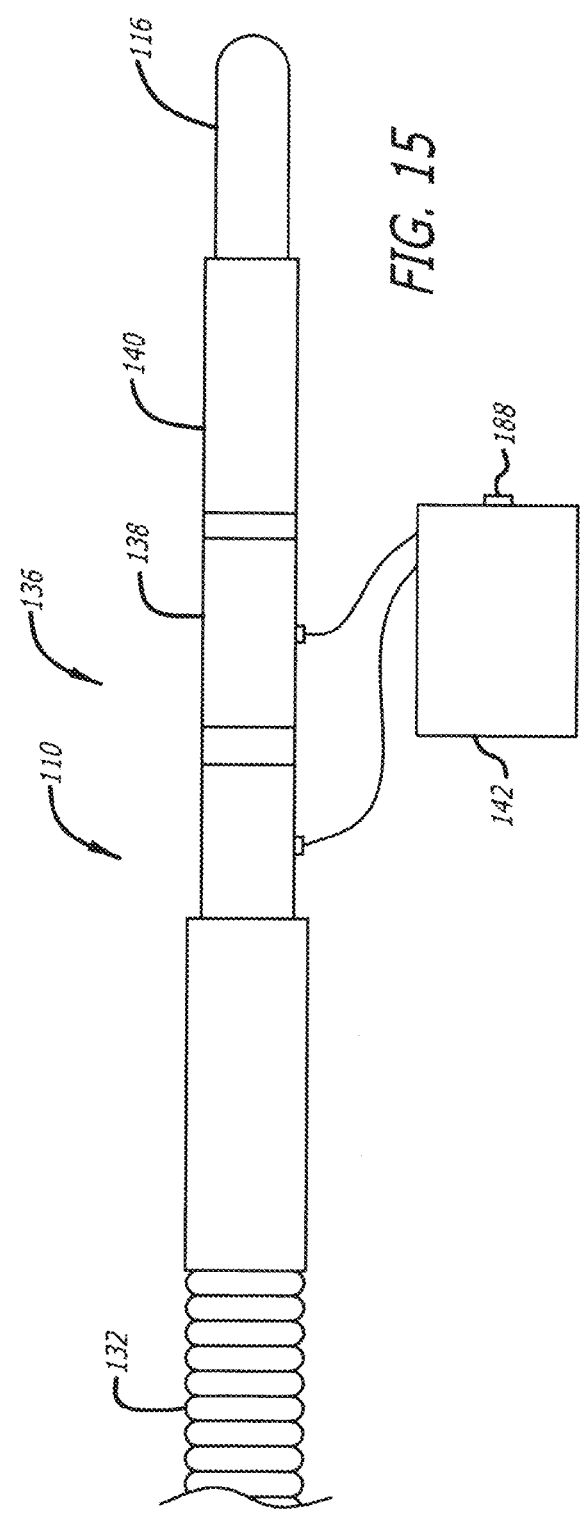

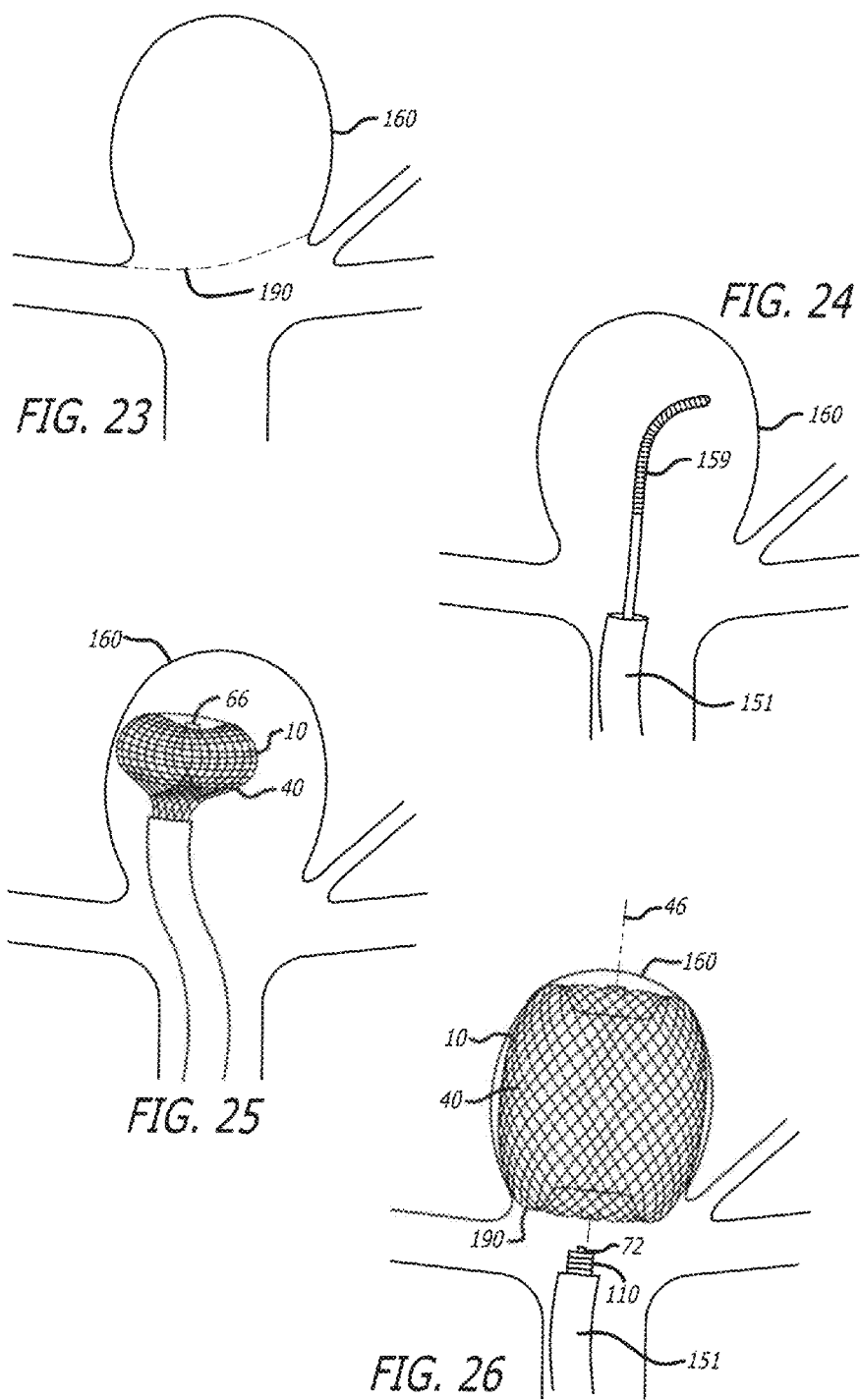

FIG. 46
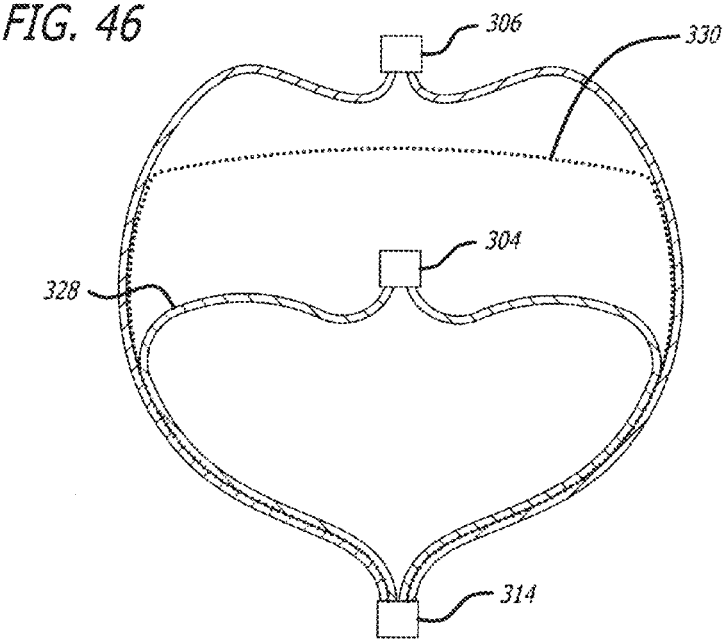
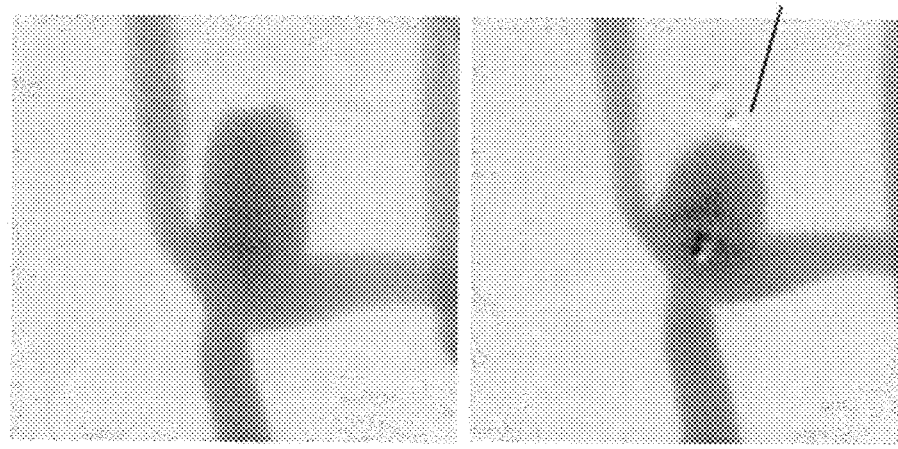
Pre-treatment Angiogram
FIG. 47
10 minutes Post treatment
FIG. 48

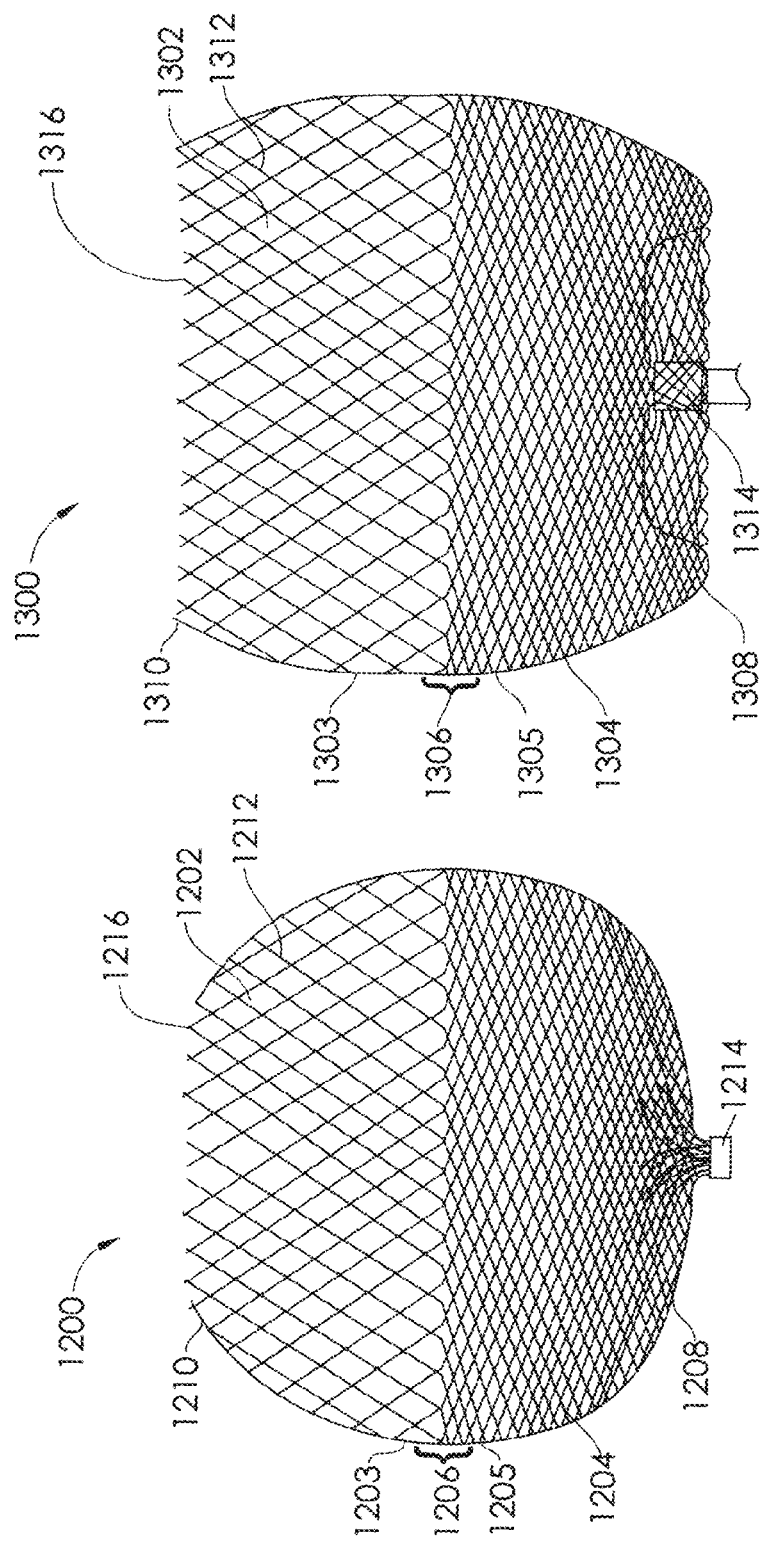

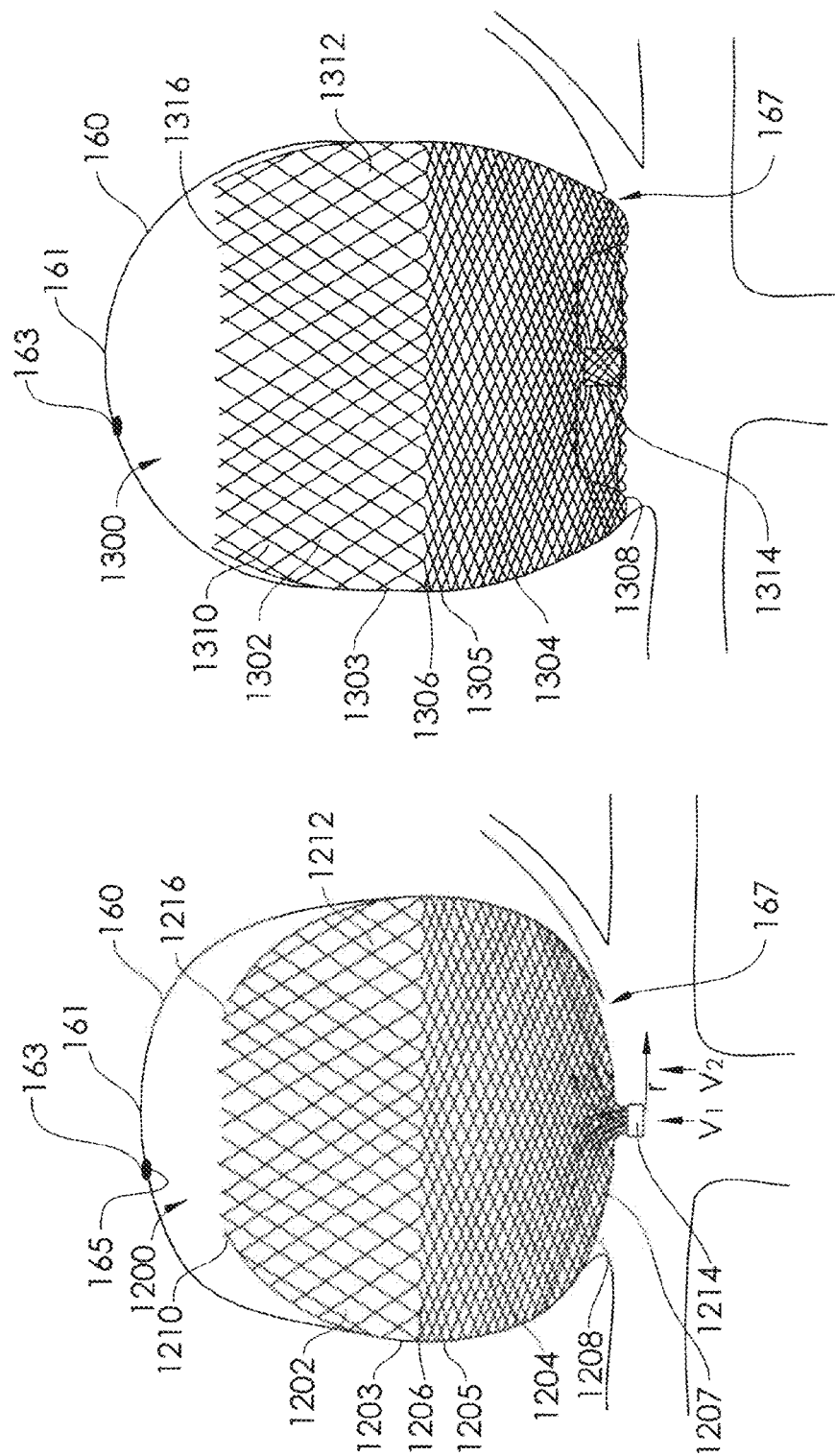

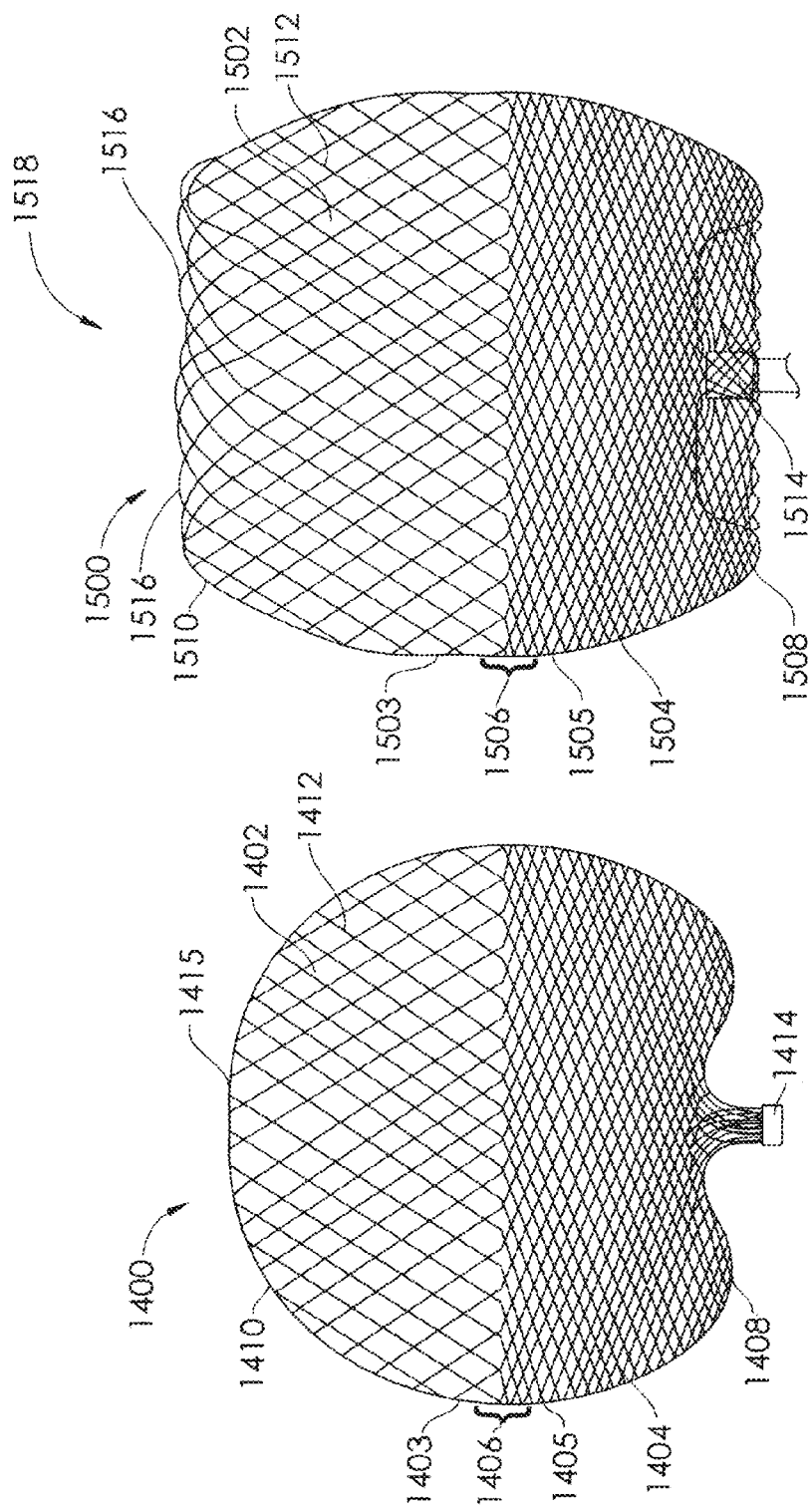

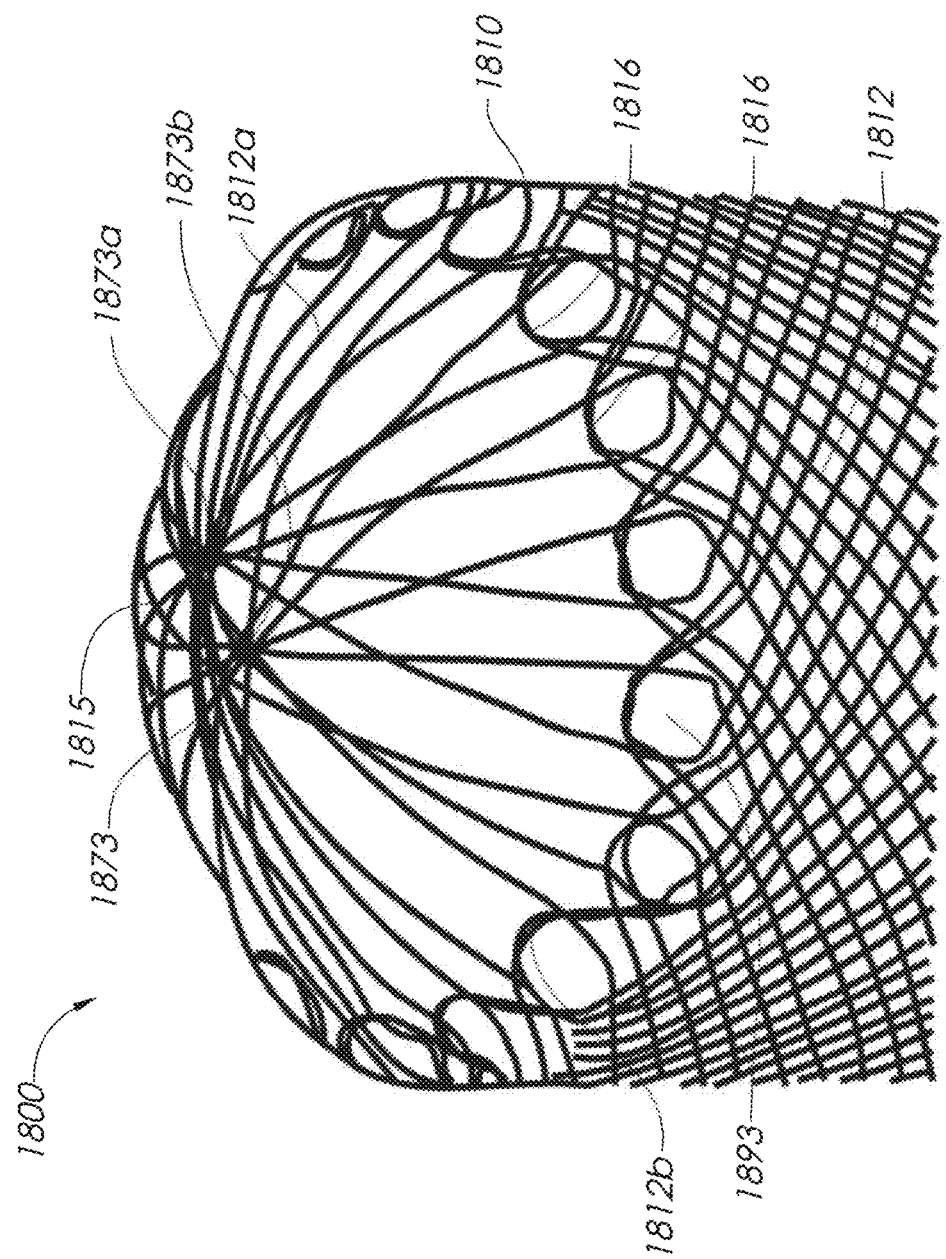

FILAMENTARY DEVICES FOR TREATMENT OF VASCULAR DEFECTS

RELATED APPLICATIONS

This application claims priority from U.S. Provisional Application Ser. No. 61/979,416, filed Apr. 14, 2014, and U.S. Provisional Application Ser. No. 62/093,313, filed Dec. 17, 2014, and is also a continuation-in-part of U.S. application Ser. No. 14/459,638, filed Aug. 14, 2014, which claims priority from U.S. Provisional Application Ser. No. 61/866,993, filed Aug. 16, 2013, all of which are herein incorporated by reference in their entirety for all purposes.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels that transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures that often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. Some such procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms and complexity and difficulty in the deployment thereof as most aneurysm treatments with this approach require the deployment of multiple coils.

Another approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

A number of aneurysm neck bridging devices with defect spanning portions or regions have been attempted; however, none of these devices has had a significant measure of clinical success or usage. A major limitation in their adoption and clinical usefulness is the inability to position the defect spanning portion to assure coverage of the neck. Existing stent delivery systems that are neurovascular compatible (i.e., deliverable through a microcatheter and highly flexible) do not have the necessary rotational positioning capability. Another limitation of many aneurysm bridging devices described in the prior art is the poor flexibility. Cerebral blood vessels are tortuous and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm, with a decreased risk of inadvertent aneurysm rupture or blood vessel wall damage. In addition, what have been needed are devices that are easily visible with current imaging technology such as x-ray, fluoroscopy, magnetic resonance imaging and the like.

SUMMARY

One embodiment of a device for treatment of a patient's vasculature includes a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, which define a cavity of the permeable shell and which include at least about 40% composite filaments relative to a total number of filaments, the composite filaments including a high strength material and a highly radiopaque material.

One embodiment of a device for treatment of a patient's vasculature includes a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, the plurality of filaments having a total cross sectional area and further defining a cavity of the permeable shell and which include at least some composite filaments, the composite filaments including a high strength material and a highly radiopaque material, and wherein the total cross sectional area of the highly radiopaque material is between about 11% and about 30% of the total cross sectional area of the plurality of elongate filaments.

In another embodiment of the invention, a device for treating a cerebral aneurysm is described. The device includes an implant comprising woven braided mesh. The implant has a proximal end with a hub, a distal end, and a longitudinal axis extending from the proximal end to the distal end. The implant has a distal region, a proximal region, and a transition region that lies substantially perpendicular to the longitudinal axis of the implant and extends between the distal and proximal regions. The implant also has an expanded configuration when deployed. The expanded implant has a region of maximum diameter that extends from a proximal portion of the distal region through the transition region and to a distal portion of the proximal region. Additionally, a diameter of a pore within the proximal portion of the distal region is larger than all pores in the distal portion of the proximal region.

In another embodiment of the invention, a method for treating a cerebral aneurysm using the above-described device. The method includes providing an implant comprising woven braided mesh, the implant having a proximal end with a hub, a distal end, and a longitudinal axis extending from the proximal end to the distal end. The implant has a distal region, a proximal region, and a transition region that lies substantially perpendicular to the longitudinal axis of the implant and extends between the distal and proximal regions. The implant also has an expanded configuration when deployed. The expanded implant has a region of maximum diameter that extends from a proximal portion of the distal region through the transition region and to a distal portion of the proximal region. Additionally, a diameter of a pore within the proximal portion of the distal region is larger than all pores in the distal portion of the proximal region. The implant is advanced in the low profile radially constrained state within a microcatheter to a region of interest within a cerebral artery. The implant is deployed within the cerebral aneurysm, wherein the distal and proximal permeable shells expand to their expanded shapes. The microcatheter is withdrawn from the region of interest after deploying the implant.

The diameter of a pore in the proximal portion of the distal region is greater than 300 µm, alternatively between about 300 µm and about 900 µm, alternatively between about 300 µm to about 700 µm, alternatively between about 300 µm to about 500 µm. The diameter of a pore in the distal portion of the proximal region is less than 200 µm, alternatively between about 50 µm and about 200 µm, alternatively between about 50 µm to about 200 µm, alternatively between about 50 µm to about 150 µm, and alternatively between about 100 µm to about 200 µm. The transition region may be approximately 1000 µm high, alternatively between about 500 µm to about 1500 µm high, alternatively between about 750 µm to about 1250 µm high. The transition region may have a height that is approximately about 0.5% to about 20% of a total height of the implant, alternatively about 1% to about 15% of a total height of the implant, alternatively about 1% to about 10% of a total height of the implant, and alternatively about 3% to about 8% of a total height of the implant.

In another embodiment of the invention, a device for treating a cerebral aneurysm is described. The device includes a support structure having a first end, a second end, and braided elongate flexible filaments extending from the first end to the second end. The support structure has a low profile radially constrained state and an expanded state that is axially shortened relative to the radially constrained state. The expanded state has a section that has a substantially tubular shape having a first region, a transition zone, and a second region. The elongate flexible filaments are gathered at the first end by the hub. The first region of the expanded state comprises a plurality of pores defined by the braided elongate flexible filaments in the first region, each pore of the plurality of pores having a diameter. The transition zone is immediately adjacent the first region and comprises a plurality of pores defined by the braided elongate flexible filaments in the transition zone, each pore of the plurality of pores having a diameter. The second region is immediately adjacent the transition zone and is located between the transition zone and the first end of the support structure. The second region has a plurality of pores defined by the braided elongate flexible filaments in the second region, each pore of the plurality of pores having a diameter. The diameter of a pore in the transition zone that is adjacent the first region is larger than the diameter of a pore in the transition zone that is adjacent the second region. The diameter of a pore within the first region is larger than the diameters of each of the plurality of pores in the second region.

In another embodiment of the invention, a method for treating a cerebral aneurysm using the above-described device. The method includes providing an implant having a support structure having a first end, a second end, and braided elongate flexible filaments extending from the first end to the second end. The support structure has a low profile radially constrained state and an expanded state that is axially shortened relative to the radially constrained state. The expanded state has a section that has a substantially tubular shape having a first region, a transition zone, and a second region. The elongate flexible filaments are gathered at the first end by the hub. The first region of the expanded state comprises a plurality of pores defined by the braided elongate flexible filaments in the first region, each pore of the plurality of pores having a diameter. The transition zone is immediately adjacent the first region and comprises a plurality of pores defined by the braided elongate flexible filaments in the transition zone, each pore of the plurality of pores having a diameter. The second region is immediately adjacent the transition zone and is located between the transition zone and the first end of the support structure. The second region has a plurality of pores defined by the braided elongate flexible filaments in the second region, each pore of the plurality of pores having a diameter. The diameter of a pore in the transition zone that is adjacent the first region is larger than the diameter of a pore in the transition zone that is adjacent the second region. The diameter of a pore within the first region is larger than the diameters of each of the plurality of pores in the second region. The implant is advanced in the low profile radially constrained state within a microcatheter to a region of interest within a cerebral artery. The implant is deployed within the cerebral aneurysm, wherein the distal and proximal permeable shells expand to their expanded shapes. The microcatheter is withdrawn from the region of interest after deploying the implant.

The substantially tubular shape has a diameter that is substantially the same throughout the section. The elongate flexible filaments may have a constant diameter from the first end to the second end. The diameter of a pore in the first region may be greater than 300 µm, alternatively between about 300 µm and about 900 µm, alternatively between about 300 µm to about 700 µm, alternatively between about 300 µm to about 500 µm. The diameter of a pore in the second region may be less than 200 µm, alternatively between about 50 µm and about 200 µm, alternatively between about 50 µm to about 200 µm, alternatively between about 50 µm to about 150 µm, and alternatively between about 100 µm to about 200 µm. The transition zone may be approximately 1000 µm high, alternatively between about 500 µm to about 1500 µm high, alternatively between about 750 µm to about 1250 µm high. The transition zone may have a height that is approximately about 0.5% to about 20% of a total height of the expanded device, alternatively about 1% to about 15% of a total height of the expanded device, alternatively about 1% to about 10% of a total height of the expanded device, and alternatively about 3% to about 8% of a total height of the expanded device.

The elongate flexible filaments may comprise nitinol, e.g., nitinol wires. The elongate flexible filaments may also be drawn filled tube filaments. The drawn filled tube filaments may comprise nitinol and a highly radiopaque material such as platinum, a platinum alloy, gold, or tantalum. The elongate flexible filaments may also be a mixture of nitinol wires and drawn filled tubes. The elongate flexible filaments may have a transverse dimension of between about 0.0005 inches to about 0.002 inches, alternatively between about 0.00075 inches to 0.00125 inches. The braided elongate flexible filaments may include first and second filaments each having a transverse dimension. The transverse dimension of the first filament may be smaller than the transverse dimension of the second filament. The support structure comprises between about 76 to 216 filaments. The elongate flexible filaments may be gathered at the second end by the additional hub, which may be radiopaque. The additional hub may be recessed at the second end in the expanded state. Alternatively, the elongate flexible filaments may not be gathered at the second end, such that the second end is open.

In another embodiment, a device for treating a cerebral aneurysm is described. The device includes a support structure having a first end, a second end, and braided elongate flexible filaments extending from the first end to the second end. The support structure has a low profile radially constrained state and an expanded state that is axially shortened relative to the radially constrained state. The expanded state has a section having a substantially tubular shape having a first region, a transition zone, and a second region. The elongate flexible filaments are gathered at the first end by the hub. The flexible filaments of the first region define a plurality of pores. The filaments that define each pore are arranged in a first diamond shape, each pore having a first diameter defined by the braided elongate flexible filaments of the first region. The transition zone is immediately adjacent the first region and comprises flexible filaments that define a plurality of pores, each pore having a diameter defined by the braided elongate flexible filaments. The flexible filaments of the second region immediately adjacent the transition zone are located between the transition zone and the first end of the support structure. The filaments of the second region define a plurality of pores, wherein the filaments that define each pore are arranged in a second diamond shape, each pore having a second diameter defined by the braided elongate flexible filaments of the second region. The first diamond shape defines an angle β1 at the 3 o'clock position when the angle at the 6 o'clock position is closest to the first end. The second diamond shape defines an angle β2 at the 3 o'clock position when the angle at the 6 o'clock position is closest to the first end. Angle β1 is greater than angle β2.

In another embodiment of the invention, a method for treating a cerebral aneurysm using the above-described device. The method includes providing a support structure having a first end, a second end, and braided elongate flexible filaments extending from the first end to the second end. The support structure has a low profile radially constrained state and an expanded state that is axially shortened relative to the radially constrained state. The expanded state has a section having a substantially tubular shape having a first region, a transition zone, and a second region. The elongate flexible filaments are gathered at the first end by the hub. The flexible filaments of the first region define a plurality of pores. The filaments that define each pore are arranged in a first diamond shape, each pore having a first diameter defined by the braided elongate flexible filaments of the first region. The transition zone is immediately adjacent the first region and comprises flexible filaments that define a plurality of pores, each pore having a diameter defined by the braided elongate flexible filaments. The flexible filaments of the second region immediately adjacent the transition zone are located between the transition zone and the first end of the support structure. The filaments of the second region define a plurality of pores, wherein the filaments that define each pore are arranged in a second diamond shape, each pore having a second diameter defined by the braided elongate flexible filaments of the second region. The first diamond shape defines an angle β1 at the 3 o'clock position when the angle at the 6 o'clock position is closest to the first end. The second diamond shape defines an angle β2 at the 3 o'clock position when the angle at the 6 o'clock position is closest to the first end. Angle β1 is greater than angle β2. The implant is advanced in the low profile radially constrained state within a microcatheter to a region of interest within a cerebral artery. The implant is deployed within the cerebral aneurysm, wherein the distal and proximal permeable shells expand to their expanded shapes. The microcatheter is withdrawn from the region of interest after deploying the implant.

The section having a substantially tubular shape has a diameter that is substantially the same throughout the section. Angle β1 may be between about 35° and 65°, alternatively between about 45° and 55°. Angle β2 may be between about 25° and 45°, alternatively between about 30° and 40°. The elongate flexible filaments have a constant diameter from the first end to the second end.

The transition zone may be approximately 1000 µm high, alternatively between about 500 µm to about 1500 µm high, alternatively between about 750 µm to about 1250 µm high. The transition zone may have a height that is approximately about 0.5% to about 20% of a total height of the expanded device, alternatively about 1% to about 15% of a total height of the expanded device, alternatively about 1% to about 10% of a total height of the expanded device, and alternatively about 3% to about 8% of a total height of the expanded device.

The elongate flexible filaments may comprise nitinol, e.g., nitinol wires. The elongate flexible filaments may also be drawn filled tube filaments. The drawn filled tube filaments may comprise nitinol and a highly radiopaque material such as platinum, a platinum alloy, gold, or tantalum. The elongate flexible filaments may also be a mixture of nitinol wires and drawn filled tubes. The elongate flexible filaments may have a transverse dimension of between about 0.0005 inches to about 0.002 inches, alternatively between about 0.00075 inches to 0.00125 inches. The braided elongate flexible filaments may include first and second filaments each having a transverse dimension. The transverse dimension of the first filament may be smaller than the transverse dimension of the second filament. The support structure comprises between about 76 to 216 filaments. The elongate flexible filaments may be gathered at the second end by the additional hub, which may be radiopaque. The additional hub may be recessed at the second end in the expanded state. Alternatively, the elongate flexible filaments may not be gathered at the second end, such that the second end is open.

In another embodiment of the invention, a method of forming a tubular braid is described. The method includes the step of loading a plurality of elongate resilient filaments onto a mandrel extending perpendicularly from the center of a disc, the disc defining a plane and a circumferential edge. The plurality of filaments are loaded such that each filament extends radially from the mandrel towards the circumferential edge of the disc and engages the circumferential edge of the disc at an independent point of engagement separated by a distance d from adjacent points of engagement. An initial tension $T_{i1}$ is then applied on each of a first subset of filaments and an initial tension $T_{i2}$ is applied on a second subset of filaments. A weighted structure having a weight $W_1$ is placed over the plurality of filaments and the mandrel, the weighted structure having an inner diameter that is slightly larger than a profile of the plurality of filaments over the mandrel. The first subset of filaments is engaged with a plurality of actuators. The plurality of actuators is operated to move the engaged filaments in a generally radial direction to a radial position beyond the circumferential edge of the disc. At least one of the disc or the plurality of actuators is rotated, thereby rotationally displacing the second subset of filaments and the first subset of filaments in relation to one another a discrete distance and crossing the filaments of the first subset over the filaments of the second subset. The plurality of actuators is operated to move the first subset of filaments in a generally radial direction toward the circumferential edge of the disc, wherein each filament in the first subset engages the circumferential edge of the disc at a point of engagement that is a circumferential distance from its previous point of engagement. The second subset of filaments is then engaged. The plurality of actuators is operated to move the engaged filaments to a radial position beyond the circumferential edge of the disc. At least one of the disc or the plurality of actuators is rotated, thereby rotationally displacing a second subset of filaments and the first subset of filaments in relation to one another a discrete distance and crossing the filaments of the second subset over the filaments of the first subset. The plurality of actuators is operated to move the second subset of filaments in a generally radial direction toward the circumferential edge of the disc, wherein each filament in the second subset engages the circumferential edge of the disc at a point of engagement that is a circumferential distance from its previous point of engagement. The above steps are repeated to form a first portion of a tubular braid having a plurality of pores, each pore of the plurality of pores in the first portion having a diameter.

The weighted structure is then replaced or changed such that a weight $W_2$, different from weight $W_1$ is applied over the plurality of filaments and the mandrel. The above steps are repeated with the weight $W_2$ to continue forming a second portion of the tubular braid having a plurality of pores, each pore of the plurality of pores in the second portion having a diameter. The average diameter of the plurality of pores in the first portion is different than the average diameter of the plurality of pores in the second portion.

The method may also include the steps of securing ends of the plurality of elongate resilient filaments at a first end of the tubular braid. At least a portion of the tubular braid is deformed. The tubular braid may be maintained in the at least partially deformed state with a substantially rigid tool. The at least partially deformed tubular braid may be raised past a critical temperature at which a significant molecular reorientation occurs in the elongate resilient filaments. The tubular braid may then be lowered below the critical temperature. The substantially rigid tool may then be removed.

The initial tensions $T_{i1}$ is equal to $T_{i2}$ applied to the subsets of filaments may be equal. The initial tension $T_{i1}$ may be applied by coupling a first plurality of tensioning elements to the first subset of filaments. Similarly, the initial tension $T_{i2}$ may be applied by coupling a second plurality of tensioning elements to the second subset of filaments. A secondary tension $T_{s1}$ may also be applied by adding weights to each of the first subset of filaments and the second subset of filaments. The first plurality of tensioning elements may be weights. The secondary tension $T_{s1}$ may be applied by removing weights to each of the first subset of filaments and the second subset of filaments. The weighted structure $W_1$ may be greater than $W_2$. Alternatively, $W_1$ may be less than $W_2$. The mandrel may extend in a substantially vertical direction. $W_1$ may be at least 1.5 times as large as $W_2$. $W_1$ may be at least 263 grams. $W_1$ and $W_2$ may each be between about 25 grams and about 1,600 grams, alternatively between about 50 grams and about 500 grams, alternatively between about 87 grams and about 263 grams.

The first portion has a first braid density $BD_1$ and the second portion has a second braid density $BD_2$. $BD_1$, may be different from $BD_2$. The first braid density $BD_1$ may be between about 0.10 and 0.15. The second braid density $BD_2$ may be greater than the first braid density $BD_1$. The second braid density $BD_2$ may be in the range of about 1.25 to about 5.0 times, alternatively about 1.50 to about 2.0 times, alternatively about 0.15 to about 0.40 times, alternatively about 0.17 to about 0.30 times the first braid density $BD_1$. The average diameter of the plurality of pores in the second portion may be 200 µm or less, alternatively between about 50 µm to about 200 µm, alternatively between about 100 µm to about 200 µm. The average diameter of the plurality of pores in the first portion may be greater than 200 µm, alternatively greater than 250 µm, greater than 300 µm, greater than 400 µm, alternatively between about 250 µm to about 500 µm, alternatively about 300 µm to about 600 µm.

In another embodiment of the invention, a method of forming a tubular braid is described. The method includes the steps of loading a plurality of elongate resilient filaments, each having a first and second end, onto a castellated mandrel assembly extending perpendicularly from the center of a disc, the disc defining a plane and a circumferential edge. The castellated mandrel assembly includes a convex cap surrounded by a cylindrical battlement-like structure at a first end, the cylindrical battlement-like structure having a plurality of slots separated by a plurality of posts, such that a middle portion of each filament is positioned across the convex cap and passes through first and second slots. Each of the first and second ends of the plurality of filaments extends radially from the castellated mandrel assembly towards the circumferential edge of the disc and engages the circumferential edge of the disc at an independent point of engagement separated by a distance d from adjacent points of engagement. An initial tension $T_1$ is applied on each of a first subset of filaments and an initial tension $T_{i2}$ is applied on a second subset of filaments. A weighted structure is placed over the plurality of filaments and the mandrel, the weighted structure having an inner diameter that is slightly larger than a profile of the plurality of filaments over the mandrel, the weighted structure having a weight $W_1$. The first subset of filaments is engaged with a plurality of actuators. The plurality of actuators is operated to move the engaged filaments in a generally radial direction to a radial position beyond the circumferential edge of the disc. At least one of the disc or the plurality of actuators is rotated, thereby rotationally displacing the second subset of filaments and the first subset of filaments in relation to one another a discrete distance and crossing the filaments of the first subset over the filaments of the second subset. The plurality of actuators is operated to move the first subset of filaments in a generally radial direction toward the circumferential edge of the disc, wherein each filament in the first subset engages the circumferential edge of the disc at a point of engagement that is a circumferential distance from its previous point of engagement. The second subset of filaments is engaged. The plurality of actuators is operated to move the engaged filaments to a radial position beyond the circumferential edge of the disc. At least one of the disc or the plurality of actuators is rotated, thereby rotationally displacing a second subset of filaments and the first subset of filaments in relation to one another a discrete distance and crossing the filaments of the second subset over the filaments of the first subset. The plurality of actuators is operated to move the second subset of filaments in a generally radial direction toward the circumferential edge of the disc, wherein each filament in the second subset engages the circumferential edge of the disc at a point of engagement that is a circumferential distance from its previous point of engagement. The above steps are repeated to form a first portion of a tubular braid having a plurality of pores, each pore of the plurality of pores in the first portion having a diameter.

The method may also include the steps of replacing or changing the weighted structure such that a weight $W_2$, different from weight $W_1$, is applied over the plurality of filaments and the mandrel. The above steps are repeated with the weight $W_2$ to continue forming a second portion of the tubular braid having a plurality of pores, each pore of the plurality of pores in the second portion having a diameter, wherein the average diameter of the plurality of pores in the first portion is different than the average diameter of the plurality of pores in the second portion.

The cylindrical battlement-like structure extends 360° around the castellated mandrel assembly. The first slot may be located approximately 180° from the second slot. Alternatively, the first slot may be located less than 90° from the second slot. Alternatively, the first slot may be located between 30° and 160° from the second slot. The cylindrical battlement-like structure may have at least 18 slots.

In another embodiment, a device for treatment of an aneurysm is described. The device includes a self-expanding resilient permeable shell having a proximal end, a distal end, and a longitudinal axis. The permeable shell includes a plurality of elongate resilient filaments having a braided structure, each of the plurality of elongate filaments having a first end, a central section, and a second end. The first and second ends of the plurality of filaments are secured at the proximal end of the permeable shell. The permeable shell is a single layer of braided elongate resilient filaments. The permeable shell has a radially constrained elongated state configured for delivery within a microcatheter. The permeable shell also has an expanded relaxed state with a globular, axially shortened configuration relative to the radially constrained state, wherein the central section of each of the plurality of elongate filaments passes through a distal region of the permeable shell.

In another embodiment of the invention, a method for treating a cerebral aneurysm using the above-described device. The method includes providing device that includes a self-expanding resilient permeable shell having a proximal end, a distal end, and a longitudinal axis. The permeable shell includes a plurality of elongate resilient filaments having a braided structure, each of the plurality of elongate filaments having a first end, a central section, and a second end. The first and second ends of the plurality of filaments are secured at the proximal end of the permeable shell. The permeable shell is a single layer of braided elongate resilient filaments. The permeable shell has a radially constrained elongated state configured for delivery within a microcatheter. The permeable shell also has an expanded relaxed state with a globular, axially shortened configuration relative to the radially constrained state, wherein the central section of each of the plurality of elongate filaments passes through a distal region of the permeable shell. The device is advanced in the low profile radially constrained state within a microcatheter to a region of interest within a cerebral artery. The device is deployed within the cerebral aneurysm, wherein the distal and proximal permeable shells expand to their expanded shapes. The microcatheter is withdrawn from the region of interest after deploying the device.

The plurality of elongate filaments may not be secured together at the distal end of the permeable shell. The plurality of filaments comprises filaments of at least two different transverse dimensions. The plurality of filaments may comprise nitinol, e.g., nitinol wires. The filaments may also be drawn filled tubes. At least some of the filaments may be bioresorbable filaments made from bioresorbable materials such as PGLA, PGA, or PLLA.

The distal end of the permeable shell may be made of a plurality of loops formed from single filaments. The proximal end of the permeable shell may be made up of a plurality of loops formed from single filaments. The device may have an opening at the proximal end. The opening may have a diameter of at least one millimeter. The opening may be configured to allow the passage of a microcatheter. At least a portion of the permeable shell may be coated with a growth factor such as CE34 antibody.

The device may optionally have a permeable layer having a proximal end, a distal end, and a longitudinal axis, the permeable layer comprising a plurality of elongate resilient filaments having a braided structure, the permeable layer disposed inside or outside of the permeable shell. The device may be the only implant delivered to the aneurysm, i.e., no embolic material is placed within the permeable shell.

Alternatively, at least a portion of the permeable shell may be configured to contain an embolic material.

For the devices described above that have an open proximal end, the implant or permeable shell may be the only device delivered to (used to treat) the aneurysm. Optionally, additional devices, such as embolic coils, may also be delivered to the aneurysm (e.g., placed inside the implant or permeable shell).

BRIEF DESCRIPTION OF THE DRAWINGS

FIG. 12 is an elevation view of a distal portion of a delivery device or actuator showing some internal structure of the device.

FIG. 13 is an elevation view of the delivery device of FIG. 12 with the addition of some tubular elements over the internal structures.

FIG. 14 is an elevation view of the distal portion of the delivery device of FIG. 13 with an outer coil and marker in place.

FIG. 15 is an elevation view of a proximal portion of the delivery device.

FIGS. 23-26 show a deployment sequence of a device for treatment of a patient's vasculature.

FIG. 46 is an elevation view in partial section of an embodiment of a device for treatment of a patient's vasculature.

FIG. 47 represents the image of an angiogram depicting an aneurysm prior to treatment.

FIG. 48 is depicts the aneurysm of FIG. 47 ten (10) minutes post-treatment.

FIG. 55 is an elevation view of an embodiment of a device for treatment of a patient's vasculature.

FIG. 56 is an elevation view of an embodiment of a device for treatment of a patient's vasculature.

FIG. 57 is the embodiment of a device for treatment of a patient's vasculature of FIG. 55 deployed within an aneurysm.

FIG. 58 is the embodiment of a device for treatment of a patient's vasculature of FIG. 56 deployed within an aneurysm.

FIG. 59 is an elevation view of an embodiment of a device for treatment of a patient's vasculature.

FIG. 60 is an elevation view of an embodiment of a device for treatment of a patient's vasculature.

FIG. 63E is a perspective view of an embodiment of a device for treatment of a patient's vasculature.

DETAILED DESCRIPTION

Figure 1:
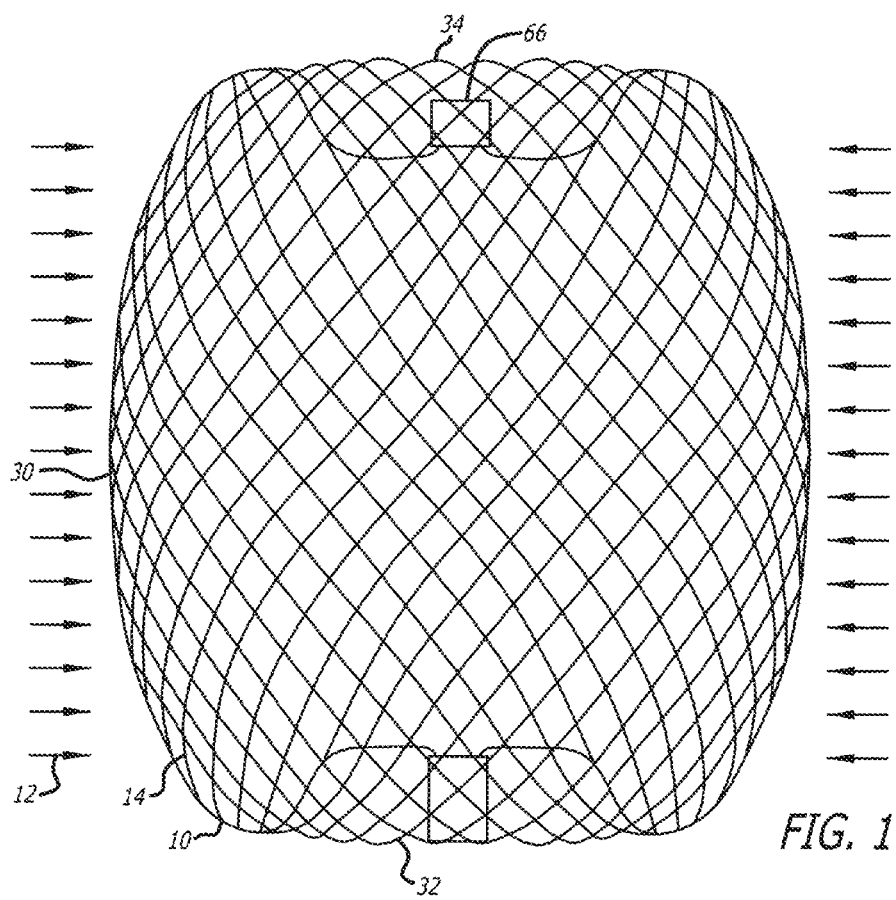
FIG. 1 is an elevation view of an embodiment of a device for treatment of a patient's vasculature and a plurality of arrows indicating inward radial force.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. It may also be desirable for some device embodiments to acutely occlude a vascular defect of a patient during the course of a procedure in order to provide more immediate feedback regarding success of the treatment to a treating physician.

It should be appreciated by those skilled in the art that unless otherwise stated, one or more of the features of the various embodiments may be used in other embodiments.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, a permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell may be configured to allow some initial perfusion of blood through the permeable shell. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane the dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

For some embodiments, three factors may be critical for a woven or braided wire occlusion device for treatment of a patient's vasculature that can achieve a desired clinical outcome in the endovascular treatment of cerebral aneurysms. We have found that for effective use in some applications, it may be desirable for the implant device to have sufficient radial stiffness for stability, limited pore size for near-complete acute (intra-procedural) occlusion and a collapsed profile that is small enough to allow insertion through an inner lumen of a microcatheter. A device with a radial stiffness below a certain threshold may be unstable and may be at higher risk of embolization in some cases. Larger pores between filament intersections in a braided or woven structure may not generate thrombus and occlude a vascular defect in an acute setting and thus may not give a treating physician or health professional such clinical feedback that the flow disruption will lead to a complete and lasting occlusion of the vascular defect being treated. Delivery of a device for treatment of a patient's vasculature through a standard microcatheter may be highly desirable to allow access through the tortuous cerebral vasculature in the manner that a treating physician is accustomed.

For some embodiments, it may be desirable to use filaments having two or more different diameters or transverse dimensions to form a permeable shell in order to produce a desired configuration as discussed in more detail below. The radial stiffness of a two-filament (two different diameters) woven device may be expressed as a function of the number of filaments and their diameters, as follows:

$$S_{radial} = (1.2 \times 10^6 \text{ lbf}/D^4)(N_l d_l^4 + N_s d_s^4)$$

where $S_{radial}$ is the radial stiffness in pounds force (lbf),
D is the Device diameter (transverse dimension),
$N_l$ is the number of large filaments,
$N_s$ is the number of small filaments,
$d_l$ is the diameter of the large filaments in inches, and
$d_s$ is the diameter of the small filaments in inches.

Using this expression, the radial stiffness, $S_{radial}$ may be between about 0.014 and about 0.284 lbf force for some embodiments of particular clinical value. In some embodiments, the radial stiffness $S_{radial}$ may be between about 0.015 and about 0.065 lbf. In some embodiments, the radial stiffness $S_{radial}$ may be measured at a deformation of about 50%.

The maximum pore size in a portion of a device that spans a neck or opening of a vascular defect desirable for some useful embodiments of a woven wire device for treatment of a patient's vasculature may be expressed as a function of the total number of all filaments, filament diameter and the device diameter. The difference between filament sizes where two or more filament diameters or transverse dimensions are used, may be ignored in some cases for devices where the filament size(s) are very small compared to the device dimensions. For a two-filament device, the smallest filament diameter may be used for the calculation. Thus, the maximum pore size for such embodiments may be expressed as follows:

$$P_{max} = (1.7/N_T)(\pi D - (N_T d_w/2))$$

where $P_{max}$ is the average pore size,
D is the Device diameter (transverse dimension),
$N_T$ is the total number of all filaments, and
$d_w$ is the diameter of the filaments (smallest) in inches.

Using this expression, the maximum pore size, $P_{max}$, of a portion of a device that spans an opening of a vascular defect or neck, or any other suitable portion of a device, may be less than about 0.016 inches or about 400 microns for some embodiments. In some embodiments the maximum pore size for a defect spanning portion or any other suitable portion of a device may be less than about 0.012 inches or about 300 microns. In some embodiments, the maximum pore size for a defect spanning portion or any other suitable portion of a device may be less than about 0.008 inches or about 200 microns.

The collapsed profile of a two-filament (profile having two different filament diameters) woven filament device may be expressed as the function:

$$P_c = 1.48((N_l d_l^2 + N_s d_s^2))^{1/2}$$

where $P_c$ is the collapsed profile of the device,
$N_l$ is the number of large filaments,
$N_s$ is the number of small filaments,
$d_l$ is the diameter of the large filaments in inches, and
$d_s$ is the diameter of the small filaments in inches.

Using this expression, the collapsed profile Pc may be less than about 1.0 mm for some embodiments of particular clinical value. In some embodiments of particular clinical value, the device may be constructed so as to have all three factors ($S_{radial}$, $P_{max}$ and $P_c$) above within the ranges discussed above; $S_{radial}$ between about 0.014 lbf and about 0.284 lbf, or between about 0.015 lbf and about 0.065 lbf, $P_{max}$ less than about 300 microns and $P_c$ less than about 1.0 mm, simultaneously. In some such embodiments, the device may be made to include about 70 filaments to about 300 filaments. In some cases, the filaments may have an outer transverse dimension or diameter of about 0.0004 inches to about 0.002 inches. In some cases the filaments may have an outer transverse dimension or diameter of about 0.0005 inches to about 0.0015 inches, alternatively about 0.00075 inches to about 0.00125 inches.

As has been discussed, some embodiments of devices for treatment of a patient's vasculature call for sizing the device which approximates (or with some over-sizing) the vascular site dimensions to fill the vascular site. One might assume that scaling of a device to larger dimensions and using larger filaments would suffice for such larger embodiments of a device. However, for the treatment of brain aneurysms, the diameter or profile of the radially collapsed device is limited by the catheter sizes that can be effectively navigated within the small, tortuous vessels of the brain. Further, as a device is made larger with a given or fixed number of resilient filaments having a given size or thickness, the pores or openings between junctions of the filaments are correspondingly larger. In addition, for a given filament size the flexural modulus or stiffness of the filaments and thus the structure decrease with increasing device dimension. Flexural modulus may be defined as the ratio of stress to strain. Thus, a device may be considered to have a high flexural modulus or be stiff if the strain (deflection) is low under a given force. A stiff device may also be said to have low compliance.

Figure 2:
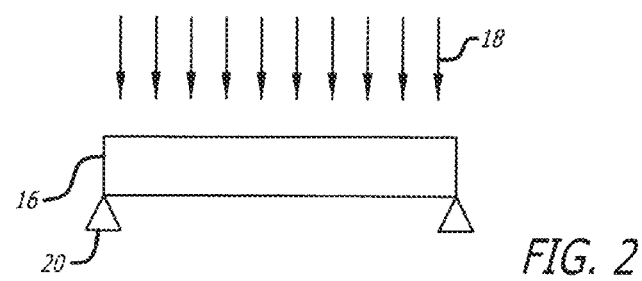
FIG. 2 is an elevation view of a beam supported by two simple supports and a plurality of arrows indicating force against the beam.
Figure 3:
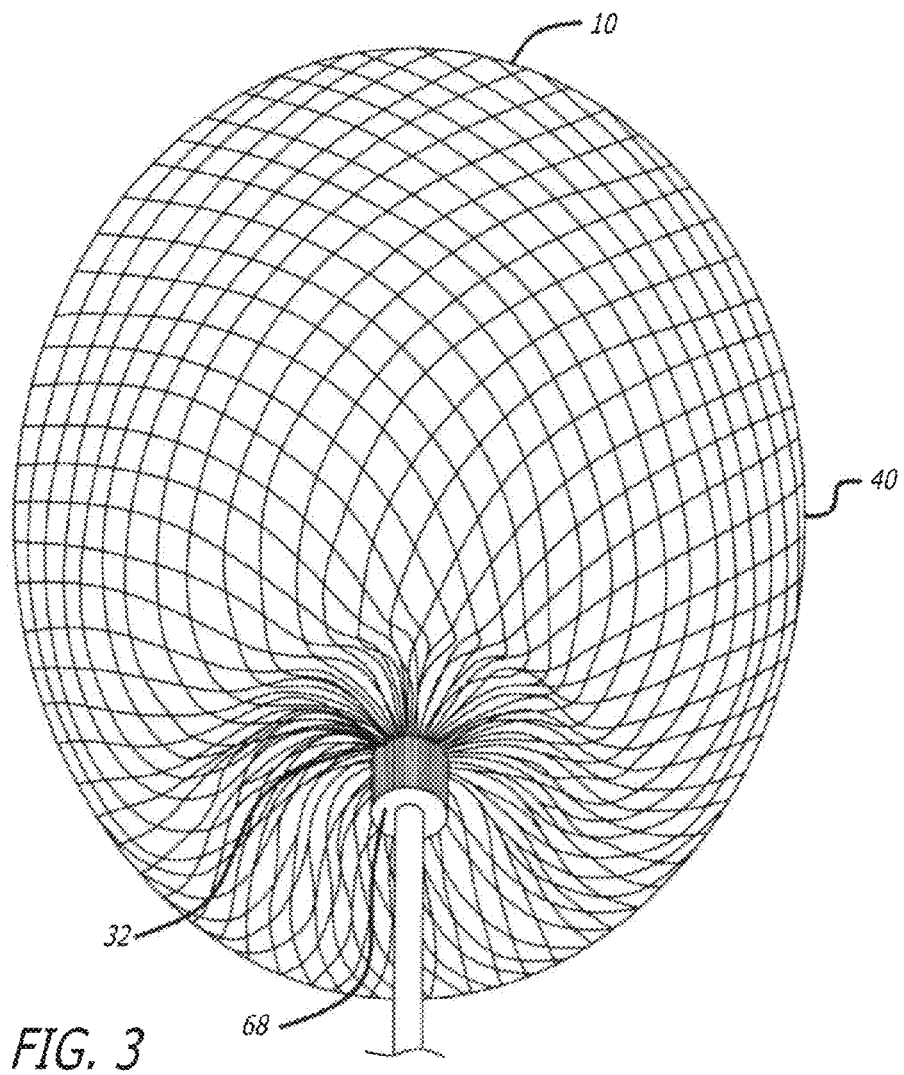
FIG. 3 is a bottom perspective view of an embodiment of a device for treatment of a patient's vasculature.

To properly configure larger size devices for treatment of a patient's vasculature, it may be useful to model the force on a device when the device is deployed into a vascular site or defect, such as a blood vessel or aneurysm, that has a diameter or transverse dimension that is smaller than a nominal diameter or transverse dimension of the device in a relaxed unconstrained state. As discussed, it may be advisable to "over-size" the device in some cases so that there is a residual force between an outside surface of the device and an inside surface of the vascular wall. The inward radial force on a that results from over-sizing is illustrated schematically in FIG. 1 with the arrows 12 in the figure representing the inward radial force. As shown in FIG. 2, these compressive forces on the filaments 14 of the device in FIG. 1 can be modeled as a simply supported beam 16 with a distributed load or force as shown by the arrows 18 in the figure. It can be seen from the equation below for the deflection of a beam with two simple supports 20 and a distributed load that the deflection is a function of the length, L to the 4th power:

Deflection of Beam=$5FL^4/384EI$ where F=force,
L=length of beam,
E=Young's Modulus, and
I=moment of inertia.

Thus, as the size of the device increases and L increases, the compliance increases substantially. Accordingly, an outward radial force exerted by an outside surface of the filaments 14 of the device 10 against a constraining force when inserted into a vascular site such as blood vessel or aneurysm is lower for a given amount of device compression or over-sizing. This force may be important in some applications to assure device stability and to reduce the risk of migration of the device and potential distal embolization.

In some embodiments, a combination of small and large filament sizes may be utilized to make a device with a desired radial compliance and yet have a collapsed profile that is configured to fit through an inner lumen of commonly used microcatheters. A device fabricated with even a small number of relatively large filaments 14 can provide reduced radial compliance (or increased stiffness) compared to a device made with all small filaments. Even a relatively small number of larger filaments may provide a substantial increase in bending stiffness due to change in the moment of Inertia that results from an increase in diameter without increasing the total cross sectional area of the filaments. The moment of inertia (I) of a round wire or filament may be defined by the equation:

$I=\pi d^4/64$ where d is the diameter of the wire or filament.

Since the moment of inertia is a function of filament diameter to the fourth power, a small change in the diameter greatly increases the moment of inertia. Thus, a small change in filament size can have substantial impact on the deflection at a given load and thus the compliance of the device.

Thus, the stiffness can be increased by a significant amount without a large increase in the cross sectional area of a collapsed profile of the device 10. This may be particularly important as device embodiments are made larger to treat large aneurysms. While large cerebral aneurysms may be relatively rare, they present an important therapeutic challenge as some embolic devices currently available to physicians have relatively poor results compared to smaller aneurysms.

As such, some embodiments of devices for treatment of a patient's vasculature may be formed using a combination of filaments 14 with a number of different diameters such as 2, 3, 4, 5 or more different diameters or transverse dimensions. In device embodiments where filaments with two different diameters are used, some larger filament embodiments may have a transverse dimension of about 0.001 inches to about 0.004 inches and some small filament embodiments may have a transverse dimension or diameter of about 0.0004 inches and about 0.0015 inches, more specifically, about 0.0004 inches to about 0.001 inches. The ratio of the number of large filaments to the number of small filaments may be between about 2 and 12 and may also be between about 4 and 8. In some embodiments, the difference in diameter or transverse dimension between the larger and smaller filaments may be less than about 0.004 inches, more specifically, less than about 0.0035 inches, and even more specifically, less than about 0.002 inches. As discussed above, it may not always be necessary for all wires or filaments to meet the parameters for the various relationships discussed herein. This may be particularly true where relatively large numbers of filaments are being used for a distinct structure. In some cases, a filamentary structure may meet the relationship constraints discussed herein where the predominance of filaments of a permeable shell or inner structure meet a size constraint.

As discussed above, device embodiments 10 for treatment of a patient's vasculature may include a plurality of wires, fibers, threads, tubes or other filamentary elements that form a structure that serves as a permeable shell. For some embodiments, a globular shape may be formed from such filaments by connecting or securing the ends of a tubular braided structure. For such embodiments, the density of a braided or woven structure may inherently increase at or near the ends where the wires or filaments 14 are brought together and decrease at or near a middle portion 30 disposed between a proximal end 32 and distal end 34 of the permeable shell 40. For some embodiments, an end or any other suitable portion of a permeable shell 40 may be positioned in an opening or neck of a vascular defect such as an aneurysm for treatment. As such, a braided or woven filamentary device with a permeable shell may not require the addition of a separate defect spanning structure having properties different from that of a nominal portion of the permeable shell to achieve hemostasis and occlusion of the vascular defect. Such a filamentary device may be fabricated by braiding, weaving or other suitable filament fabrication techniques. Such device embodiments may be shape set into a variety of three dimensional shapes such as discussed herein. For example, any suitable braiding mechanism embodiment or braiding method embodiment such as those discussed in commonly owned U.S. Patent Publication No. 2013/0092013, published Apr. 18, 2013, titled "Braiding Mechanism and Methods of Use", which is incorporated by reference herein in its entirety, may be used to construct device embodiments disclosed herein.

Referring to FIGS. 3-10, an embodiment of a device for treatment of a patient's vasculature 10 is shown. The device 10 includes a self-expanding resilient permeable shell 40 having a proximal end 32, a distal end 34, a longitudinal axis 46 and further comprising a plurality of elongate resilient filaments 14 including large filaments 48 and small filaments 50 of at least two different transverse dimensions as shown in more detail in FIGS. 5, 7 and 18. The filaments 14 have a woven structure and are secured relative to each other at proximal ends 60 and distal ends 62 thereof. The permeable shell 40 of the device has a radially constrained elongated state configured for delivery within a microcatheter 61, as shown in FIG. 11, with the thin woven filaments 14 extending longitudinally from the proximal end 42 to the distal end 44 radially adjacent each other along a length of the filaments.

As shown in FIGS. 3-6, the permeable shell 40 also has an expanded relaxed state with a globular and longitudinally shortened configuration relative to the radially constrained state. In the expanded state, the woven filaments 14 form the self-expanding resilient permeable shell 40 in a smooth path radially expanded from a longitudinal axis 46 of the device between the proximal end 32 and distal end 34. The woven structure of the filaments 14 includes a plurality of openings 64 in the permeable shell 40 formed between the woven filaments. For some embodiments, the largest of said openings 64 may be configured to allow blood flow through the openings only at a velocity below a thrombotic threshold velocity. Thrombotic threshold velocity has been defined, at least by some, as the time-average velocity at which more than 50% of a vascular graft surface is covered by thrombus when deployed within a patient's vasculature. In the context of aneurysm occlusion, a slightly different threshold may be appropriate. Accordingly, the thrombotic threshold velocity as used herein shall include the velocity at which clotting occurs within or on a device, such as device 10, deployed within a patient's vasculature such that blood flow into a vascular defect treated by the device is substantially blocked in less than about 1 hour or otherwise during the treatment procedure. The blockage of blood flow into the vascular defect may be indicated in some cases by minimal contrast agent entering the vascular defect after a sufficient amount of contrast agent has been injected into the patient's vasculature upstream of the implant site and visualized as it dissipates from that site. Such sustained blockage of flow within less than about 1 hour or during the duration of the implantation procedure may also be referred to as acute occlusion of the vascular defect.

As such, once the device 10 is deployed, any blood flowing through the permeable shell may be slowed to a velocity below the thrombotic threshold velocity and thrombus will begin to form on and around the openings in the permeable shell 40. Ultimately, this process may be configured to produce acute occlusion of the vascular defect within which the device 10 is deployed. For some embodiments, at least the distal end of the permeable shell 40 may have a reverse bend in an everted configuration such that the secured distal ends 62 of the filaments 14 are withdrawn axially within the nominal permeable shell structure or contour in the expanded state. For some embodiments, the proximal end of the permeable shell further includes a reverse bend in an everted configuration such that the secured proximal ends 60 of the filaments 14 are withdrawn axially within the nominal permeable shell structure 40 in the expanded state. As used herein, the term everted may include a structure that is everted, partially everted and/or recessed with a reverse bend as shown in the device embodiment of FIGS. 3-6. For such embodiments, the ends 60 and 62 of the filaments 14 of the permeable shell or hub structure disposed around the ends may be withdrawn within or below the globular shaped periphery of the permeable shell of the device.

The elongate resilient filaments 14 of the permeable shell 40 may be secured relative to each other at proximal ends 60 and distal ends 62 thereof by one or more methods including welding, soldering, adhesive bonding, epoxy bonding or the like. In addition to the ends of the filaments being secured together, a distal hub 66 may also be secured to the distal ends 62 of the thin filaments 14 of the permeable shell 40 and a proximal hub 68 secured to the proximal ends 60 of the thin filaments 14 of the permeable shell 40. The proximal hub 68 may include a cylindrical member that extends proximally beyond the proximal ends 60 of the thin filaments so as to form a cavity 70 within a proximal portion of the proximal hub 68. The proximal cavity 70 may be used for holding adhesives such as epoxy, solder or any other suitable bonding agent for securing an elongate detachment tether 72 that may in turn be detachably secured to a delivery apparatus such as is shown in FIGS. 11-15.

For some embodiments, the elongate resilient filaments 14 of the permeable shell 40 may have a transverse cross section that is substantially round in shape and be made from a superelastic material that may also be a shape memory metal. The shape memory metal of the filaments of the permeable shell 40 may be heat set in the globular configuration of the relaxed expanded state as shown in FIGS. 3-6. Suitable superelastic shape memory metals may include alloys such as NiTi alloy and the like. The superelastic properties of such alloys may be useful in providing the resilient properties to the elongate filaments 14 so that they can be heat set in the globular form shown, fully constrained for delivery within an inner lumen of a microcatheter and then released to self-expand back to substantially the original heat set shape of the globular configuration upon deployment within a patient's body.

The device 10 may have an everted filamentary structure with a permeable shell 40 having a proximal end 32 and a distal end 34 in an expanded relaxed state. The permeable shell 40 has a substantially enclosed configuration for the embodiments shown. Some or all of the permeable shell 40 of the device 10 may be configured to substantially block or impede fluid flow or pressure into a vascular defect or otherwise isolate the vascular defect over some period of time after the device is deployed in an expanded state. The permeable shell 40 and device 10 generally also has a low profile, radially constrained state, as shown in FIG. 11, with an elongated tubular or cylindrical configuration that includes the proximal end 32, the distal end 34 and a longitudinal axis 46. While in the radially constrained state, the elongate flexible filaments 14 of the permeable shell 40 may be disposed substantially parallel and in close lateral proximity to each other between the proximal end and distal end forming a substantially tubular or compressed cylindrical configuration.

Figure 4:
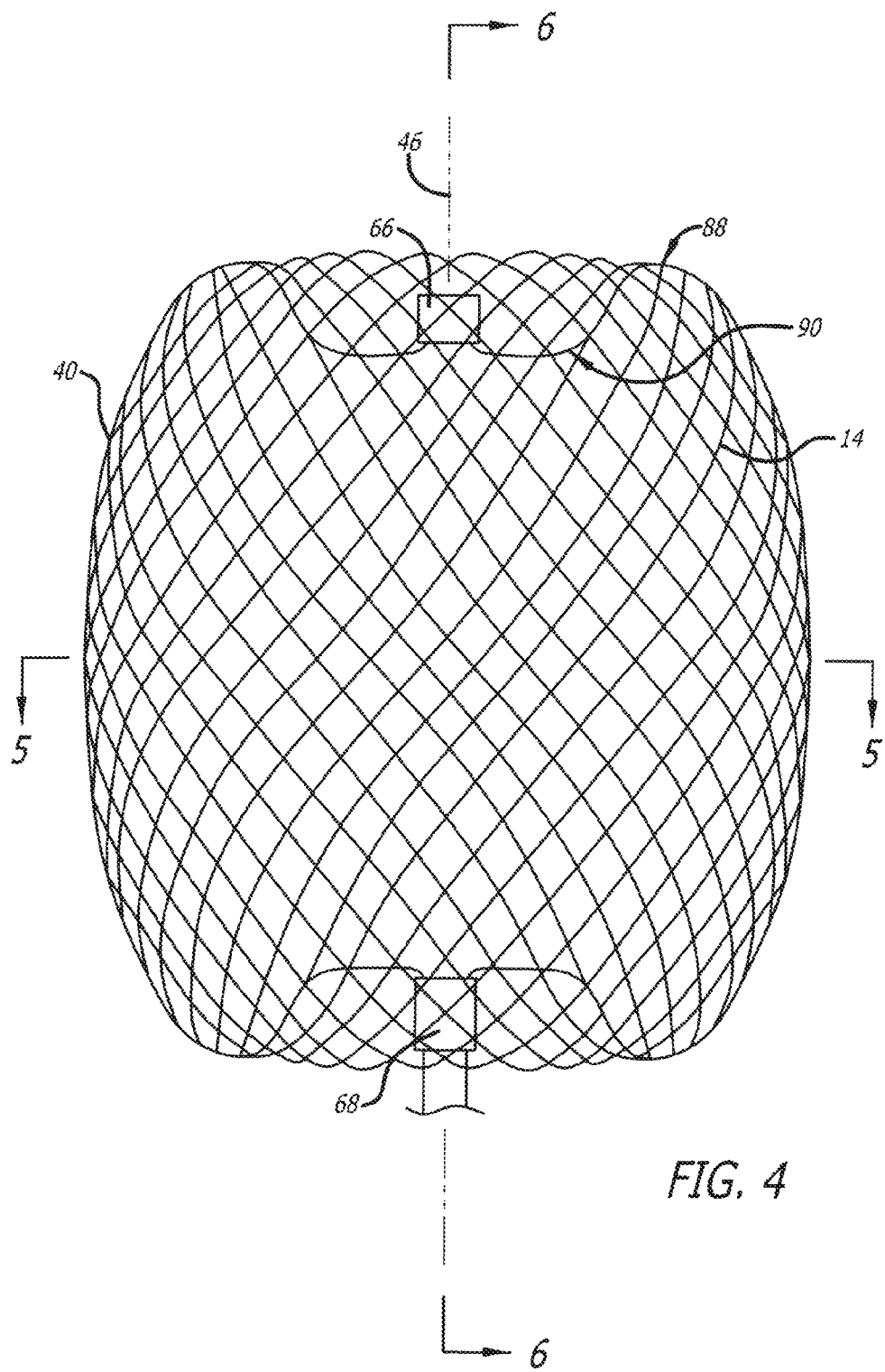
FIG. 4 is an elevation view of the device for treatment of a patient's vasculature of FIG. 3.
Figure 5:
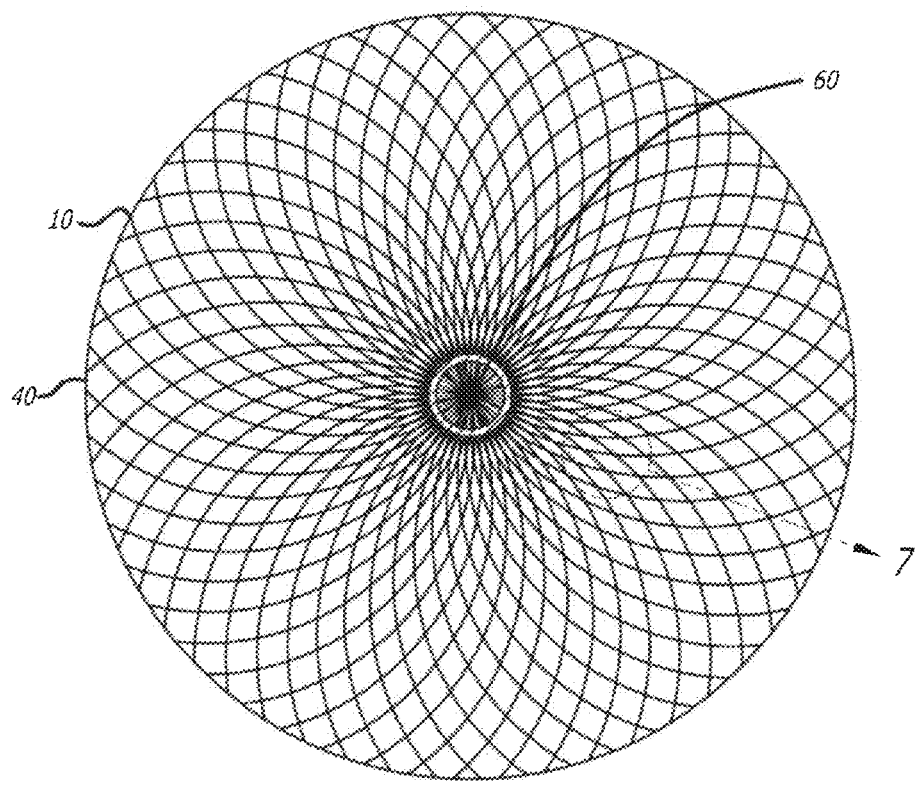
FIG. 5 is a transverse cross sectional view of the device of FIG. 4 taken along lines 5-5 in FIG. 4.

Proximal ends 60 of at least some of the filaments 14 of the permeable shell 40 may be secured to the proximal hub 68 and distal ends 62 of at least some of the filaments 14 of the permeable shell 40 are secured to the distal hub 66, with the proximal hub 68 and distal hub 66 being disposed substantially concentric to the longitudinal axis 46 as shown in FIG. 4. The ends of the filaments 14 may be secured to the respective hubs 66 and 68 by any of the methods discussed above with respect to securement of the filament ends to each other, including the use of adhesives, solder, welding and the like. In some cases, hubs may be made from a highly radiopaque material such as platinum, platinum alloy (e.g., 90% platinum/10% iridium), or gold. A middle portion 30 of the permeable shell 40 may have a first transverse dimension with a low profile suitable for delivery from a microcatheter as shown in FIG. 11. Radial constraint on the device 10 may be applied by an inside surface of the inner lumen of a microcatheter, such as the distal end portion of the microcatheter 61 shown, or it may be applied by any other suitable mechanism that may be released in a controllable manner upon ejection of the device 10 from the distal end of the catheter. In FIG. 11 a proximal end or hub 68 of the device 10 is secured to a distal end of an elongate delivery apparatus 110 of a delivery system 112 disposed at the proximal hub 68 of the device 10.

Some device embodiments 10 having a braided or woven filamentary structure may be formed using about 10 filaments to about 300 filaments 14, more specifically, about 10 filaments to about 100 filaments 14, and even more specifically, about 60 filaments to about 80 filaments 14. Some embodiments of a permeable shell 40 may include about 70 filaments to about 300 filaments extending from the proximal end 32 to the distal end 34, more specifically, about 100 filaments to about 200 filaments extending from the proximal end 32 to the distal end 34. For some embodiments, the filaments 14 may have a transverse dimension or diameter of about 0.0008 inches to about 0.004 inches. The elongate resilient filaments 14 in some cases may have an outer transverse dimension or diameter of about 0.0005 inch to about 0.005 inch, more specifically, about 0.001 inch to about 0.003 inch, and in some cases about 0.0004 inches to about 0.002 inches. For some device embodiments 10 that include filaments 14 of different sizes, the large filaments 48 of the permeable shell 40 may have a transverse dimension or diameter that is about 0.001 inches to about 0.004 inches and the small filaments 50 may have a transverse dimension or diameter of about 0.0004 inches to about 0.0015 inches, more specifically, about 0.0004 inches to about 0.001 inches. In addition, a difference in transverse dimension or diameter between the small filaments 50 and the large filaments 48 may be less than about 0.004 inches, more specifically, less than about 0.0035 inches, and even more specifically, less than about 0.002 inches. For embodiments of permeable shells 40 that include filaments 14 of different sizes, the number of small filaments 50 of the permeable shell 40 relative to the number of large filaments 48 of the permeable shell 40 may be about 2 to 1 to about 15 to 1, more specifically, about 2 to 1 to about 12 to 1, and even more specifically, about 4 to 1 to about 8 to 1.

The expanded relaxed state of the permeable shell 40, as shown in FIG. 4, has an axially shortened configuration relative to the constrained state such that the proximal hub 68 is disposed closer to the distal hub 66 than in the constrained state. Both hubs 66 and 68 are disposed substantially concentric to the longitudinal axis 46 of the device, and each filamentary element 14 forms a smooth arc between the proximal and distal hubs 66 and 68 with a reverse bend at each end. A longitudinal spacing between the proximal and distal hubs 66 and 68 of the permeable shell 40 in a deployed relaxed state may be about 25 percent to about 75 percent of the longitudinal spacing between the proximal and distal hubs 66 and 68 in the constrained cylindrical state, for some embodiments. The arc of the filaments 14 between the proximal and distal ends 32 and 34 may be configured such that a middle portion of each filament 14 has a second transverse dimension substantially greater than the first transverse dimension.

For some embodiments, the permeable shell 40 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the permeable shell 40 in an expanded state may be about 2 times to about 150 times the first transverse dimension, more specifically, about 10 times to about 25 times the first or constrained transverse dimension. A longitudinal spacing between the proximal end 32 and distal end 34 of the permeable shell 40 in the relaxed expanded state may be about 25% percent to about 75% percent of the spacing between the proximal end 32 and distal end 34 in the constrained cylindrical state. For some embodiments, a major transverse dimension of the permeable shell 40 in a relaxed expanded state may be about 4 mm to about 30 mm, more specifically, about 9 mm to about 15 mm, and even more specifically, about 4 mm to about 8 mm.

Figure 6:
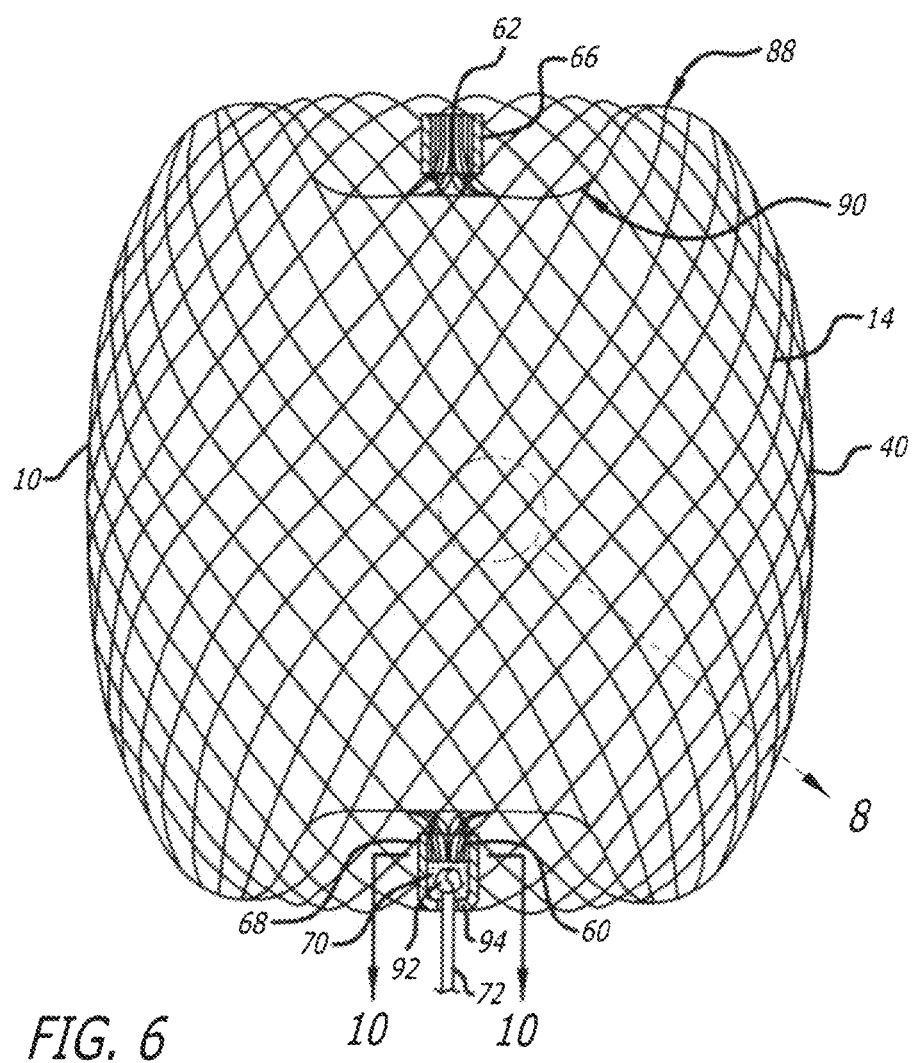
FIG. 6 shows the device of FIG. 4 in longitudinal section taken along lines 6-6 in FIG. 4.

An arced portion of the filaments 14 of the permeable shell 40 may have a sinusoidal-like shape with a first or outer radius 88 and a second or inner radius 90 near the ends of the permeable shell 40 as shown in FIG. 6. This sinusoid-like or multiple curve shape may provide a concavity in the proximal end 32 that may reduce an obstruction of flow in a parent vessel adjacent a vascular defect. For some embodiments, the first radius 88 and second radius 90 of the permeable shell 40 may be between about 0.12 mm to about 3 mm. For some embodiments, the distance between the proximal end 32 and distal end 34 may be less than about 60% of the overall length of the permeable shell 40 for some embodiments. Such a configuration may allow for the distal end 34 to flex downward toward the proximal end 32 when the device 10 meets resistance at the distal end 34 and thus may provide longitudinal conformance. The filaments 14 may be shaped in some embodiments such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. For some embodiments, one of the ends 32 or 34 may be retracted or everted to a greater extent than the other so as to be more longitudinally or axially conformal than the other end.

The first radius 88 and second radius 90 of the permeable shell 40 may be between about 0.12 mm to about 3 mm for some embodiments. For some embodiments, the distance between the proximal end 32 and distal end 34 may be more than about 60% of the overall length of the expanded permeable shell 40. Thus, the largest longitudinal distance between the inner surfaces may be about 60% to about 90% of the longitudinal length of the outer surfaces or the overall length of device 10. A gap between the hubs 66 and 68 at the proximal end 32 and distal end 34 may allow for the distal hub 66 to flex downward toward the proximal hub 68 when the device 10 meets resistance at the distal end and thus provides longitudinal conformance. The filaments 14 may be shaped such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. The distal end 34 may be retracted or everted to a greater extent than the proximal end 32 such that the distal end portion of the permeable shell 40 may be more radially conformal than the proximal end portion. Conformability of a distal end portion may provide better device conformance to irregular shaped aneurysms or other vascular defects. A convex surface of the device may flex inward forming a concave surface to conform to curvature of a vascular site.

Figure 10:
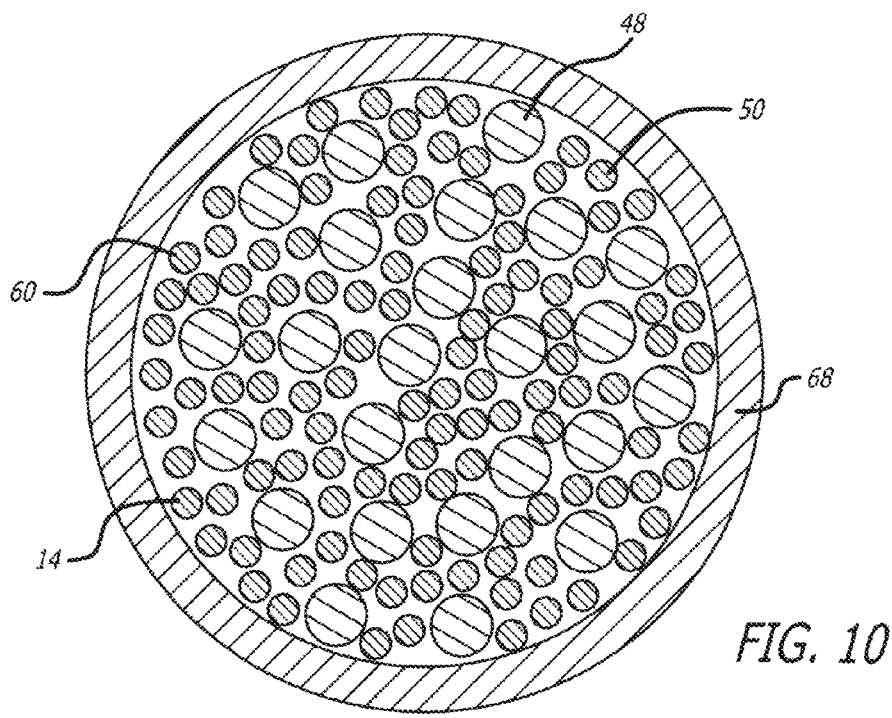
FIG. 10 is a transverse sectional view of a proximal hub portion of the device in FIG. 6 indicated by lines 10-10 in FIG. 6.
Figure 11:
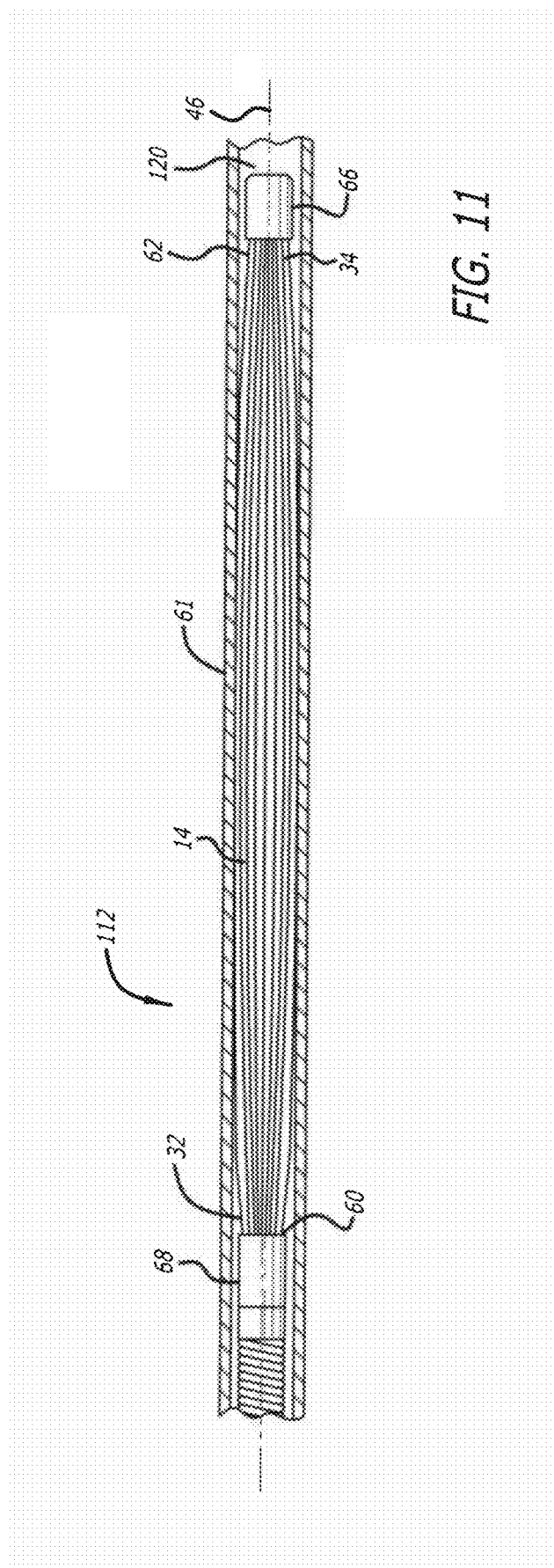
FIG. 11 is an elevation view in partial section of a distal end of a delivery catheter with the device for treatment of a patient's vasculature of FIG. 3 disposed therein in a collapsed constrained state.

FIG. 10 shows an enlarged view of the filaments 14 disposed within a proximal hub 68 of the device 10 with the filaments 14 of two different sizes constrained and tightly packed by an outer ring of the proximal hub 68. The tether member 72 may optionally be disposed within a middle portion of the filaments 14 or within the cavity 70 of the proximal hub 68 proximal of the proximal ends 60 of the filaments 14 as shown in FIG. 6. The distal end of the tether 72 may be secured with a knot 92 formed in the distal end thereof which is mechanically captured in the cavity 70 of the proximal hub 68 formed by a proximal shoulder portion 94 of the proximal hub 68. The knotted distal end 92 of the tether 72 may also be secured by bonding or potting of the distal end of the tether 72 within the cavity 70 and optionally amongst the proximal ends 60 of the filaments 14 with mechanical compression, adhesive bonding, welding, soldering, brazing or the like. The tether embodiment 72 shown in FIG. 6 has a knotted distal end 92 potted in the cavity of the proximal hub 68 with an adhesive. Such a tether 72 may be a dissolvable, severable or releasable tether that may be part of a delivery apparatus 110 used to deploy the device 10 as shown in FIG. 11 and FIGS. 23-26. FIG. 10 also shows the large filaments 48 and small filaments 50 disposed within and constrained by the proximal hub 68 that may be configured to secure the large and small filaments 48 and 50 in place relative to each other within the outer ring of the proximal hub 68.

Figure 7:
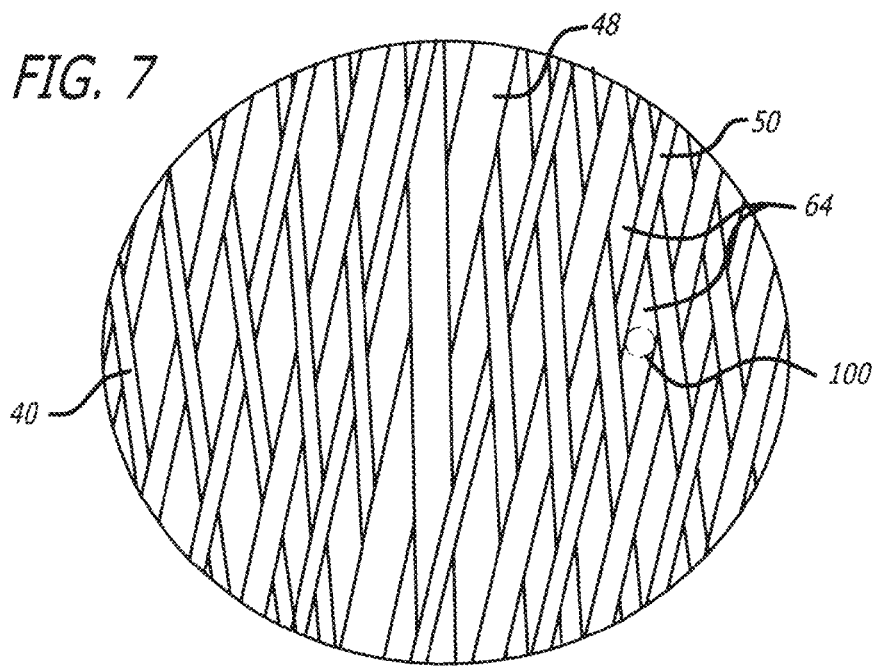
FIG. 7 is an enlarged view of the woven filament structure taken from the encircled portion 7 shown in FIG. 5.
Figure 8:
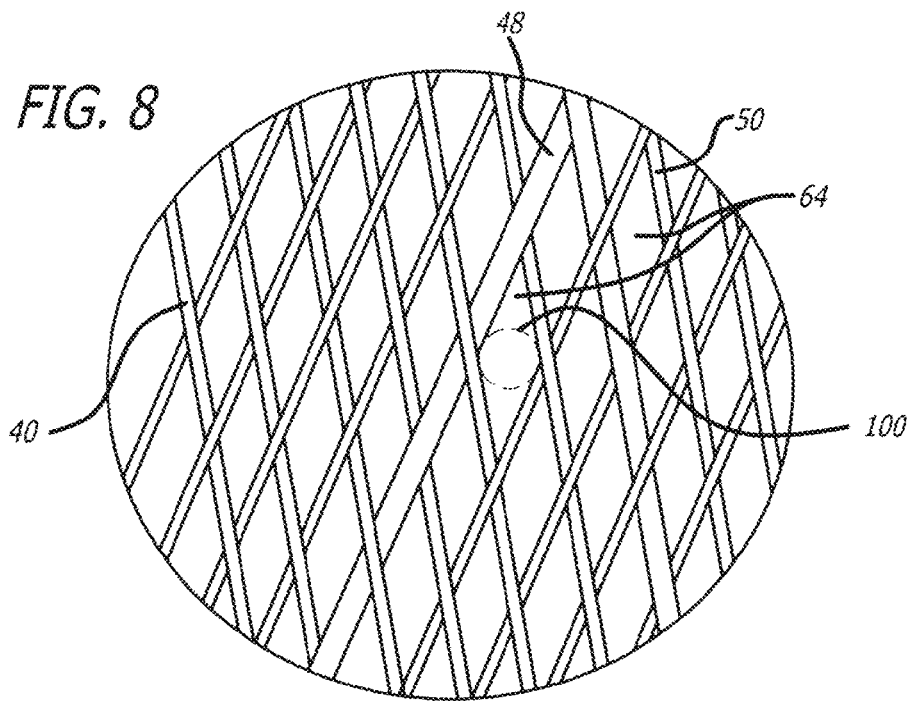
FIG. 8 is an enlarged view of the woven filament structure taken from the encircled portion 8 shown in FIG. 6.
Figure 9:
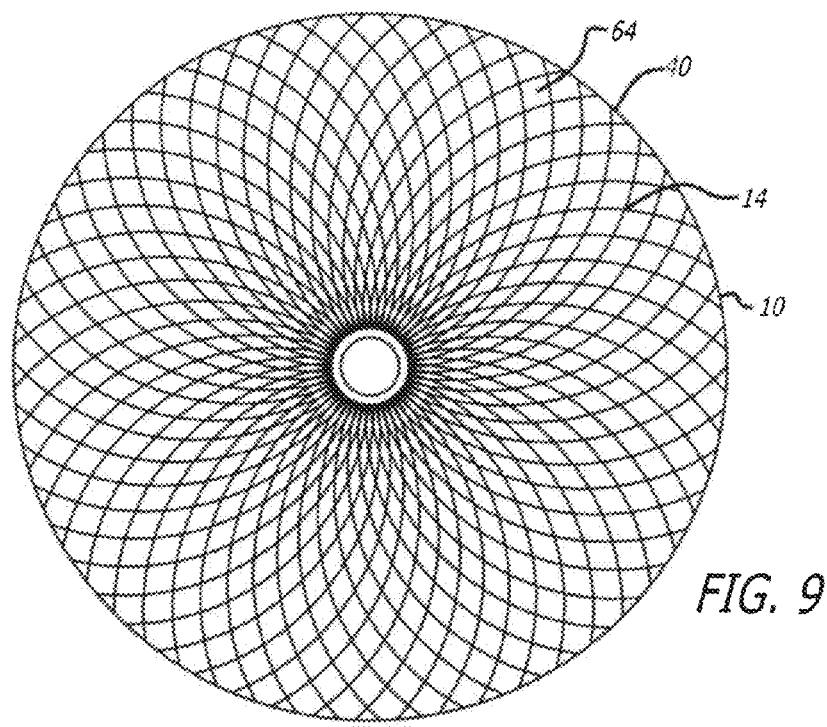
FIG. 9 is a proximal end view of the device of FIG. 3.

FIGS. 7 and 8 illustrate some configuration embodiments of braided filaments 14 of a permeable shell 40 of the device 10 for treatment of a patient's vasculature. The braid structure in each embodiment is shown with a circular shape 100 disposed within a pore 64 of a woven or braided structure with the circular shape 100 making contact with each adjacent filament segment. The pore opening size may be determined at least in part by the size of the filament elements 14 of the braid, the angle overlapping filaments make relative to each other and the picks per inch of the braid structure. For some embodiments, the cells or openings 64 may have an elongated substantially diamond shape as shown in FIG. 7, and the pores or openings 64 of the permeable shell 40 may have a substantially more square shape toward a middle portion 30 of the device 10, as shown in FIG. 8. The diamond shaped pores or openings 64 may have a length substantially greater than the width particularly near the hubs 66 and 68. In some embodiments, the ratio of diamond shaped pore or opening length to width may exceed a ratio of 3 to 1 for some cells. The diamond-shaped openings 64 may have lengths greater than the width thus having an aspect ratio, defined as Length/Width of greater than 1. The openings 64 near the hubs 66 and 68 may have substantially larger aspect ratios than those farther from the hubs as shown in FIG. 7. The aspect ratio of openings 64 adjacent the hubs may be greater than about 4 to 1. The aspect ratio of openings 64 near the largest diameter may be between about 0.75 to 1 and about 2 to 1 for some embodiments. For some embodiments, the aspect ratio of the openings 64 in the permeable shell 40 may be about 0.5 to 1 to about 2 to 1.

The pore size defined by the largest circular shapes 100 that may be disposed within openings 64 of the braided structure of the permeable shell 40 without displacing or distorting the filaments 14 surrounding the opening 64 may range in size from about 0.005 inches to about 0.01 inches, more specifically, about 0.006 inches to about 0.009 inches, even more specifically, about 0.007 inches to about 0.008 inches for some embodiments. In addition, at least some of the openings 64 formed between adjacent filaments 14 of the permeable shell 40 of the device 10 may be configured to allow blood flow through the openings 64 only at a velocity below a thrombotic threshold velocity. For some embodiments, the largest openings 64 in the permeable shell structure 40 may be configured to allow blood flow through the openings 64 only at a velocity below a thrombotic threshold velocity. As discussed above, the pore size may be less than about 0.016 inches, more specifically, less than about 0.012 inches for some embodiments. For some embodiments, the openings 64 formed between adjacent filaments 14 may be about 0.005 inches to about 0.04 inches.

Referring to FIGS. 12-15, a delivery apparatus embodiment 110 of the delivery system 112 of FIG. 11 is shown in more detail. The apparatus 110 includes an elongate core wire 114 that extends from a proximal end 116 of the apparatus 110 to a distal section 118 of the apparatus 110 as shown in FIG. 12. The core wire 114 is configured to provide sufficient column strength to push a constrained device 10 for treatment of a patient's vasculature through an inner lumen 120 of the microcatheter 61 of the delivery system 112 as shown in FIG. 11. The core wire 114 also has sufficient tensile strength to withdraw or proximally retract the device 10 from a position outside the microcatheter 61 and axially within the inner lumen 120 of the microcatheter 61. The tether 72 that extends proximally from the proximal hub 68 is secured to the distal end of the core wire 114 with a length of shrinkable tubing 122 that is disposed over a portion of the tether 72 and a distal section of the core wire 114 and shrunk over both as shown in FIG. 13, although any other suitable means of securement may be used.

A heater coil 124 electrically coupled to a first conductor 126 and a second conductor 128 is disposed over a distal most portion of the tether 72. The heater coil 124 may also be covered with a length of polymer tubing 130 disposed over the heater coil 124 distal of the heat shrink tubing 122 that serves to act as a heat shield and minimizes the leakage of heat from the heater coil 124 into the environment, such as the patient's blood stream, around the delivery apparatus 110. Once the heat shrink tubing 122 and insulating polymer tubing 130 have been secured to the distal section 118 of the apparatus 110, the proximal portion of the tether 72 disposed proximal of the heat shrink tubing 122 may be trimmed as shown in FIG. 13. An over coil 132 that extends from a distal end 134 of the delivery apparatus 110 to a proximal section 136 of the apparatus 110 may then be disposed over the heater coil 124, core wire 114, tether 72, first conductor 126 and second conductor 128 to hold these elements together, produce a low friction outer surface and maintain a desired flexibility of the delivery apparatus 110. The proximal section 136 of the apparatus 110 includes the proximal terminus of the over coil 132 which is disposed distal of a first contact 138 and second contact 140 which are circumferentially disposed about the proximal section 136 of the core wire 114, insulated therefrom, and electrically coupled to the first conductor 126 and second conductor 128, respectively as shown in FIG. 15.

The heater coil 124 may be configured to receive electric current supplied through the first conductor 126 and second conductor 128 from an electrical energy source 142 coupled to the first contact 138 and second contact 140 at the proximal section 136 of the apparatus 110. The electrical current passed through the heater coil 124 heats the heater coil to a temperature above the melting point of the tether material 72 so as to melt the tether 72 and sever it upon deployment of the device 10.

Embodiments of the delivery apparatus 110 may generally have a length greater than the overall length of a microcatheter 61 to be used for the delivery system 112. This relationship allows the delivery apparatus 110 to extend, along with the device 10 secured to the distal end thereof, from the distal port of the inner lumen 120 of the microcatheter 61 while having sufficient length extending from a proximal end 150 of the microcatheter 61, shown in FIG. 17 discussed below, to enable manipulation thereof by a physician. For some embodiments, the length of the delivery apparatus 110 may be about 170 cm to about 200 cm. The core wire 114 may be made from any suitable high strength material such as stainless steel, NiTi alloy, or the like. Embodiments of the core wire 114 may have an outer diameter or transverse dimension of about 0.010 inch to about 0.015 inch. The over coil 132 may have an outer diameter or transverse dimension of about 0.018 inch to about 0.03 inch. Although the apparatus embodiment 110 shown in FIGS. 12-15 is activated by electrical energy passed through a conductor pair, a similar configuration that utilizes light energy passed through a fiber optic or any other suitable arrangement could be used to remotely heat a distal heating member or element such as the heater coil 124 to sever the distal portion of the tether 72. In addition, other delivery apparatus embodiments are discussed and incorporated herein that may also be used for any of the device embodiments 10 for treatment of a patient's vasculature discussed herein.

Other delivery and positioning system embodiments may provide for the ability to rotate a device for treatment of a patient's vasculature in-vivo without translating torque along the entire length of the delivery apparatus. Some embodiments for delivery and positioning of devices 10 are described in co-owned International Application No. PCT/US2008/065694, which is incorporated by reference in its entirety. The delivery and positioning apparatus may include a distal rotating member that allows rotational positioning of the device. The delivery and positioning apparatus may include a distal rotating member that rotates an implant in vivo without the transmission of torque along the entire length of the apparatus. Optionally, delivery system may also rotate the implant without the transmission of torque in the intermediate portion between the proximal end and the distal rotatable end. The delivery and positioning apparatus may be releasably secured to any suitable portion of the device for treatment of a patient's vasculature.

Device embodiments discussed herein may be releasable from any suitable flexible, elongate delivery apparatus or actuator such as a guidewire or guidewire-like structure. The release of device embodiments from such a delivery apparatus may be activated by a thermal mechanism, as discussed above, electrolytic mechanism, hydraulic mechanism, shape memory material mechanism, or any other mechanism known in the art of endovascular implant deployment.

Embodiments for deployment and release of therapeutic devices, such as deployment of embolic devices or stents within the vasculature of a patient, may include connecting such a device via a releasable connection to a distal portion of a pusher or other delivery apparatus member. The therapeutic device 10 may be detachably mounted to the distal portion of the apparatus by a filamentary tether 72, string, thread, wire, suture, fiber, or the like, which may be referred to above as the tether. The tether 72 may be in the form of a monofilament, rod, ribbon, hollow tube, or the like. Some embodiments of the tether may have a diameter or maximum thickness of between about 0.05 mm and 0.2 mm. The tether 72 may be configured to be able to withstand a maximum tensile load of between about 0.5 kg and 5 kg. For some embodiments, due to the mass of the device 10 being deployed which may be substantially greater than some embolic devices, some known detachment devices may lack sufficient tensile strength to be used for some embodiments discussed herein. As such, it may be desirable to use small very high strength fibers for some tether embodiments having a "load at break" greater than about 15 Newtons. For some embodiments, a tether made from a material known as Dyneema Purity available from Royal DSM, Heerlen, Netherlands may be used.

The tether 72 may be severed by the input of energy such as electric current to a heating element causing release of the therapeutic device. For some embodiments, the heating element may be a coil of wire with high electrical resistivity such as a platinum-tungsten alloy. The tether member may pass through or be positioned adjacent the heater element. The heater may be contained substantially within the distal portion of the delivery apparatus to provide thermal insulation to reduce the potential for thermal damage to the surrounding tissues during detachment. In another embodiment, current may pass through the tether that also acts as a heating element.

Many materials may be used to make tether embodiments 72 including polymers, metals and composites thereof. One class of materials that may be useful for tethers includes polymers such as polyolefin, polyolefin elastomer such as polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials that may be used for tether embodiment may include metals such as nickel titanium alloy (Nitinol), gold, platinum, tantalum and steel. Other materials that may be useful for tether construction includes wholly aromatic polyester polymers which are liquid crystal polymers (LCP) that may provide high performance properties and are highly inert. A commercially available LCP polymer is Vectran, which is produced by Kuraray Co. (Tokyo, Japan). The selection of the material may depend on the melting or softening temperature, the power used for detachment, and the body treatment site. The tether may be joined to the implant and/or the pusher by crimping, welding, knot tying, soldering, adhesive bonding, or other means known in the art.

Figure 16:
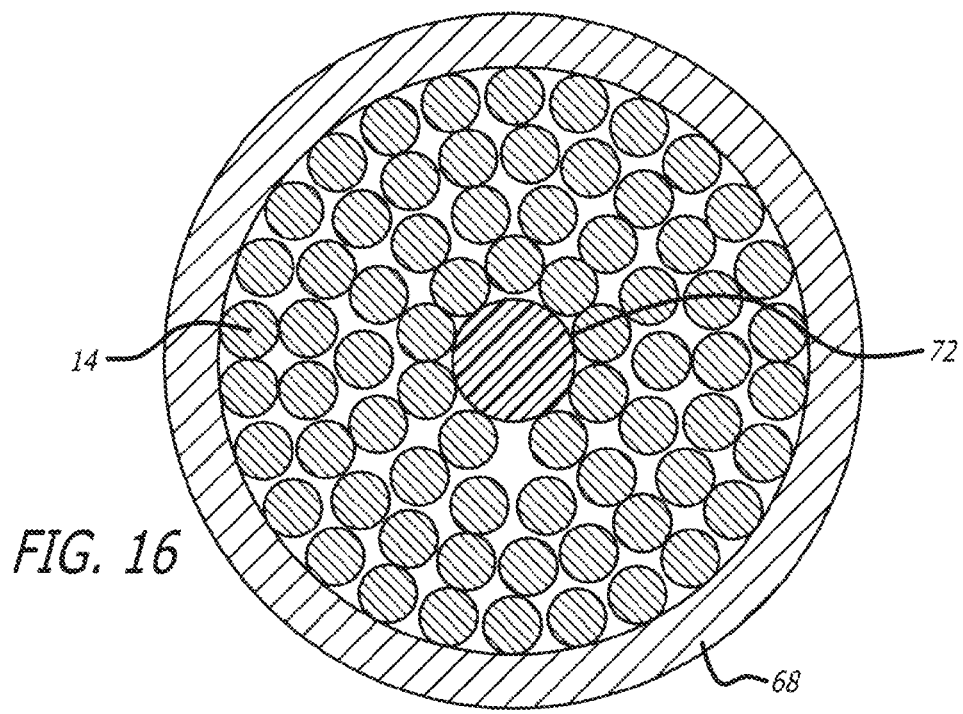
FIG. 16 illustrates an embodiment of a filament configuration for a device for treatment of a patient's vasculature.

It should be noted also that many variations of filament and proximal hub construction such as is detailed above with regard to FIG. 10 may be used for useful embodiments of a device for treatment of a patient's vasculature 10. FIG. 16 shows an enlarged view in transverse cross section of a proximal hub configuration. For the embodiment shown, the filaments 14 are disposed within a proximal hub 68 or end portion of the device 10 with the filaments 14 constrained and tightly packed by an outer ring of the proximal hub 68. A tether member 72 may be disposed within a middle portion of the filaments 14 or within a cavity of the proximal hub 68 proximal of the proximal ends 60 of the filaments 14. Such a tether 72 may be a dissolvable, severable or releasable tether that may be part of a release apparatus as discussed above used to deploy the device.

FIG. 16 illustrates in transverse cross section an embodiment of a proximal hub 68 showing the configuration of filaments which may be tightly packed and radially constrained by an inside surface of the proximal hub 68. In some embodiments, the braided or woven structure of the permeable shell 40 formed from such filaments 14 may be constructed using a large number of small filaments. The number of filaments 14 may be greater than 125 and may also be between about 80 filaments and about 180 filaments. As discussed above, the total number of filaments 14 for some embodiments may be about 70 filaments to about 300 filaments, more specifically, about 100 filaments to about 200 filaments. In some embodiments, the braided structure of the permeable shell 40 may be constructed with two or more sizes of filaments 14. For example, the structure may have several larger filaments that provide structural support and several smaller filaments that provide the desired pore size and density and thus flow resistance to achieve a thrombotic threshold velocity in some cases. For some embodiments, small filaments 50 of the permeable shell 40 may have a transverse dimension or diameter of about 0.0006 inches to about 0.002 inches for some embodiments and about 0.0004 inches to about 0.001 inches in other embodiments. The large filaments 48 may have a transverse dimension or diameter of about 0.0015 inches to about 0.004 inches in some embodiments and about 0.001 inches to about 0.004 inches in other embodiments. The filaments 14 may be braided in a plain weave that is one under, one over structure (shown in FIGS. 7 and 8) or a supplementary weave; more than one warp interlace with one or more than one weft. The pick count may be varied between about 25 and 200 picks per inch (PPI).

For some embodiments, the permeable shell 40 or portions thereof may be porous and may be highly permeable to liquids. In contrast to most vascular prosthesis fabrics or grafts which typically have a water permeability below 2,000 ml/min/cm2 when measured at a pressure of 120 mmHg, the permeable shell 40 of some embodiments discussed herein may have a water permeability greater than about 2,000 ml/min/cm2, in some cases greater than about 2,500 ml/min/cm2. For some embodiments, water permeability of the permeable shell 40 or portions thereof may be between about 2,000 and 10,000 ml/min/cm2, more specifically, about 2,000 ml/min/cm2 to about 15,000 ml/min/cm2, when measured at a pressure of 120 mmHg.

Device embodiments and components thereof may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g., polyethylene terephthalate or PET), PolyEtherEther Ketone (PEEK), polytetrafluoroethylene (PTFE), polycarbonate urethane (PCU) and polyurethane (PU). Device embodiments may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable (e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable, bioabsorbable polymer. Potentially suitable bioabsorbable materials include polylactic acid (PLA), poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials. An absorbable composite fiber may be made by combining a reinforcement fiber made from a copolymer of about 18% glycolic acid and about 82% lactic acid with a matrix material consisting of a blend of the above copolymer with about 20% polycaprolactone (PCL).

In any of the suitable device embodiments 10 discussed herein, the permeable shell structure 40 may include one or more fixation elements or surfaces to facilitate fixation of the device within a blood vessel or other vascular site. The fixation elements may comprise hooks, barbs, protrusions, pores, microfeatures, texturing, bioadhesives or combinations thereof. Embodiments of the support structure may be fabricated from a tube of metal where portions are removed. The removal of material may be done by laser, electrical discharge machining (EDM), photochemical etching and traditional machining techniques. In any of the described embodiments, the support structure may be constructed with a plurality of wires, cut or etched from a sheet of a material, cut or etched from a tube or a combination thereof as in the art of vascular stent fabrication.

Permeable shell embodiments 40 may be formed at least in part of wire, ribbon, or other filamentary elements 14. These filamentary elements 14 may have circular, elliptical, ovoid, square, rectangular, or triangular cross-sections. Permeable shell embodiments 40 may also be formed using conventional machining, laser cutting, electrical discharge machining (EDM) or photochemical machining (PCM). If made of a metal, it may be formed from either metallic tubes or sheet material.

Figure 17:
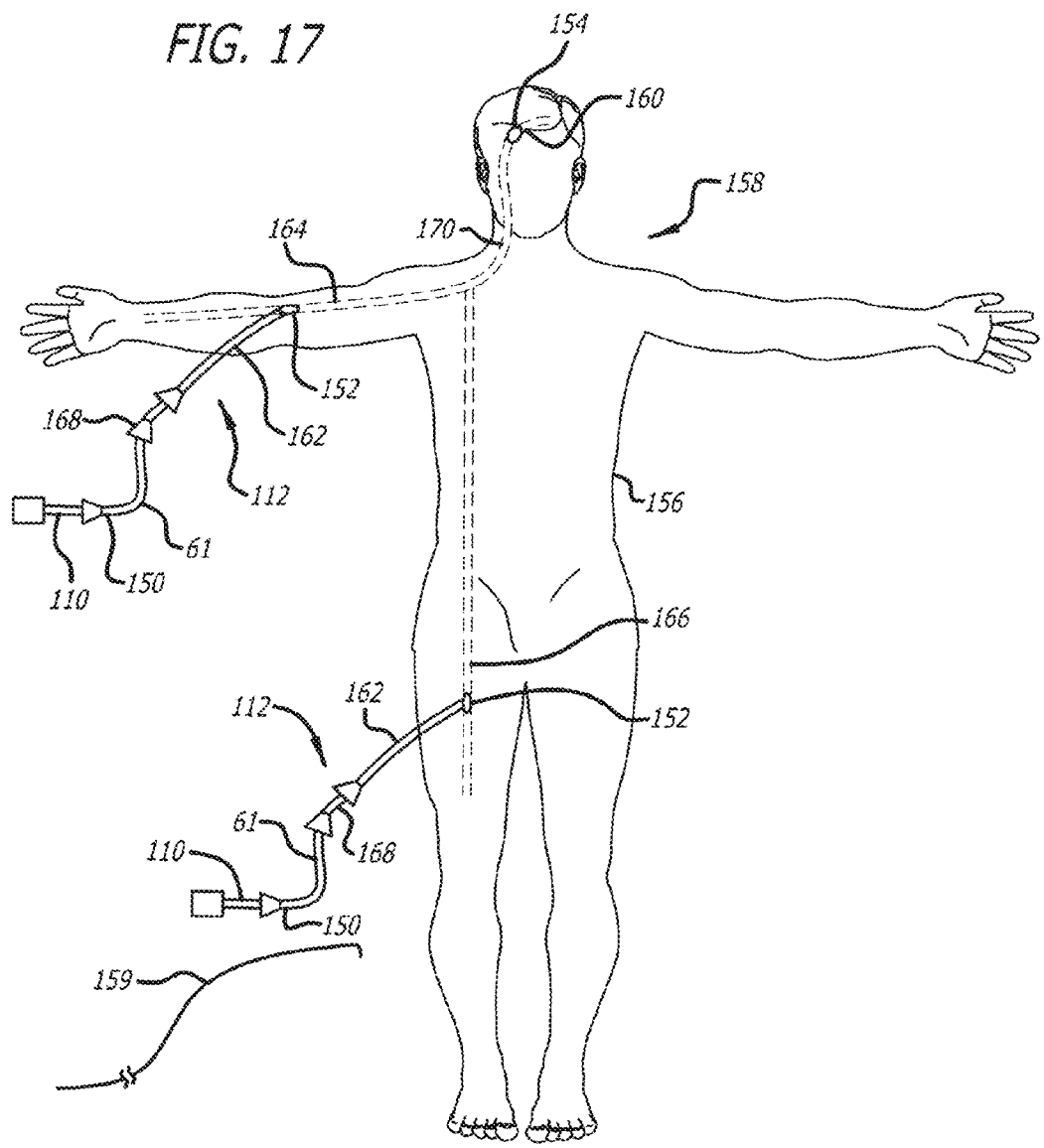
FIG. 17 is a schematic view of a patient being accessed by an introducer sheath, a microcatheter and a device for treatment of a patient's vasculature releasably secured to a distal end of a delivery device or actuator.
Figure 18:
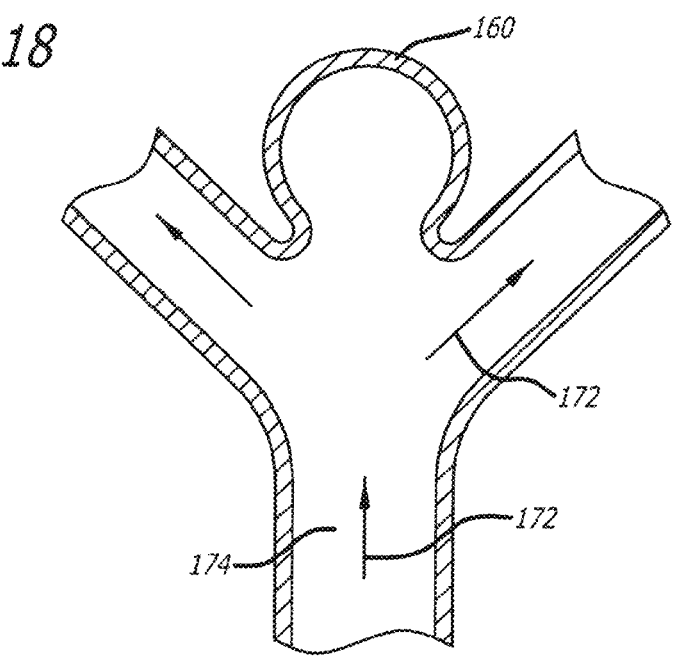
FIG. 18 is a sectional view of a terminal aneurysm.

Device embodiments 10 discussed herein may be delivered and deployed from a delivery and positioning system 112 that includes a microcatheter 61, such as the type of microcatheter 61 that is known in the art of neurovascular navigation and therapy. Device embodiments for treatment of a patient's vasculature 10 may be elastically collapsed and restrained by a tube or other radial restraint, such as an inner lumen 120 of a microcatheter 61, for delivery and deployment. The microcatheter 61 may generally be inserted through a small incision 152 accessing a peripheral blood vessel such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the device 10 secured to a delivery apparatus 110 of the delivery system 112 through the inner lumen 120 of a microcatheter 61 in some cases. FIG. 17 illustrates a schematic view of a patient 158 undergoing treatment of a vascular defect 160 as shown in FIG. 18. An access sheath 162 is shown disposed within either a radial artery 164 or femoral artery 166 of the patient 158 with a delivery system 112 that includes a microcatheter 61 and delivery apparatus 110 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, and the like in order to achieve percutaneous access to a vascular defect 160. In general, the patient 158 may be prepared for surgery and the access artery is exposed via a small surgical incision 152 and access to the lumen is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use include the Synchro2® made by Boston Scientific and the Glidewire Gold Neuro® made by MicroVention Terumo. Typical guidewire sizes may include 0.014 inches and 0.018 inches. Once the distal end 151 of the catheter 61 is positioned at the site, often by locating its distal end through the use of radiopaque marker material and fluoroscopy, the catheter is cleared. For example, if a guidewire 159 has been used to position the microcatheter 61, it is withdrawn from the catheter 61 and then the implant delivery apparatus 110 is advanced through the microcatheter 61.

Delivery and deployment of device embodiments 10 discussed herein may be carried out by first compressing the device 10 to a radially constrained and longitudinally flexible state as shown in FIG. 11. The device 10 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The device 10 secured to a suitable delivery apparatus 110 may then be radially constrained, inserted into a proximal portion of the inner lumen 120 of the microcatheter 61 and distally advanced to the vascular defect 160 through the inner lumen 120.

Once disposed within the vascular defect 160, the device 10 may then allowed to assume an expanded relaxed or partially relaxed state with the permeable shell 40 of the device spanning or partially spanning a portion of the vascular defect 160 or the entire vascular defect 160. The device 10 may also be activated by the application of an energy source to assume an expanded deployed configuration once ejected from the distal section of the microcatheter 61 for some embodiments. Once the device 10 is deployed at a desired treatment site 154, the microcatheter 61 may then be withdrawn.

Figure 19:
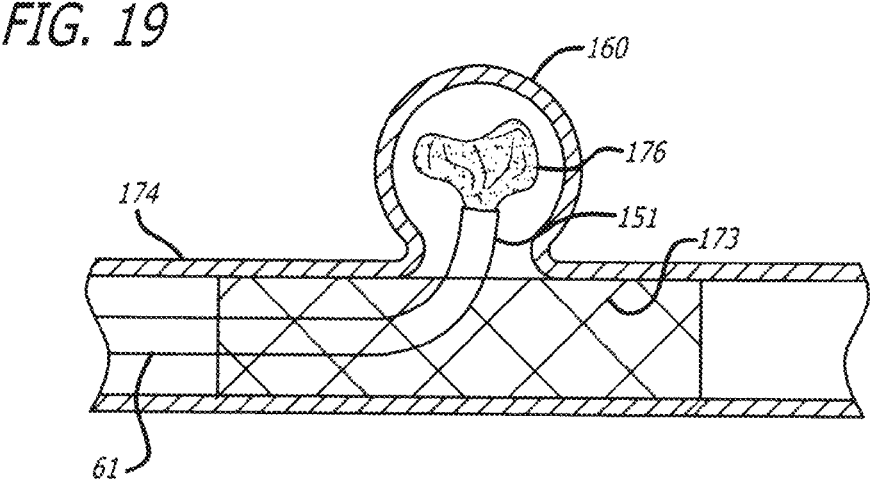
FIG. 19 is a sectional view of an aneurysm.

Some embodiments of devices for the treatment of a patient's vasculature 10 discussed herein may be directed to the treatment of specific types of defects of a patient's vasculature. For example, referring to FIG. 18, an aneurysm 160 commonly referred to as a terminal aneurysm is shown in section. Terminal aneurysms occur typically at bifurcations in a patient's vasculature where blood flow, indicated by the arrows 172, from a supply vessel splits into two or more branch vessels directed away from each other. The main flow of blood from the supply vessel 174, such as a basilar artery, sometimes impinges on the vessel where the vessel diverges and where the aneurysm sack forms. Terminal aneurysms may have a well-defined neck structure where the profile of the aneurysm 160 narrows adjacent the nominal vessel profile, but other terminal aneurysm embodiments may have a less defined neck structure or no neck structure. FIG. 19 illustrates a typical berry type aneurysm 160 in section where a portion of a wall of a nominal vessel section weakens and expands into a sack like structure ballooning away from the nominal vessel surface and profile. Some berry type aneurysms may have a well-defined neck structure as shown in FIG. 19, but others may have a less defined neck structure or none at all. FIG. 19 also shows some optional procedures wherein a stent 173 or other type of support has been deployed in the parent vessel 174 adjacent the aneurysm. Also, shown is embolic material 176 being deposited into the aneurysm 160 through a microcatheter 61. Either or both of the stent 173 and embolic material 176 may be so deplored either before or after the deployment of a device for treatment of a patient's vasculature 10.

Figure 28:
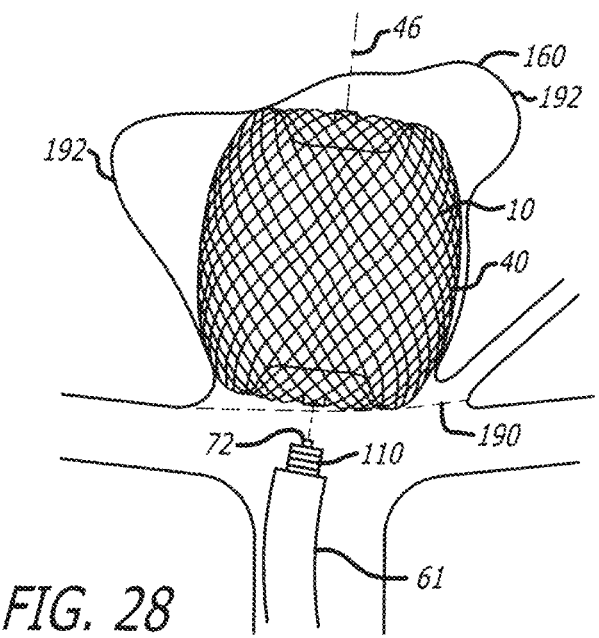
FIG. 28 is an elevation view in partial section of an embodiment of a device for treatment of a patient's vasculature deployed within an irregularly shaped aneurysm.

Prior to delivery and deployment of a device for treatment of a patient's vasculature 10, it may be desirable for the treating physician to choose an appropriately sized device 10 to optimize the treatment results. Some embodiments of treatment may include estimating a volume of a vascular site or defect 160 to be treated and selecting a device 10 with a volume that is substantially the same volume or slightly over-sized relative to the volume of the vascular site or defect 160. The volume of the vascular defect 160 to be occluded may be determined using three-dimensional angiography or other similar imaging techniques along with software that calculates the volume of a selected region. The amount of over-sizing may be between about 2% and 15% of the measured volume. In some embodiments, such as a very irregular shaped aneurysm, it may be desirable to under-size the volume of the device 10. Small lobes or "daughter aneurysms" may be excluded from the volume, defining a truncated volume that may be only partially filled by the device without affecting the outcome. A device 10 deployed within such an irregularly shaped aneurysm 160 is shown in FIG. 28 discussed below. Such a method embodiment may also include implanting or deploying the device 10 so that the vascular defect 160 is substantially filled volumetrically by a combination of device and blood contained therein. The device 10 may be configured to be sufficiently conformal to adapt to irregular shaped vascular defects 160 so that at least about 75%, in some cases about 80%, of the vascular defect volume is occluded by a combination of device 10 and blood contained therein.

Figure 20:
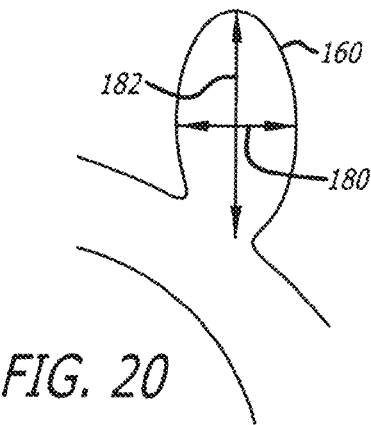
FIG. 20 is a schematic view in section of an aneurysm showing perpendicular arrows that indicate interior nominal longitudinal and transverse dimensions of the aneurysm.
Figure 21:
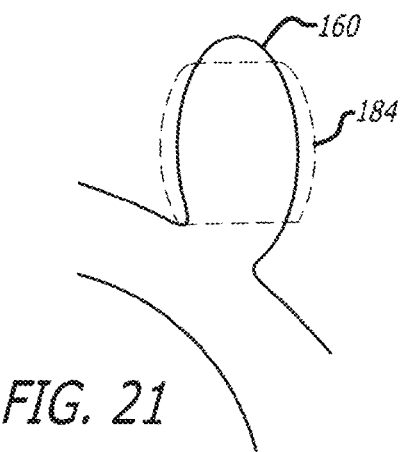
FIG. 21 is a schematic view in section of the aneurysm of FIG. 20 with a dashed outline of a device for treatment of a patient's vasculature in a relaxed unconstrained state that extends transversely outside of the walls of the aneurysm.
Figure 22:
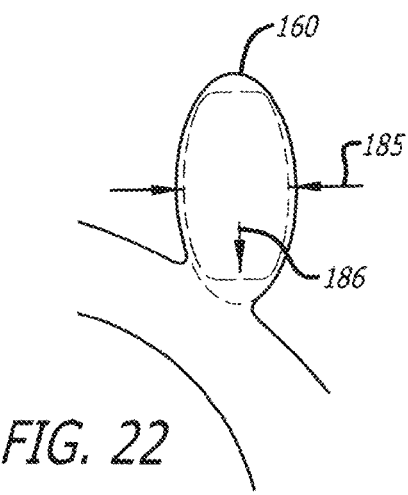
FIG. 22 is a schematic view in section of an outline of a device represented by the dashed line in FIG. 21 in a deployed and partially constrained state within the aneurysm.

In particular, for some treatment embodiments, it may be desirable to choose a device 10 that is properly oversized in a transverse dimension so as to achieve a desired conformance, radial force and fit after deployment of the device 10. FIGS. 20-22 illustrate a schematic representation of how a device 10 may be chosen for a proper fit after deployment that is initially oversized in a transverse dimension by at least about 10% of the largest transverse dimension of the vascular defect 160 and sometimes up to about 100% of the largest transverse dimension. For some embodiments, the device 10 may be oversized a small amount (e.g., less than about 1.5 mm) in relation to measured dimensions for the width, height or neck diameter of the vascular defect 160.

In FIG. 20, a vascular defect 160 in the form of a cerebral aneurysm is shown with horizontal arrows 180 and vertical arrows 182 indicating the approximate largest interior dimensions of the defect 160. Arrow 180 extending horizontally indicates the largest transverse dimension of the defect 160. In FIG. 21, a dashed outline 184 of a device for treatment of the vascular defect 10 is shown superimposed over the vascular defect 160 of FIG. 20 illustrating how a device 10 that has been chosen to be approximately 20% oversized in a transverse dimension would look in its unconstrained, relaxed state. FIG. 22 illustrates how the device 10 which is indicated by the dashed line 184 of FIG. 21 might conform to the interior surface of the vascular defect 160 after deployment whereby the nominal transverse dimension of the device 10 in a relaxed unconstrained state has now been slightly constrained by the inward radial force 185 exerted by the vascular defect 160 on the device 10. In response, as the filaments 14 of the device 10 and thus the permeable shell 40 made therefrom have a constant length, the device 10 has assumed a slightly elongated shape in the axial or longitudinal axis of the device 10 so as to elongate and better fill the interior volume of the defect 160 as indicated by the downward arrow 186 in FIG. 22.

Once a properly sized device 10 has been selected, the delivery and deployment process may then proceed. It should also be noted also that the properties of the device embodiments 10 and delivery system embodiments 112 discussed herein generally allow for retraction of a device 10 after initial deployment into a defect 160, but before detachment of the device 10. Therefore, it may also be possible and desirable to withdraw or retrieve an initially deployed device 10 after the fit within the defect 160 has been evaluated in favor of a differently sized device 10. An example of a terminal aneurysm 160 is shown in FIG. 23 in section. The tip 151 of a catheter, such as a microcatheter 61 may be advanced into or adjacent the vascular site or defect 160 (e.g., aneurysm) as shown in FIG. 24. For some embodiments, an embolic coil or other vaso-occlusive device or material 176 (as shown for example in FIG. 19) may optionally be placed within the aneurysm 160 to provide a framework for receiving the device 10. In addition, a stent 173 may be placed within a parent vessel 174 of some aneurysms substantially crossing the aneurysm neck prior to or during delivery of devices for treatment of a patient's vasculature discussed herein (also as shown for example in FIG. 19). An example of a suitable microcatheter 61 having an inner lumen diameter of about 0.020 inches to about 0.022 inches is the Rapid Transit® manufactured by Cordis Corporation. Examples of some suitable microcatheters 61 may include microcatheters having an inner lumen diameter of about 0.026 inch to about 0.028 inch, such as the Rebar® by Ev3 Company, the Renegade Hi-Flow® by Boston Scientific Corporation, and the Mass Transit® by Cordis Corporation. Suitable microcatheters having an inner lumen diameter of about 0.031 inch to about 0.033 inch may include the Marksmen® by Chestnut Medical Technologies, Inc. and the Vasco 28® by Bait Extrusion. A suitable microcatheter 61 having an inner lumen diameter of about 0.039 inch to about 0.041 inch includes the Vasco 35 by Bait Extrusion. These microcatheters 61 are listed as exemplary embodiments only, other suitable microcatheters may also be used with any of the embodiments discussed herein.

Detachment of the device 10 from the delivery apparatus 110 may be controlled by a control switch 188 disposed at a proximal end of the delivery system 112, which may also be coupled to an energy source 142, which severs the tether 72 that secures the proximal hub 68 of the device 10 to the delivery apparatus 110. While disposed within the microcatheter 61 or other suitable delivery system 112, as shown in FIG. 11, the filaments 14 of the permeable shell 40 may take on an elongated, non-everted configuration substantially parallel to each other and a longitudinal axis of the catheter 61. Once the device 10 is pushed out of the distal port of the microcatheter 61, or the radial constraint is otherwise removed, the distal ends 62 of the filaments 14 may then axially contract towards each other so as to assume the globular everted configuration within the vascular defect 160 as shown in FIG. 25.

The device 10 may be inserted through the microcatheter 61 such that the catheter lumen 120 restrains radial expansion of the device 10 during delivery. Once the distal tip or deployment port of the delivery system 112 is positioned in a desirable location adjacent or within a vascular defect 160, the device 10 may be deployed out the distal end of the catheter 61 thus allowing the device to begin to radially expand as shown in FIG. 25. As the device 10 emerges from the distal end of the delivery system 112, the device 10 expands to an expanded state within the vascular defect 160, but may be at least partially constrained by an interior surface of the vascular defect 160.

Upon full deployment, radial expansion of the device 10 may serve to secure the device 10 within the vascular defect 160 and also deploy the permeable shell 40 across at least a portion of an opening 190 (e.g., aneurysm neck) so as to at least partially isolate the vascular defect 160 from flow, pressure or both of the patient's vasculature adjacent the vascular defect 160 as shown in FIG. 26. The conformability of the device 10, particularly in the neck region 190 may provide for improved sealing. For some embodiments, once deployed, the permeable shell 40 may substantially slow flow of fluids, impede flow into the vascular site, and thus reduce pressure within the vascular defect 160. For some embodiments, the device 10 may be implanted substantially within the vascular defect 160, however, in some embodiments, a portion of the device 10 may extend into the defect opening or neck 190 or into branch vessels.

One exemplary case study that has been conducted includes a procedure performed on a female canine where an aneurysm was surgically created in the subject canine. The target aneurysm prior to treatment had a maximum transverse dimension of about 8 mm, a length of about 10 mm and a neck measurement of about 5.6 mm. The device 10 deployed included a permeable shell 40 formed of 144 resilient filaments having a transverse diameter of about 0.0015 inches braided into a globular structure having a transverse dimension of about 10 mm and a longitudinal length of about 7 mm in a relaxed expanded state. The maximum size 100 of the pores 64 of the expanded deployed permeable shell 40 was about 0.013 inches. The device was delivered to the target aneurysm using a 5 Fr. Guider Softip XF guide catheter made by Boston Scientific. The maximum size 100 of the pores 64 of the portion of the expanded deployed permeable shell 40 that spanned the neck of the aneurysm again was about 0.013 inches. Five minutes after detachment from the delivery system, the device 10 had produced acute occlusion of the aneurysm.

Another exemplary case study conducted involved treatment of a surgically created aneurysm in a New Zealand White Rabbit. The target aneurysm prior to treatment had a maximum transverse dimension of about 3.6 mm, length of about 5.8 mm and a neck measurement of about 3.4 mm. The device 10 deployed included a permeable shell formed of 144 resilient filaments having a transverse diameter of about 0.001 inches braided into a globular structure having a transverse dimension of about 4 mm and a length of about 5 mm in a relaxed expanded state. The pore size 100 of the portion of the braided mesh of the expanded deployed permeable shell 40 that was configured to span the neck of the vascular defect was about 0.005 inches. The device was delivered to the surgically created aneurysm with a 5 Fr. Envoy® STR guide catheter manufactured by Cordis Neurovascular. A Renegade Hi-Flo microcatheter manufactured by Boston Scientific having an inner lumen diameter of about 0.027 inches was then inserted through the guide catheter and served as a conduit for delivery of the device 10 secured to a distal end of a delivery apparatus. Once the device 10 was deployed within the vascular defect 160, the vascular defect 160 achieved at least partial occlusion at 5 minutes from implantation. However, due to the sensitivity of the subject animal to angiographic injection and measurement, no further data was taken during the procedure. Complete occlusion was observed for the device when examined at 3 weeks from the procedure.

For some embodiments, as discussed above, the device 10 may be manipulated by the user to position the device 10 within the vascular site or defect 160 during or after deployment but prior to detachment. For some embodiments, the device 10 may be rotated in order to achieve a desired position of the device 10 and, more specifically, a desired position of the permeable shell 40, prior to or during deployment of the device 10. For some embodiments, the device 10 may be rotated about a longitudinal axis of the delivery system 112 with or without the transmission or manifestation of torque being exhibited along a middle portion of a delivery catheter being used for the delivery. It may be desirable in some circumstances to determine whether acute occlusion of the vascular defect 160 has occurred prior to detachment of the device 10 from the delivery apparatus 110 of the delivery system 112. These delivery and deployment methods may be used for deployment within berry aneurysms, terminal aneurysms, or any other suitable vascular defect embodiments 160. Some method embodiments include deploying the device 10 at a confluence of three vessels of the patient's vasculature that form a bifurcation such that the permeable shell 40 of the device 10 substantially covers the neck of a terminal aneurysm. Once the physician is satisfied with the deployment, size and position of the device 10, the device 10 may then be detached by actuation of the control switch 188 by the methods described above and shown in FIG. 26. Thereafter, the device 10 is in an implanted state within the vascular defect 160 to effect treatment thereof.

Figure 27:
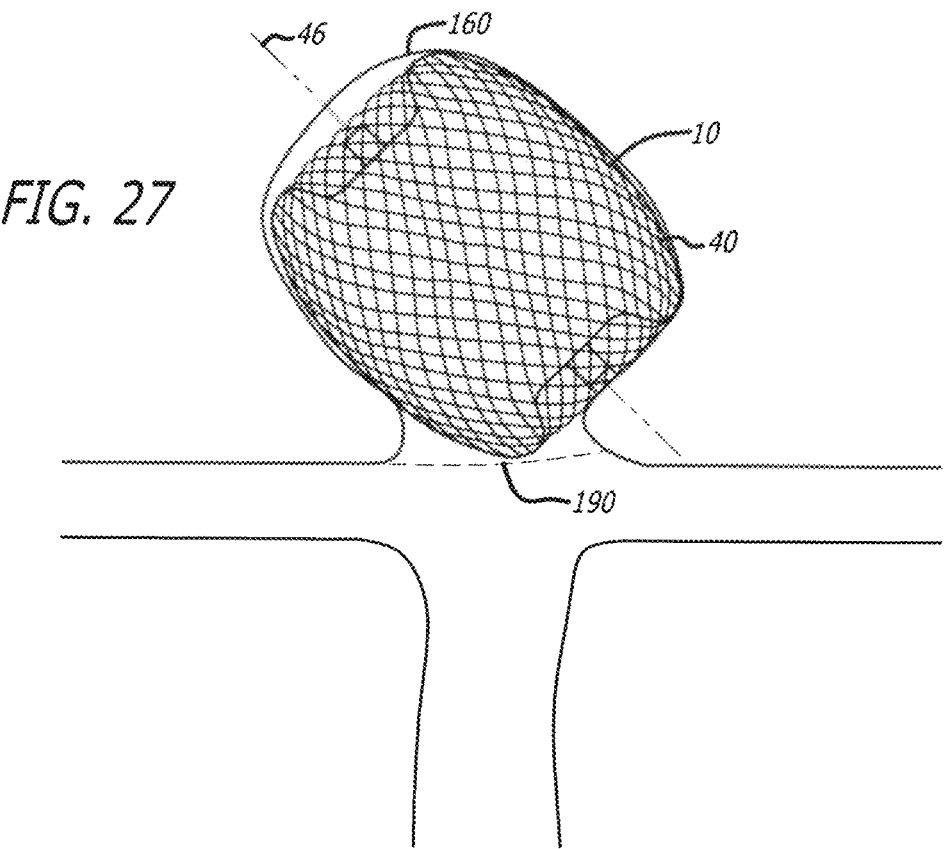
FIG. 27 is an elevation view in partial section of an embodiment of a device for treatment of a patient's vasculature deployed within an aneurysm at a tilted angle.

FIG. 27 illustrates another configuration of a deployed and implanted device in a patient's vascular defect 160. While the implantation configuration shown in FIG. 26 indicates a configuration whereby the longitudinal axis 46 of the device 10 is substantially aligned with a longitudinal axis of the defect 160, other suitable and clinically effective implantation embodiments may be used. For example, FIG. 27 shows an implantation embodiment whereby the longitudinal axis 46 of the implanted device 10 is canted at an angle of about 10 degrees to about 90 degrees relative to a longitudinal axis of the target vascular defect 160. Such an alternative implantation configuration may also be useful in achieving a desired clinical outcome with acute occlusion of the vascular defect 160 in some cases and restoration of normal blood flow adjacent the treated vascular defect. FIG. 28 illustrates a device 10 implanted in an irregularly shaped vascular defect 160. The aneurysm 160 shown has at least two distinct lobes 192 extending from the main aneurysm cavity. The two lobes 192 shown are unfilled by the deployed vascular device 10, yet the lobes 192 are still isolated from the parent vessel of the patient's body due to the occlusion of the aneurysm neck portion 190.

Markers, such as radiopaque markers, on the device 10 or delivery system 112 may be used in conjunction with external imaging equipment (e.g., x-ray) to facilitate positioning of the device or delivery system during deployment. Once the device is properly positioned, the device 10 may be detached by the user. For some embodiments, the detachment of the device 10 from the delivery apparatus 110 of the delivery system 112 may be affected by the delivery of energy (e.g., heat, radiofrequency, ultrasound, vibrational, or laser) to a junction or release mechanism between the device 10 and the delivery apparatus 110. Once the device 10 has been detached, the delivery system 112 may be withdrawn from the patient's vasculature or patient's body 158. For some embodiments, a stent 173 may be place within the parent vessel substantially crossing the aneurysm neck 190 after delivery of the device 10 as shown in FIG. 19 for illustration.

For some embodiments, a biologically active agent or a passive therapeutic agent may be released from a responsive material component of the device 10. The agent release may be affected by one or more of the body's environmental parameters or energy may be delivered (from an internal or external source) to the device 10. Hemostasis may occur within the vascular defect 160 as a result of the isolation of the vascular defect 160, ultimately leading to clotting and substantial occlusion of the vascular defect 160 by a combination of thrombotic material and the device 10. For some embodiments, thrombosis within the vascular defect 160 may be facilitated by agents released from the device 10 and/or drugs or other therapeutic agents delivered to the patient.

For some embodiments, once the device 10 has been deployed, the attachment of platelets to the permeable shell 40 may be inhibited and the formation of clot within an interior space of the vascular defect 160, device, or both promoted or otherwise facilitated with a suitable choice of thrombogenic coatings, anti-thrombogenic coatings or any other suitable coatings (not shown) which may be disposed on any portion of the device 10 for some embodiments, including an outer surface of the filaments 14 or the hubs 66 and 68. Such a coating or coatings may be applied to any suitable portion of the permeable shell 40. Energy forms may also be applied through the delivery apparatus 110 and/or a separate catheter to facilitate fixation and/or healing of the device 10 adjacent the vascular defect 160 for some embodiments. One or more embolic devices or embolic material 176 may also optionally be delivered into the vascular defect 160 adjacent permeable shell portion that spans the neck or opening 190 of the vascular defect 160 after the device 10 has been deployed. For some embodiments, a stent or stent-like support device 173 may be implanted or deployed in a parent vessel adjacent the defect 160 such that it spans across the vascular defect 160 prior to or after deployment of the vascular defect treatment device 10.

In any of the above embodiments, the device 10 may have sufficient radial compliance so as to be readily retrievable or retractable into a typical microcatheter 61. The proximal portion of the device 10, or the device as a whole for some embodiments, may be engineered or modified by the use of reduced diameter filaments, tapered filaments, or filaments oriented for radial flexure so that the device 10 is retractable into a tube that has an internal diameter that is less than about 0.7 mm, using a retraction force less than about 2.7 Newtons (0.6 lbf) force. The force for retrieving the device 10 into a microcatheter 61 may be between about 0.8 Newtons (0.18 lbf) and about 2.25 Newtons (0.5 lbf).

Figure 29:
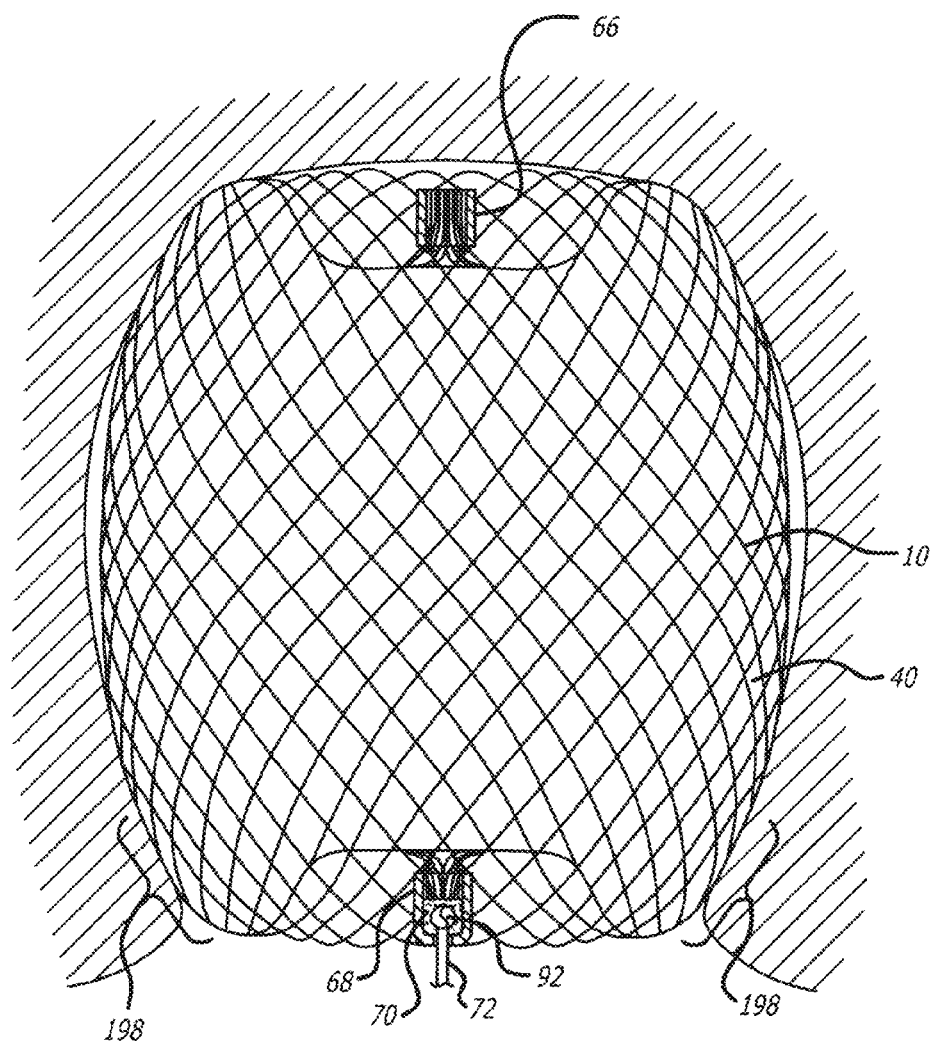
FIG. 29 shows an elevation view in section of a device for treatment of a patient's vasculature deployed within a vascular defect aneurysm.

Engagement of the permeable shell 40 with tissue of an inner surface of a vascular defect 160, when in an expanded relaxed state, may be achieved by the exertion of an outward radial force against tissue of the inside surface of the cavity of the patient's vascular defect 160 as shown in FIG. 29. A similar outward radial force may also be applied by a proximal end portion and permeable shell 40 of the device 10 so as to engage the permeable shell 40 with an inside surface or adjacent tissue of the vascular defect 160. Such forces may be exerted in some embodiments wherein the nominal outer transverse dimension or diameter of the permeable shell 40 in the relaxed unconstrained state is larger than the nominal inner transverse dimension of the vascular defect 160 within which the device 10 is being deployed, i.e., oversizing as discussed above. The elastic resiliency of the permeable shell 40 and filaments 14 thereof may be achieved by an appropriate selection of materials, such as superelastic alloys, including nickel titanium alloys, or any other suitable material for some embodiments. The conformability of a proximal portion of the permeable shell 40 of the device 10 may be such that it will readily ovalize to adapt to the shape and size of an aneurysm neck 190, as shown in FIGS. 20-22, thus providing a good seal and barrier to flow around the device. Thus the device 10 may achieve a good seal, substantially preventing flow around the device without the need for fixation members that protrude into the parent vessel.

Figure 30:
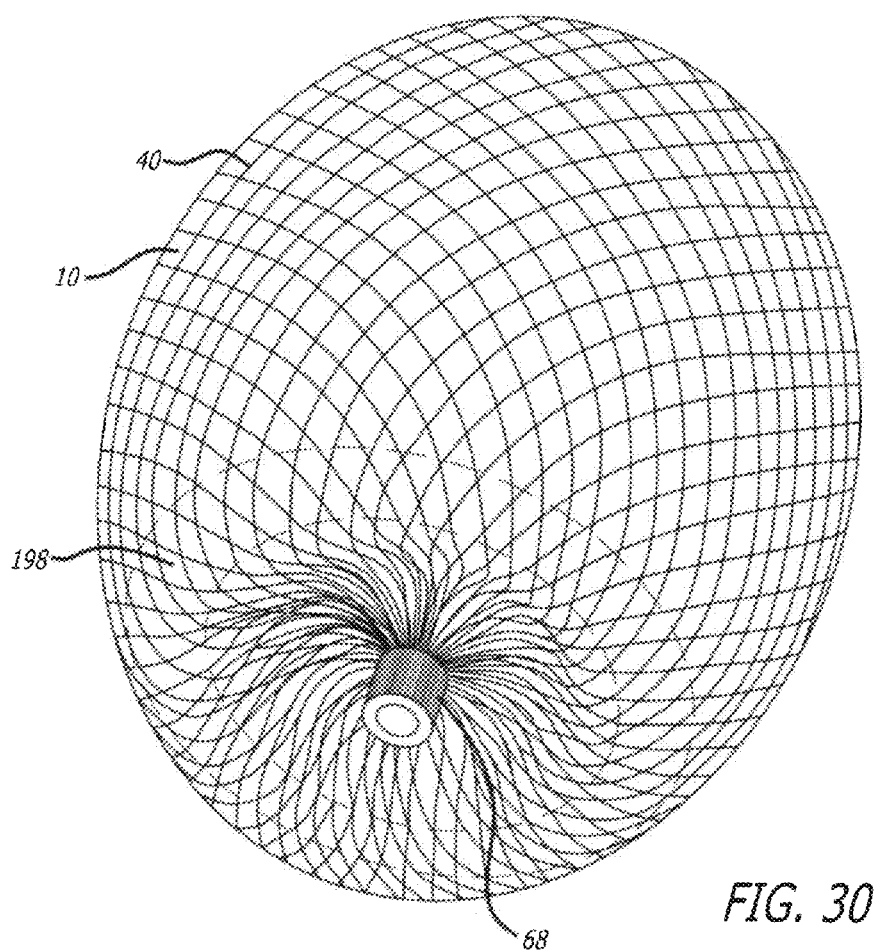
FIG. 30 shows a proximal perspective view of an embodiment of a device for treatment of a patient's vasculature with a sealing zone embodiment indicated by a set of dashed lines.

Some implanted device embodiments 10 have the ends of the filaments 14 of the permeable shell 40 disposed even with or just within a plane formed by the apices of the filaments disposed adjacent to the ends. Some embodiments of the device 10 may also include a sealing member disposed within or about a perimeter zone 198 or other suitable portion of the permeable shell 40 and be configured to facilitate the disruption of flow, a fibrotic tissue response, or physically form a seal between the permeable shell 40 and a surface of the patient's vasculature. The sealing member may comprise coatings, fibers or surface treatments as described herein. The sealing member may be in a part or all of an area of the periphery of the device adjacent where the device contacts the wall of the aneurysm near the aneurysm neck (sealing zone 198) as shown in FIGS. 29 and 30. The zone may extend from about the apex of the outer proximal end radius 88 for a distance up to about 20% of the height of the expanded device 10. The sealing zone 198 may include between about 5% and 30% of the device 10 surface area. Since the flow of blood into an aneurysm 160 generally favors one side of the opening, the sealing member may be incorporated in or attached to the permeable shell 40 structure throughout the peripheral area (sealing zone 198) shown in FIG. 30. Some embodiments of the sealing member may include a swellable polymer. In some embodiments, the sealing member may include or bioactive material or agent such as a biologic material or biodegradable, bioresorbable or other bioactive polymer or copolymers thereof.

Any embodiment of devices for treatment of a patient's vasculature 10, delivery system 112 for such devices 10 or both discussed herein may be adapted to deliver energy to the device for treatment of a patient's vasculature or to tissue surrounding the device 10 at the implant site for the purpose of facilitating fixation of a device 10, healing of tissue adjacent the device or both. In some embodiments, energy may be delivered through a delivery system 112 to the device 10 for treatment of a patient's vasculature such that the device 10 is heated. In some embodiments, energy may be delivered via a separate elongate instrument (e.g., catheter, not shown) to the device 10 for treatment of a patient's vasculature and/or surrounding tissue at the site of the implant 154. Examples of energy embodiments that may be delivered include but are not limited to light energy, thermal or vibration energy, electromagnetic energy, radio frequency energy and ultrasonic energy. For some embodiments, energy delivered to the device 10 may trigger the release of chemical or biologic agents to promote fixation of a device for treatment of a patient's vasculature 10 to a patient's tissue, healing of tissue disposed adjacent such a device 10 or both.

The permeable shell 40 of some device embodiments 10 may also be configured to react to the delivery of energy to effect a change in the mechanical or structural characteristics, deliver drugs or other bioactive agents or transfer heat to the surrounding tissue. For example, some device embodiments 10 may be made softer or more rigid from the use of materials that change properties when exposed to electromagnetic energy (e.g., heat, light, or radio frequency energy). In some cases, the permeable shell 40 may include a polymer that reacts in response to physiologic fluids by expanding. An exemplary material is described by Cox in U.S. Patent Publication No. 2004/0186562, filed Jan. 22, 2004, titled "Aneurysm Treatment Device and Method of Use", which is incorporated by reference herein in its entirety.

Figure 31:
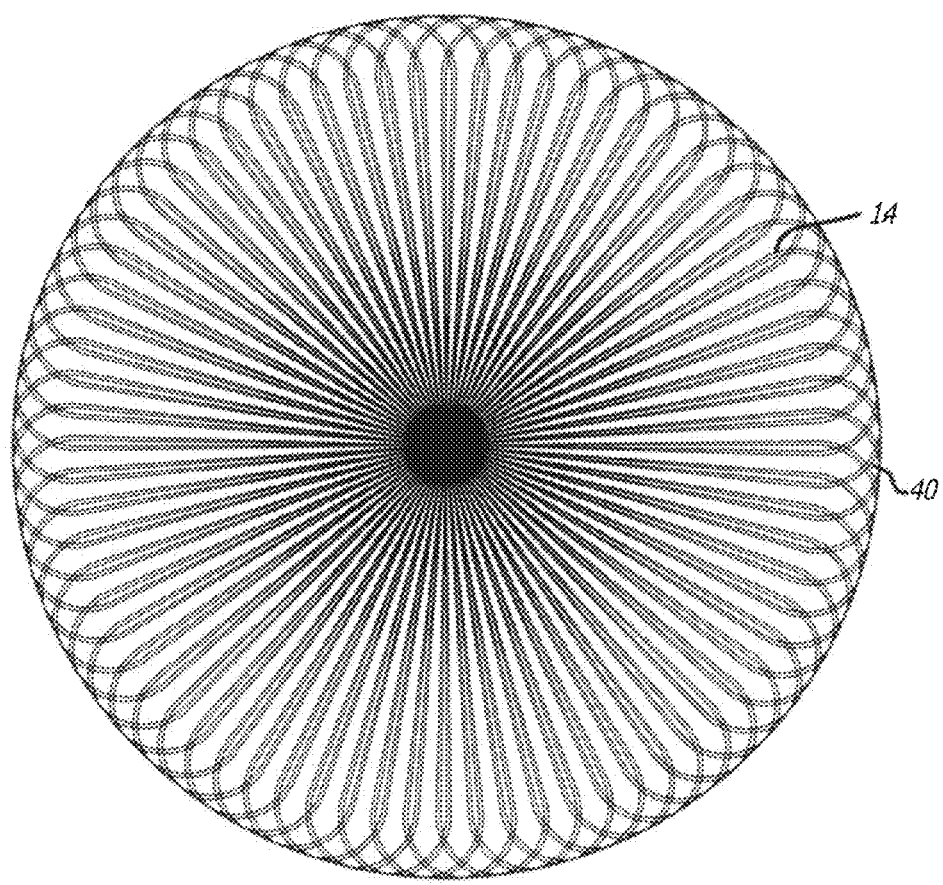
FIGS. 31-35 illustrate various different embodiments of braiding patterns that may be used for permeable shells of devices for treatment of a patient's vasculature.
Figure 32:
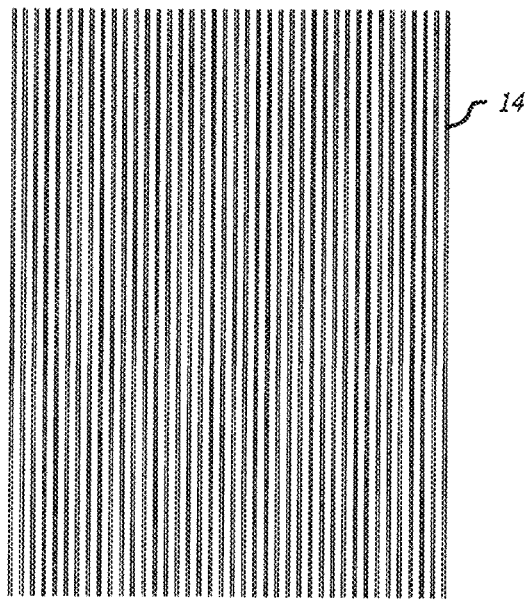
Figure 33:
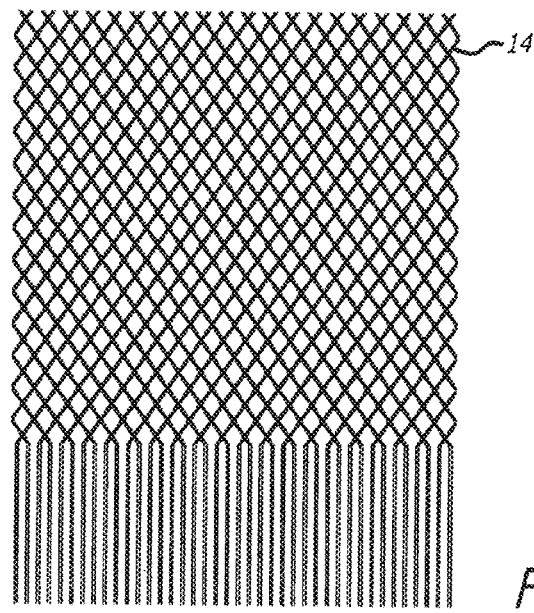
Figure 34:
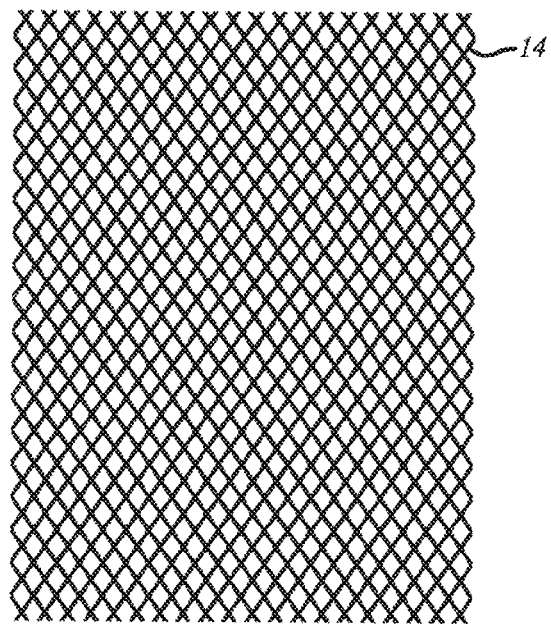

Device embodiments 10 and components thereof discussed herein may take on a large variety of configurations to achieve specific or generally desirable clinical results. In some device embodiments 10, the start of the braided structure of the permeable shell 40 may be delayed from the proximal hub 68 so that the filaments 1 emanate from the proximal hub 68 in a spoke-like radial fashion as shown in the proximal end view of a device in FIG. 31. A flattened analog version of the braid pattern of FIG. 31 is also shown in FIG. 33. This configuration may result in a smaller width gap between the filaments 14 at a given radial distance from the proximal hub 68 relative to a fully braided configuration, the flattened analog pattern of which is shown in FIG. 34. This may provide better flow disruption and promote hemostasis in the area of the device 10 that may be subjected to the highest flow rates. FIG. 32 illustrates a flattened analog representation of a non-braided filament structure for reference.

Figure 35:
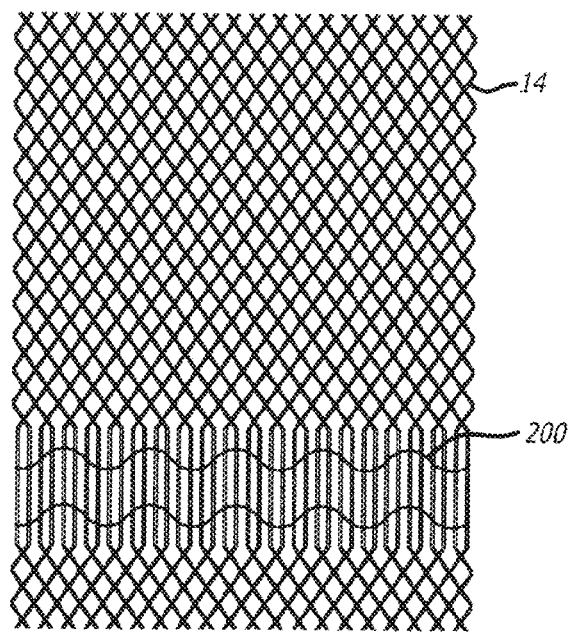

The woven structure may include a portion where the weave or braid of the filaments 14 is interrupted as shown in a flat pattern analog pattern in FIG. 35. In the interrupted region, the filaments 14 may be substantially parallel to each other. The interrupted area may provide a region with different mechanical characteristics such as radial stiffness and/or compliance. Further, the interrupted region may allow for the addition of non-structural fibers or sealing members 200 as described herein or other elements to facilitate fixation, healing, fibrosis or thrombosis. The interrupted region may be within, part of or adjacent to the sealing member zone 198 as shown in FIGS. 29 and 30. The interrupted region may be less than about 50% of the surface area and may be between about 5% and 25% of the surface area.

Figure 36:
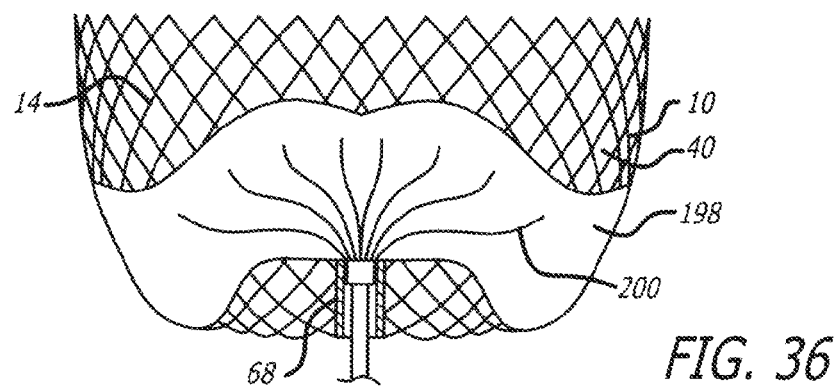
FIG. 36 illustrates a device for treatment of a patient's vasculature that includes non-structural fibers in the permeable shell structure of the device.
Figure 37:
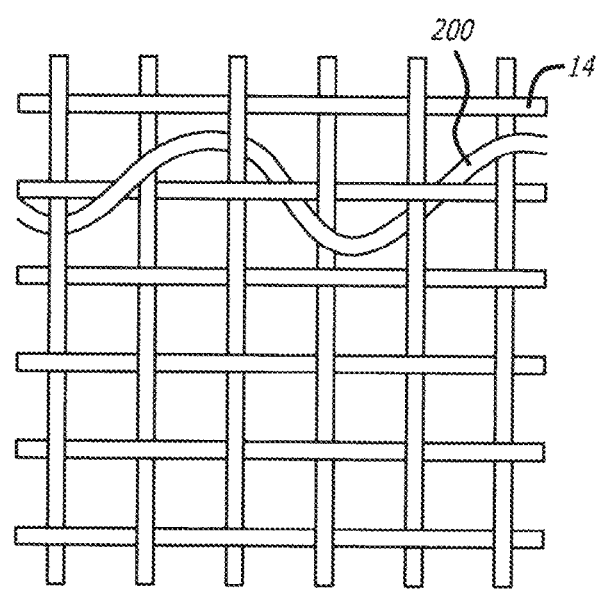
FIG. 37 is an enlarged view of non-structural fibers woven into filaments of a permeable shell structure.

In some embodiments, filamentary or fibrous members that are substantially non-structural may be attached or interwoven into the structural filaments of a portion of the permeable shell to increase a resistance to the flow of blood through the permeable shell structure 40. In some embodiments, a plurality of fibers 200 may be attached on the inner surface of the permeable shell 40 near the proximal hub 68 as shown in FIG. 36. The fibrous members 200 may be the fibers that form the detachment system tether for some embodiments. In some embodiments, one or more fibers 200 may be interwoven into the permeable shell filaments 14 as shown in FIG. 37. The non-structural fibers 200, which may be microfibers or any other suitable fibers, may be polymeric. The non-structural fibers 200 may include, but not limited to, any of the fibers or microfibers discussed or incorporated herein.

In some cases, device embodiments for treatment of a patient's vasculature 10 may generally be fabricated by braiding a substantially tubular braided structure with filamentary elements 14, forming the braided tubular structure into a desired shape, and heat setting the braided formed filaments into the desired shape. Once so formed, the ends of the elongate resilient filaments 14 may then be secured together relative to each other by any of the methods discussed above and proximal and distal hubs 66 and 68 added.

Figure 38:
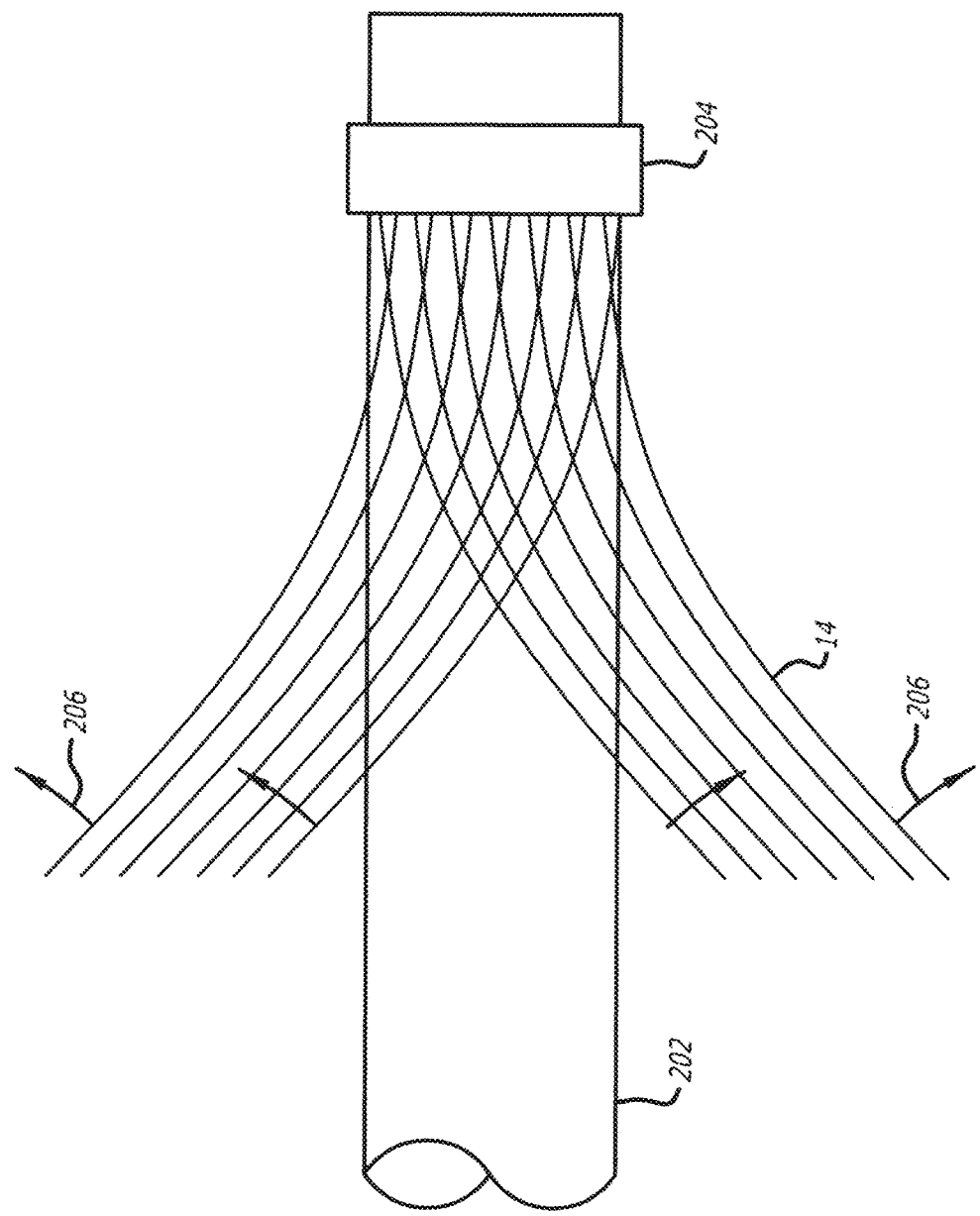
FIG. 38 is an elevation view of a mandrel used for manufacture of a braided tubular member for construction of an embodiment of a device for treatment of a patient's vasculature with the initiation of the braiding process shown.
Figure 39:
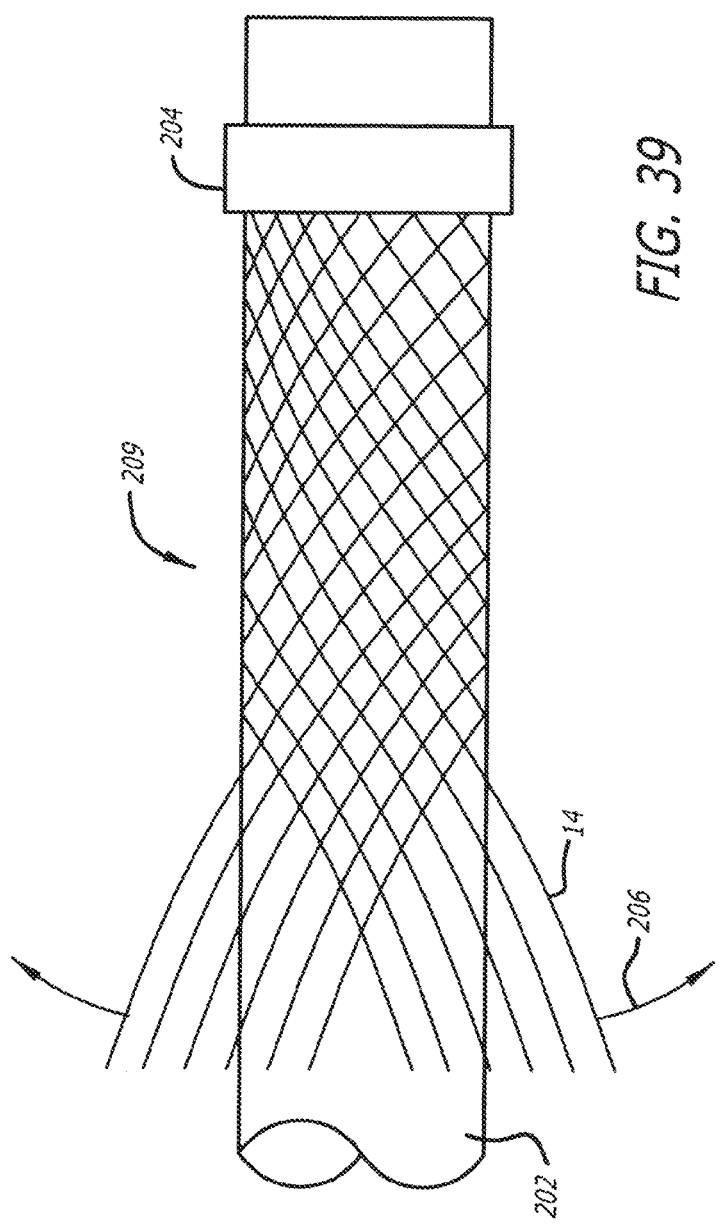
FIG. 39 is an elevation view of a braiding process for a braided tubular member used for manufacture of a device.

Such a braiding process may be carried out by automated machine fabrication or may also be performed by hand. An embodiment of a process for braiding a tubular braided structure by a manual process is shown in FIG. 38. A plurality of elongate resilient filaments 14 are secured at one end of an elongate cylindrical braiding mandrel 202 by a constraining band 204. The band 204 may include any suitable structure that secured the ends of the filaments 14 relative to the mandrel 202 such as a band of adhesive tape, an elastic band, an annular clamp or the like. The loose ends of the filaments 14 opposite the secured ends are being manipulated in a braided or woven pattern as indicated by the arrows 206 to achieve a one over-one under braid pattern for generation of a braided tubular member 208. As discussed above, although a one over-one under simple braid pattern is shown and discussed, other braid or weave patterns may also be used. One such example of another braid configuration may include a two over-one under pattern. FIG. 39 illustrates the braided tubular member 208 taking shape and lengthening as the braiding process continues as indicated by the arrows 206 in FIG. 39. Once the braided tubular member 208 achieves sufficient length, it may be removed from the braiding mandrel 202 and positioned within a shaping fixture such as the shaping fixture embodiments shown in FIGS. 40 and 41.

Figure 40:
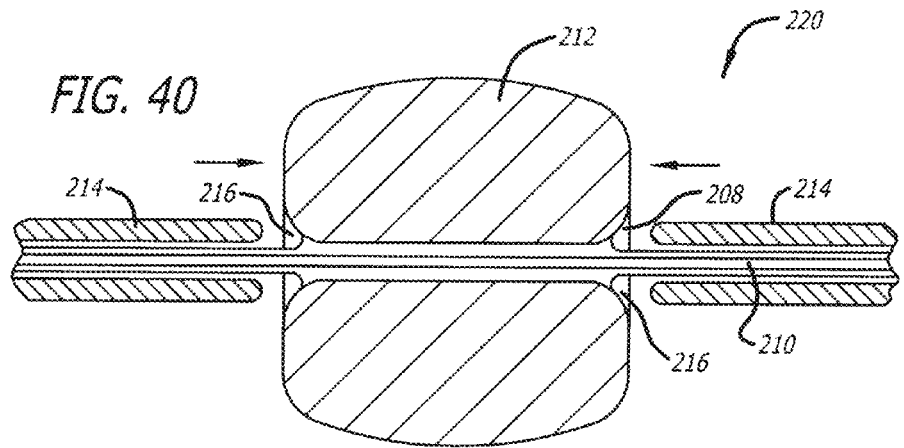
FIG. 40 is an elevation view in partial section of an embodiment of a fixture for heat setting a braided tubular member for manufacture of a device for treatment of a patient's vasculature.

FIG. 40 shows the tubular braided member 208 disposed over an internal rod mandrel 210 that extends through central lumens of an internal ball mandrel 212 and a pair of opposed recessed end forming mandrels 214. The tubular braided member 208 is also disposed over an outer surface of the internal ball mandrel 212 and within an inner lumen of each of the end forming mandrels 214. In order to hold the braided tubular member 208 onto an outer surface contour of the internal ball mandrel 212, including the recessed ends 216 thereof, the end forming mandrels 214 are configured to be pushed against and into the recessed ends 216 of the internal ball mandrel 212 such that the inside surface of the braided tubular member 208 is held against the outer contour of the internal ball mandrel 212 and fixed in place. This entire fixture 220 with the inside surface of the braided tubular structure 208 held against the outside surface of the internal ball mandrel 212 may then be subjected to an appropriate heat treatment such that the resilient filaments 14 of the braided tubular member 208 assume or are otherwise shape-set to the outer contour of the central ball mandrel 212. In some embodiments, the filamentary elements 14 of the permeable shell 40 may be held by a fixture configured to hold the permeable shell 40 in a desired shape and heated to about 475-525 degrees C. for about 5-10 minutes to shape-set the structure.

The central ball mandrel 212 may be configured to have any desired shape so as to produce a shape set tubular braided member 208 that forms a permeable shell 40 having a desired shape and size such as the globular configuration of the device 10 of FIGS. 3-6 above, or any other suitable configuration. As such, the central ball mandrel 212 may also be a globular-shaped ball with recesses in opposing sides for the hubs 66 and 68 that is placed inside the tubular braid 208. A mold or molds that have one or more pieces that are assembled to form a cavity with the desired device shape may also be used in conjunction with or in place of the end forming mandrels 214. Once the heat set process is complete, fibers, coatings, surface treatments may be added to certain filaments, portions of filaments, or all of the permeable shell 40 structure that results. Further, for some embodiments of device processing, the permeable shell 40 may be formed as discussed above by securing proximal ends 60 and distal ends 62 of elongate filamentary elements 14, or to respective proximal and distal hubs 66 and 68.

Figure 41:
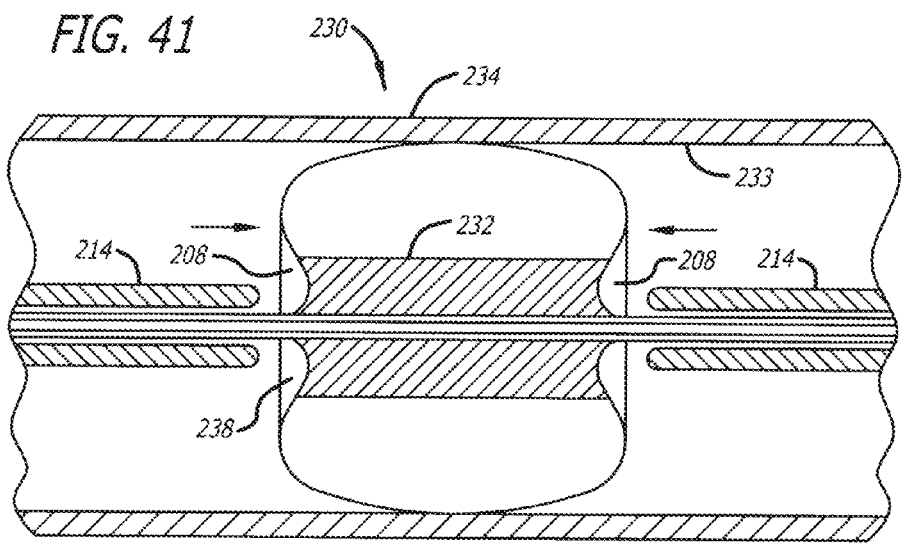
FIG. 41 is an elevation view in partial section of an embodiment of a fixture for heat setting a braided tubular member for manufacture of a device for treatment of a patient's vasculature.

FIG. 41 shows another embodiment of a fixture for shape setting the permeable shell 40 of a device for treatment of a patient's vasculature. The fixture embodiment 230 of FIG. 41 may be used in essentially the same manner as the fixture embodiment 220 of FIG. 40, except that instead of a central ball mandrel 212, an internal tube mandrel 232 is used in conjunction with an external tube restraint 234 in order to hold the shape of the braided tubular member 208 during the heat setting process. More specifically, the tubular braided member 208 is disposed over an internal rod mandrel 210 that extends through central lumens of the internal tube mandrel 232 and a pair of opposed recessed end forming mandrels 214. The tubular braided member 208 is also disposed over an outer surface of the internal tube mandrel 232 and within an inner lumen of each of the end forming mandrels 214.

In order to hold the braided tubular member 208 into a desired shape, including the recessed ends thereof, the end forming mandrels 214 are configured to be pushed against and into recessed ends 238 of the internal tube mandrel 232 such that the inside surface of the braided tubular member 208 is held against the outer contour of the internal tube mandrel 232 and fixed in place at the ends of the tube mandrel 232. Between the ends of the tube mandrel 232, the braided tubular member 208 radially expands outwardly until it touches and is radially constrained by an inside surface of an external tube mandrel 234. The combination of axial restraint and securement of the braided tubular member 208 at the ends of the internal tube mandrel 232 in conjunction with the inward radial restraint on an outside surface of the braided tubular member 208 disposed between the proximal and distal ends thereof, may be configured to produce a desired globular configuration suitable for the permeable shell 40 of the device 10.

Once again, this entire fixture 230 with the inside surface of the ends of the braided tubular structure 208 held against the outside surface of the ends of the internal tube mandrel 232 and an outside surface of the braided tubular member 208 radially constrained by an inside surface 233 of the external tube member 234, may then be subjected to an appropriate heat treatment. The heat treatment may be configured such that the resilient filaments 14 of the braided tubular member 208 assume or are otherwise shape-set to the globular contour of the filaments 14 generated by the fixture 230. In some embodiments, the filamentary elements 14 of the permeable shell 40 may be held by a fixture configured to hold the braided tubular member 208 in a desired shape and heated to about 475-525 degrees C. for about 5-10 minutes to shape-set the structure. The internal tube mandrel 232 and inside surface 233 of the external tube member 234 may be so configured to have any desired shape so as to produce a shape set tubular braided member 208 that forms a permeable shell 40 having a desired shape and size such as the globular configuration of the device of FIGS. 3-6 above, or any other suitable configuration.

For some embodiments, material may be attached to filaments 14 of the permeable shell 40 of a device 10 such that it substantially reduces the size of the fenestrations, cells or pores 64 between filaments 14 and thus reduces the porosity in that area. For example, coating embodiments may be disposed on portions of the filaments 14 to create small fenestrations or cells and thus higher density of the permeable shell 40. Active materials such as a responsive hydrogel may be attached or otherwise incorporated into permeable shell 40 of some embodiments such that it swells upon contact with liquids over time to reduce the porosity of the permeable shell 40.

Device embodiments 10 discussed herein may be coated with various polymers to enhance its performance, fixation and/or biocompatibility. In addition, device embodiments 10 may be made of various biomaterials known in the art of implant devices including but not limited to polymers, metals, biological materials and composites thereof. Device embodiments discussed herein may include cells and/or other biologic material to promote healing. Device embodiments discussed herein may also be constructed to provide the elution or delivery of one or more beneficial drugs, other bioactive substances or both into the blood or the surrounding tissue.

Permeable shell embodiments 40 of devices for treatment of a patient's vasculature 10 may include multiple layers. A first or outer layer may be constructed from a material with low bioactivity and hemocompatibility so as to minimize platelet aggregation or attachment and thus the propensity to form clot and thrombus. Optionally, an outer layer may be coated or incorporate an antithrombogenic agent such as heparin or other antithrombogenic agents described herein or known in the art. One or more inner layers disposed towards the vascular defect in a deployed state relative to the first layer may be constructed of materials that have greater bioactivity and/or promote clotting and thus enhance the formation of an occlusive mass of clot and device within the vascular defect. Some materials that have been shown to have bioactivity and/or promote clotting include silk, polylactic acid (PLA), polyglycolic acid (PGA), collagen, alginate, fibrin, fibrinogen, fibronectin, Methylcellulose, gelatin, Small Intestinal Submucosa (SIS), poly-N-acetylglucosamine and copolymers or composites thereof.

Bioactive agents suitable for use in the embodiments discussed herein may include those having a specific action within the body as well as those having nonspecific actions. Specific action agents are typically proteinaceous, including thrombogenic types and/or forms of collagen, thrombin and fibrogen (each of which may provide an optimal combination of activity and cost), as well as elastin and von Willebrand factor (which may tend to be less active and/or expensive agents), and active portions and domains of each of these agents. Thrombogenic proteins typically act by means of a specific interaction with either platelets or enzymes that participate in a cascade of events leading eventually to clot formation. Agents having nonspecific thrombogenic action are generally positively charged molecules, e.g., polymeric molecules such as chitosan, polylysine, poly(ethylenimine) or acrylics polymerized from acrylimide or methacrylamide which incorporate positively-charged groups in the form of primary, secondary, or tertiary amines or quaternary salts, or non-polymeric agents such as (tridodecylmethylammonium chloride). Positively charged hemostatic agents promote clot formation by a non-specific mechanism, which includes the physical adsorption of platelets via ionic interactions between the negative charges on the surfaces of the platelets and the positive charges of the agents themselves.

Device embodiments 10 herein may include a surface treatment or coating on a portion, side or all surfaces that promotes or inhibits thrombosis, clotting, healing or other embolization performance measure. The surface treatment or coating may be a synthetic, biologic or combination thereof. For some embodiments, at least a portion of an inner surface of the permeable shell 40 may have a surface treatment or coating made of a biodegradable or bioresorbable material such as a polylactide, polyglycolide or a copolymer thereof. Another surface treatment or coating material that may enhance the embolization performance of a device includes a polysaccharide such as an alginate based material. Some coating embodiments may include extracellular matrix proteins such as ECM proteins. One example of such a coating may be Finale™ Prohealing coating that is commercially available from Surmodics Inc., Eden Prairie, Minn. Another exemplary coating may be Polyzene-F that is commercially available from CeloNovo BioSciences, Inc., Newnan, Ga. In some embodiments, the coatings may be applied with a thickness that is less than about 25% of a transverse dimension of the filaments 14.

Antiplatelet agents may include aspirin, glycoprotein IIb/IIIa receptor inhibitors (including, abciximab, eptifibatide, tirofiban, lamifiban, fradafiban, cromafiban, toxifiban, XV454, lefradafiban, klerval, lotrafiban, orbofiban, and xemiofiban), dipyridamole, apo-dipyridamole, persantine, prostacyclin, ticlopidine, clopidogrel, cromafiban, cilostazol, and nitric oxide. To deliver nitric oxide, device embodiments may include a polymer that releases nitric oxide. Device embodiments 10 may also deliver or include an anticoagulant such as heparin, low molecular weight heparin, hirudin, warfarin, bivalirudin, hirudin, argatroban, forskolin, ximelagatran, vapiprost, prostacyclin and prostacyclin analogues, dextran, synthetic antithrombin, Vasoflux, argatroban, efegatran, tick anticoagulant peptide, Ppack, HMG-CoA reductase inhibitors, and thromboxane A2 receptor inhibitors.

In some embodiments, the permeable shell 40 of a device 10 may be coated with a composition that may include nanoscale structured materials or precursors thereof (e.g., self-assembling peptides). The peptides may have with alternating hydrophilic and hydrophobic monomers that allow them to self-assemble under physiological conditions. The composition may comprise a sequence of amino acid residues. In some embodiments, the permeable shell may include a thin metallic film material. The thin film metal may be fabricated by sputter deposition and may be formed in multiple layers. The thin film may be a nickel-titanium alloy also known as nitinol.

Figure 42:
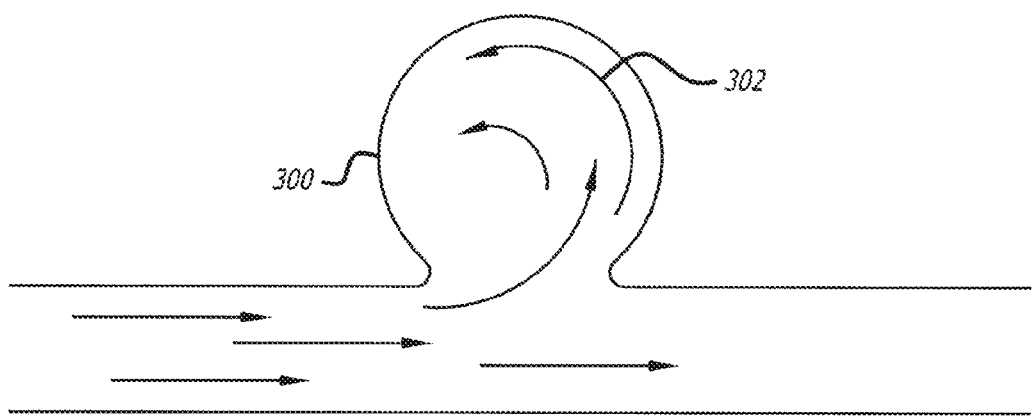
FIG. 42 is an elevation view in section that illustrates a flow of blood within an aneurysm of a patient's vasculature.

In some instances, saccular aneurysms may have a generally circular flow dynamic 302 of blood as shown in FIG. 42. While the shell slows flow into the aneurysm 300, thrombosis and embolization may be further enhanced by an internal porous structure. In particular, a structure that is formed so that the circular flow 302, and in particular the highest velocity region is forced to pass through one or more porous layers may have a synergistic treatment effect and promote rapid thrombosis.

Figure 43:
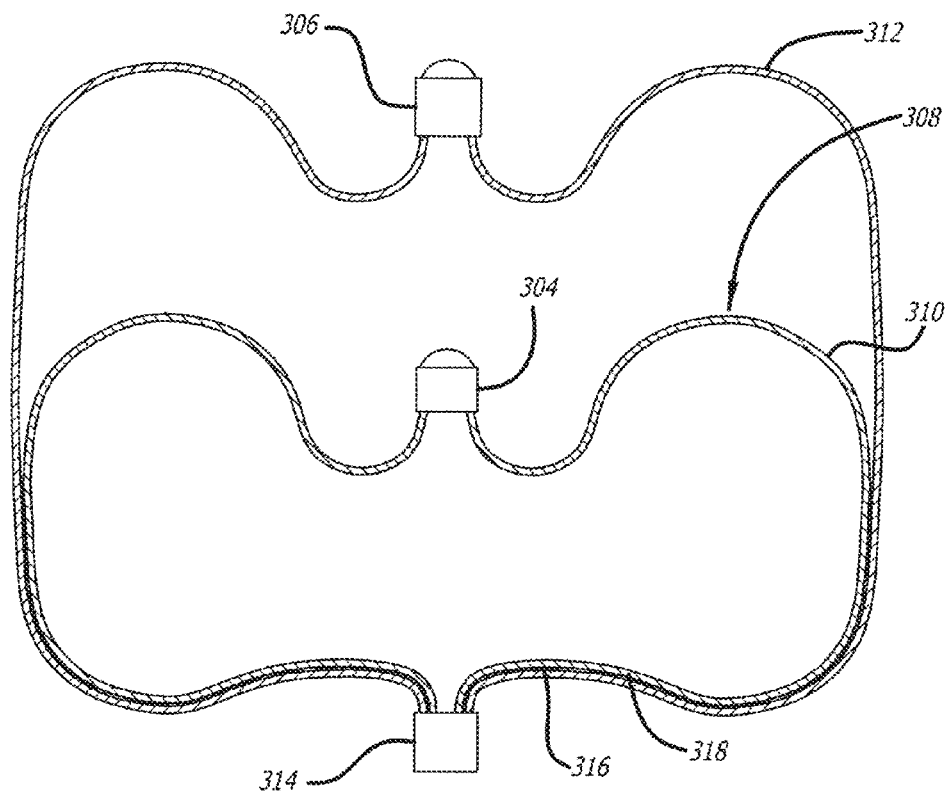
FIG. 43 is an elevation view in partial section of an embodiment of a device for treatment of a patient's vasculature.

In some embodiments, the distal end 308 of the inner layer (or structure) 310 may terminate with a connection or hub 304 as shown in FIG. 43. With an internal termination of the inner structure 310, the potential problem of length matching and buckling may be minimized due to the ability of the inner layer 310 to collapse without affecting, or minimally affecting, the outer layer 312. In some embodiments, the collapsed length of the inner layer or structure 310 may be less than about 80% of the collapsed length of the outer layer or structure 312. A proximal hub 314 is also shown for terminating the proximal end 316 of the outer layer 312 and the proximal end 318 of the inner layer 310.

Figure 44:
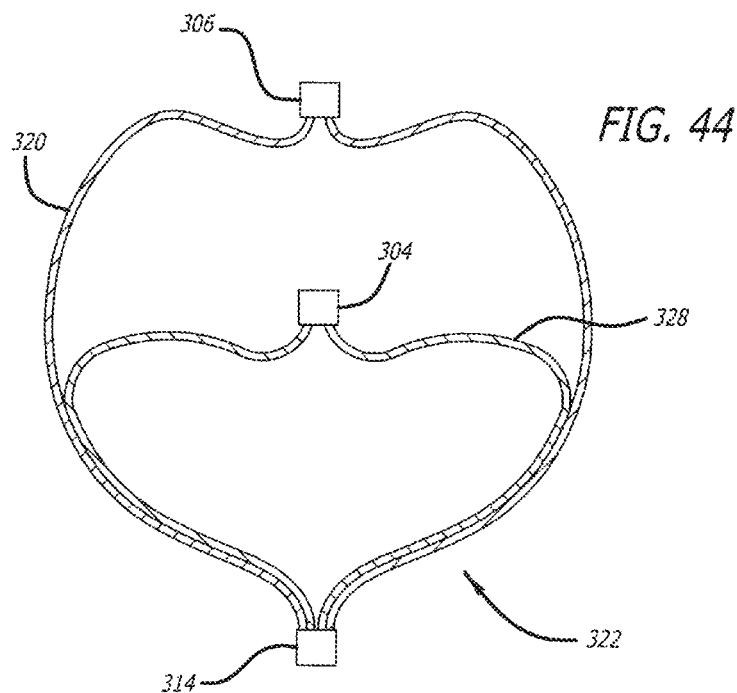
FIG. 44 is an elevation view in partial section of an embodiment of a device for treatment of a patient's vasculature.
Figure 45:
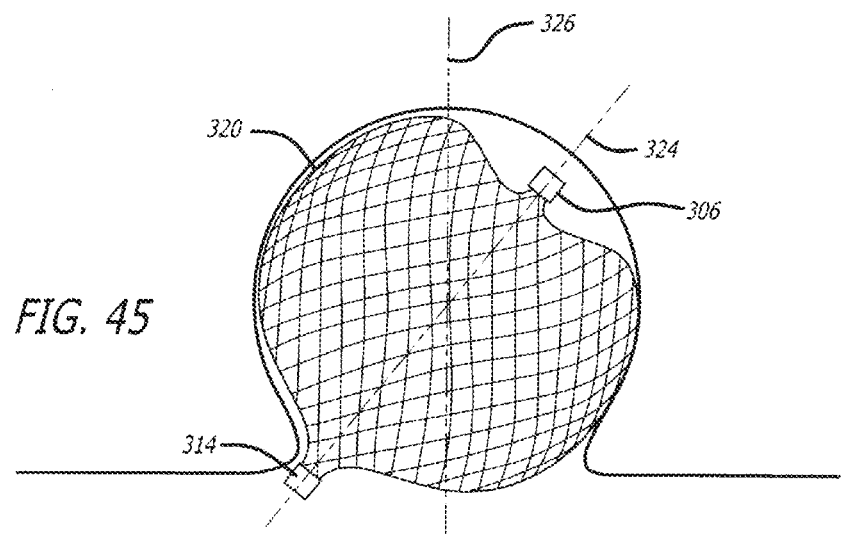
FIG. 45 is an elevation view of an embodiment of a device for treatment of a patient's vasculature.

In some embodiments, features of which are shown in FIG. 44, the outer structure 320 may have a truncated sphere or generally heart-like cross-sectional shape. The proximal portion 322 may be generally convex or semi-circular. These features allow the device to be placed into a saccular vascular site such as a cerebral aneurysm at an angled orientation relative to an axis 326 of the aneurysm as shown in FIG. 45. The semi-circular proximal surface presents a relatively constant shape to the parent vessel irrespective of the angulation of the device axis 324.

In some embodiments, the inner structure may be formed such that at least about 80% of the volume of the inner structure 328 is contained within the lower or more proximal half of the outer structure or shell volume. For some embodiments, the mesh density of the inner structure may be higher than a density of the mesh structure of the outer shell or structure. In some embodiments, the inner structure may be substantially within the proximal or lower 80% 330 of the outer shell internal volume as shown in FIG. 46.

The inner structure 328 may be formed by braiding, weaving, or other filament interlacing techniques described herein similar to that used for formation of the shell or those techniques known in the art of medical textiles and intravascular implants. Alternatively, it may be merely twisted or allowed to form a random mesh of filaments. It may be heat set as described herein and similar to that used to form the shell or it may not be heat treated beyond any heat setting done when the filaments are formed. The inner structure filaments may be metals, polymers or composites thereof. In some embodiments, the filaments are formed of materials that can withstand heat treatment of at least about 450° C. In some embodiments, some of the filaments may be formed of an aramide fiber such as poly paraphenylene terephthalamide available under the trade name Kevlar. In some embodiments, the inner structure filamentary members may be wires with a diameter between about 10 microns (0.0004 inches) and about 30 microns (0.0012 inches). The inner structure may comprise materials, coatings or be impregnated with particles or molecules that release elements or chemicals that promote thrombosis and thrombus formation.

The inner structure occupying the lower portion of the outer shell may provide rapid progression of thrombosis particularly in the distal portion of an aneurysm. In some embodiments, this configuration may provide protection of the distal "dome" portion of an aneurysm where it is generally thought to be the weakest and most prone to rupture. Thus, embodiments with proximal inner structures may provide a method of rapidly occluding a distal portion of an aneurysm that is visible under angiography. An embodiment of this process is illustrated in the angiographic images, shown in FIGS. 47 and 48 of a model aneurysm created in an animal for purpose of evaluating a device embodiment. FIG. 47 is the pre-treatment angiogram of an aneurysm created in an animal model prior to treatment with an embodiment of a device for treatment of a patient's vasculature having some similarity in structure to the device embodiment shown in FIG. 43. FIG. 48 is representative of an angiogram ten (10) minutes post treatment with the device for treatment of a patient's vasculature showing rapid occlusion of the distal portion of the aneurysm.

Generally speaking, one or more of the features, dimensions or materials of the various device embodiments discussed herein may be used in other similar device embodiments discussed herein, as well as with other device embodiments. For example, any suitable feature, dimension or material discussed here may also be applied to device embodiments such as those discussed in commonly owned U.S. Patent Publication No. 2011/0022149, published Jan. 27, 2011, titled "Methods and Devices for Treatment of Vascular Defects", U.S. Patent Publication No. 2009/0275974, published Nov. 5, 2009, titled "Filamentary Devices for Treatment of Vascular Defects", U.S. Patent Publication No. 2011/0152993, published Jun. 23, 2011, titled "Multiple Layer Filamentary Devices for Treatment of Vascular Defects" and U.S. Publication No. 2012/0283768, published Nov. 8, 2012, titled "Method and Apparatus for the Treatment of Large and Giant Vascular Defects", all of which are incorporated by reference herein in their entirely.

In any of the device embodiments discussed or incorporated herein for treatment of a patient's vascular defect or aneurysm, the device may comprise one or more composite filaments. A composite filament (e.g., wires) may be defined as a filament that comprises a plurality of materials in either a mixture or alloy or in a composite structure where two materials are physically combined into one. The addition of at least some composite wires into the device may provide improved visibility of the device under external imaging such as x-ray, fluoroscopy, magnetic resonance imaging and the like. In some embodiments, composite wires may provide improved mechanical characteristics.

Figure 49:
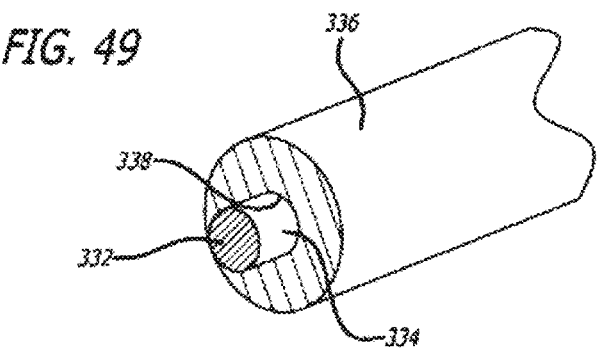
FIG. 49 is a perspective view in section of a of a composite filament embodiment.

For some composite filament embodiments, the composite filaments may be disposed in a coaxial arrangement with one material substantially inside the other as shown in FIG. 49. One known method of fabrication of such a coaxial composite wire is a drawn filled tube wire wherein the materials of the drawn filled tube are combined but retain their individual mechanical properties. Drawn filled tube wires are commercially available from Ft. Wayne Metals, Ft. Wayne, Ind. In some cases, the process for producing drawn filled tube filaments may include extreme compressive forces such that the mechanical bond between an outer surface 334 of the internal fill wire 332 and an internal surface 338 of the external tube 336 is metallurgically sound. In some instances, a plurality of external tubes, each of a different material, may be layered over the internal wire and each other in order to combine the mechanical properties of the plurality of materials. For such embodiments, the drawn filled tube filament may include 2, 3, 4, 5 or more external tube layers. In some embodiments, the drawn filled tube wires are formed of a combination of an external nitinol (NiTi) tube and a highly radiopaque fill wire that may be concentrically disposed within the external tube. Various radiopaque materials and metals known in the art may be used as the fill wire including but not limited to gold, platinum, tantalum and the like. One advantage of a composite with a NiTi exterior and internal highly radiopaque fill wire is that the device can substantially maintain its highly elastic or superelastic behavior and the majority of the blood contacting surfaces remain nitinol. This allows for a device with substantially improved visibility under x-ray imaging while maintaining the proper range of mechanical characteristics.

In some cases, the specific construction of a drawn filled tube wire or filament may be important in order to maintain desired performance characteristics of a device for treatment of a vascular defect. More specifically, it may be important to balance the stiffness, elasticity and radiopacity of the composition. In particular, for drawn filled tube filament embodiments that include an internal wire 332 of ductile radiopaque material such as platinum and an outer tube 336 of an elastic or superelastic material such as NiTi, it can be necessary to carefully balance the ratio of the percent cross sectional area of the internal wire with regard to the overall cross sectional area of the filament. Such a ratio may be referred to as a fill ratio. If an embodiment includes too little radiopaque or highly radiopaque internal tube material relative to the external tube material, there may not be sufficient radiopacity and visibility. On the other hand, if an embodiment includes too much internal wire material with respect to the elastic external tube, the mechanical properties of the ductile radiopaque material may overwhelm the elastic properties of the outer tube material and the filaments may be prone to taking a set after compression etc. resulting in permanent deformation. For some embodiments, a desired composite or drawn filled tube wire may be constructed with a fill ratio of cross sectional area of internal fill wire to cross sectional area of the entire composite filament of between about 10% and about 50%, more specifically between about 20% and about 40%, and even more specifically, between about 25% and about 35%.

In some embodiments, the number of composite wires may be between about 40 and 190, and between about 50 and 190 in other embodiments, and between about 70 and 150 in other embodiments. In some embodiments, the devices for treatment of a patient's vasculature may have at least about 25% composite wires relative to the total number of wires and in some embodiments such devices may have at least about 40% composite wires relative to a total number of wires in the device. For example, a first subset of elongate resilient filaments may comprise filaments, each having a composite of highly radiopaque material and a high strength material, and a second subset of elongate resilient filaments may consist essentially of a high strength material. For example, the highly radiopaque material may comprise platinum, platinum alloy such as 90% platinum/10% iridium, or gold or tantalum. The high strength material may comprise NiTi. While composite wires may provide enhanced visualization and/or mechanical characteristics, they may in some configurations have reduced tensile strength in comparison to NiTi wires of a similar diameter. In other configurations, depending on their diameter, the composite wires may increase the collapsed profile of the devices. Therefore, it may be beneficial to minimize the number. Lower percentages of composite wires may not be sufficiently visible with current imaging equipment particularly in neurovascular applications where the imaging is done through the skull. In addition, too many composite wires (or composite wires with extremely high fill ratios) may result in devices with excessive artifact on CT or MRI imaging. The described ratios and amounts of highly radiopaque material provide a unique situation for neurovascular implants where the periphery of the device is just visible under transcranial fluoroscopy but the device imaged area is not completely obliterated (i.e., due to artifact) as it is with conventional embolic coils that are made substantially out of platinum or platinum alloys.

One manner of achieving the desired degree of radiopacity is by selecting a particular combination of fill ratio of the composite wires and the percent of composite wires in relation to the total number of wires. Devices according to embodiments having a single layer braided (woven) structure were constructed. For example, an embodiment of a braided structure comprising 72 composite Platinum/NiTi drawn filled tube wires having a 0.00075" diameter and a platinum fill ratio of 30% and 72 NiTi wires having a 0.00075" diameter was constructed. The total percent of platinum (by total % cross sectional area) in the braided structure was about 15%. Another embodiment of a braided structure comprising 108 composite Platinum/NiTi drawn filled tube wires having a 0.001" diameter and a platinum fill ratio of 30% and 72 NiTi wires having a 0.00075" diameter was constructed. The total percent of platinum in the braided structure was about 22%. Still another embodiment of a braided structure comprising 72 composite Platinum/NiTi drawn filled tube wires having a 0.00125" diameter and a platinum fill ratio of 30% and 108 NiTi wires having a 0.00075" diameter was constructed. The total percent of platinum in the braided structure was about 19.5%. Yet another embodiment of a braided structure comprising 108 composite Platinum/NiTi drawn filled tube wires having a 0.00125" diameter and a platinum fill ratio of 30% and 108 NiTi wires having a 0.00075" diameter was constructed. The total percent of platinum in the braided structure was about 22%. Devices constructed according to each of these embodiments were each implanted into living bodies and imaged using fluoroscopy. In each case, the periphery of the device was visible under transcranial fluoroscopy but the device imaged area was not completely obliterated (i.e., due to artifact).

Additionally, devices according to embodiments having an outer braided (woven) structure and an inner braided (woven) structure (as in FIGS. 43-46) were constructed. For example, an embodiment having a braided outer structure comprising 54 composite Platinum/NiTi drawn filled tube wires having a 0.001" diameter and a platinum fill ratio of 30% and 54 NiTi wires having a 0.00075" diameter, and having a braided inner structure comprising 108 NiTi wires having a 0.00075" diameter was constructed. The total percent of platinum in the braided outer structure was about 19%. The total percent of platinum in the combined outer structure and inner structure was about 11%. Still another embodiment having a braided outer structure comprising 48 composite Platinum/NiTi drawn filled tube wires having a 0.001" diameter and a platinum fill ratio of 30% and 96 composite Platinum/NiTi drawn filled tube wires having a 0.0015" diameter and a platinum fill ratio of 30%, and having a braided inner structure comprising 132 NiTi wires having a 0.00075" diameter and 12 NiTi wires having a 0.001" diameter was constructed. The total percent of platinum in the braided outer structure was about 30%. The total percent of platinum in the combined outer structure and inner structure was about 18.5%. Devices constructed according to each of these embodiments were each implanted into living bodies and imaged using fluoroscopy. In each case, the periphery of the device was visible under transcranial fluoroscopy but the device imaged area was not completely obliterated (i.e., due to artifact).

In some embodiments the total cross sectional area of the highly radiopaque material is between about 11% and about 30% of the total cross sectional area of the plurality of elongate elements. In some embodiments the total cross sectional area of the highly radiopaque material is between about 15% and about 30% of the total cross sectional area of the plurality of elongate elements. In some embodiments the total cross sectional area of the highly radiopaque material is between about 15% and about 22% of the total cross sectional area of the plurality of elongate elements. In some embodiments the total cross sectional area of the highly radiopaque material is between about 19% and about 30% of the total cross sectional area of the plurality of elongate elements. In some embodiments the total cross sectional area of the highly radiopaque material is between about 11% and about 18.5% of the total cross sectional area of the plurality of elongate elements.

Because the radiopacity of the composite filaments comprising a highly radiopaque material can allow sufficient device visualization (e.g., on fluoroscopy), it may be desired to make one or more of the hubs 304, 306, 314 from less radiopaque or non-radiopaque materials. In some embodiments, platinum, platinum alloy (e.g., 90% Platinum/10% Iridium), may not be desired, if their radiopacity would overpower the radiopacity of the composite filaments, and thus, make their delineation difficult. The use of less radiopaque or non-radiopaque materials to make the hubs 304, 306, 314 may thus be desired in these embodiments, but can also be used on the hubs 66, 68 of other embodiments. One or more titanium or titanium alloy hubs or NiTi hubs may be used in place of highly radiopaque hubs. The use of titanium, titanium alloy, or NiTi hubs may also aid in welding to NiTi filaments, as their melt temperatures are more closely matched than if, for example, platinum, platinum alloy, or gold hubs were being used. The result can be a joint between the filaments and the hub that has a higher tensile breakage force. Joints of this variety were constructed and demonstrated an approximately 48% improvement in tensile force.

In some embodiments, composite filaments or wires may be made, at least in part from various single and multi-layered, coiled or braided configurations. One potentially suitable component is called a Helical Hollow Strand™ and is commercially available from Ft. Wayne Metals, Ft. Wayne, Ind. Another potential construction is commercially available from Heraeus Medical Components.

One embodiment of a device for treatment of a patient's vasculature may include a self-expanding resilient permeable structure having a proximal end, a distal end, a longitudinal axis, a radially constrained elongated state configured for delivery within a catheter lumen, an expanded state with a globular and longitudinally shortened configuration relative to the radially constrained state and extending from the longitudinal axis between the proximal end and the distal end, a plurality of elongate resilient filaments secured relative to each other at at least one of the proximal end or distal end, wherein the elongate resilient filaments include a first subset of elongate resilient filaments, each of the first subset of filaments including a composite of a highly radiopaque material and a high strength material, and each of a second subset of elongate resilient filaments essentially of a high strength material, wherein the first subset of filaments is about 25% to about 40% of the total number of the plurality of elongate resilient filaments. In a particular embodiment, the high strength material of the elongate resilient filaments of the first subset of filaments and the high strength material of the elongate resilient filaments of the second subset of filaments comprise a superelastic material, for example NiTi. In one embodiment, the first subset of elongate resilient filaments may comprise about 50 to about 190 filaments. In one embodiment, the first subset of elongate resilient filaments may comprise about 70 to about 150 filaments. In one embodiment, the elongate resilient filaments may comprise drawn filled tube wires. In one embodiment, drawn filled tube wires may have a cross-sectional fill area ratio of between about 10% and about 50%. In one embodiment, drawn filled tube wires may have a cross-sectional fill area ratio of between about 20% and about 40% In one embodiment, drawn filled tube wires may have a cross-sectional fill area ratio of between about 25% and about 35%. In one embodiment, the highly radiopaque material may include tantalum. In one embodiment, the highly radiopaque material may include platinum. In one embodiment, the highly radiopaque material may include gold.

One embodiment of a device for treatment of a patient's vasculature may include a self-expanding resilient permeable structure having a proximal end, a distal end, a longitudinal axis, a radially constrained elongated state configured for delivery within a catheter lumen, an expanded state with a globular and longitudinally shortened configuration relative to the radially constrained state and extending from the longitudinal axis between the proximal end and the distal end, a plurality of elongate resilient filaments secured relative to each other at at least one of the proximal end or distal end, wherein the elongate resilient filaments include a first subset of elongate resilient filaments, each of the first subset of filaments including a composite of a highly radiopaque material and a high strength material, and each of a second subset of elongate resilient filaments essentially of a high strength material, wherein the first subset of filaments is at least about 25% of the total number of the plurality of elongate resilient filaments. In a particular embodiment, the high strength material of the elongate resilient filaments of the first subset of filaments and the high strength material of the elongate resilient filaments of the second subset of filaments comprise a superelastic material, for example NiTi. In one embodiment, the first subset of filaments is at least 40% of the total number of the plurality of elongate resilient filaments. In one embodiment, the first subset of elongate resilient filaments may comprise about 50 to about 190 filaments. In one embodiment, the first subset of elongate resilient filaments may comprise about 70 to about 150 filaments. In one embodiment, the elongate resilient filaments may comprise drawn filled tube wires. In one embodiment, drawn filled tube wires may have a cross-sectional fill area ratio of between about 10% and about 50%. In one embodiment, drawn filled tube wires may have a cross-sectional fill area ratio of between about 20% and about 40% In one embodiment, drawn filled tube wires may have a cross-sectional fill area ratio of between about 25% and about 35%. In one embodiment, the highly radiopaque material may include tantalum. In one embodiment, the highly radiopaque material may include platinum. In one embodiment, the highly radiopaque material may include gold.

One embodiment of a device for treatment of a patient's vasculature may include a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, which define a cavity of the permeable shell and which include at least about 40% composite filaments relative to a total number of filaments, the composite filaments including a high strength material and a highly radiopaque material. In one embodiment, the plurality of elongate filaments may be secured relative to each other at a distal end of the permeable shell. In one embodiment, the plurality of elongate filaments may be secured relative to each other at a proximal end of the permeable shell. In one embodiment, the plurality of elongate filaments may include about 50 to about 190 composite filaments. In one embodiment, the plurality of elongate filaments may include about 70 to about 150 composite filaments. In one embodiment, the composite filaments may be drawn filled tubes. In one embodiment, drawn filled tube wires may have a fill ratio of cross sectional area of between about 10% and about 50%. In one embodiment, drawn filled tube wires may have a fill ratio of cross sectional area of between about 20% and about 40% In one embodiment, drawn filled tube wires may have a fill ratio of cross sectional area of between about 25% and about 35%. %. In one embodiment, the highly radiopaque material may include tantalum. In one embodiment, the highly radiopaque material may include platinum. In one embodiment, the highly radiopaque material may include gold.

One embodiment of a device for treatment of a patient's vasculature may include a self-expanding resilient permeable shell having a radially constrained elongated state configured for delivery within a catheter lumen, an expanded state with a globular and longitudinally shortened configuration relative to the radially constrained state, and a plurality of elongate filaments which are woven together, the plurality of filaments having a total cross sectional area and further defining a cavity of the permeable shell and which include at least some composite filaments, the composite filaments including a high strength material and a highly radiopaque material, and wherein the total cross sectional area of the highly radiopaque material is between about 11% and about 30% of the total cross sectional area of the plurality of elongate filaments. In one embodiment, the total cross sectional area of the highly radiopaque material is between about 15% and about 30% of the total cross sectional area of the plurality of elongate filaments. In one embodiment, the total cross sectional area of the highly radiopaque material is between about 15% and about 22% of the total cross sectional area of the plurality of elongate filaments. In one embodiment, the total cross sectional area of the highly radiopaque material is between about 19% and about 30% of the total cross sectional area of the plurality of elongate filaments. In one embodiment, the total cross sectional area of the highly radiopaque material is between about 11% and about 18.5% of the total cross sectional area of the plurality of elongate filaments. In one embodiment, the plurality of elongate filaments may be secured relative to each other at a distal end of the permeable shell. In one embodiment, the plurality of elongate filaments may be secured relative to each other at a proximal end of the permeable shell. In one embodiment, the plurality of elongate filaments may include about 50 to about 190 composite filaments. In one embodiment, the plurality of elongate filaments may include about 70 to about 150 composite filaments. In one embodiment, the composite filaments may be drawn filled tubes. In one embodiment, drawn filled tube wires may have a fill ratio of cross sectional area of between about 10% and about 50%. In one embodiment, drawn filled tube wires may have a fill ratio of cross sectional area of between about 20% and about 40% In one embodiment, drawn filled tube wires may have a fill ratio of cross sectional area of between about 25% and about 35%. %. In one embodiment, the highly radiopaque material may include tantalum. In one embodiment, the highly radiopaque material may include platinum. In one embodiment, the highly radiopaque material may include gold.

Figure 50A:
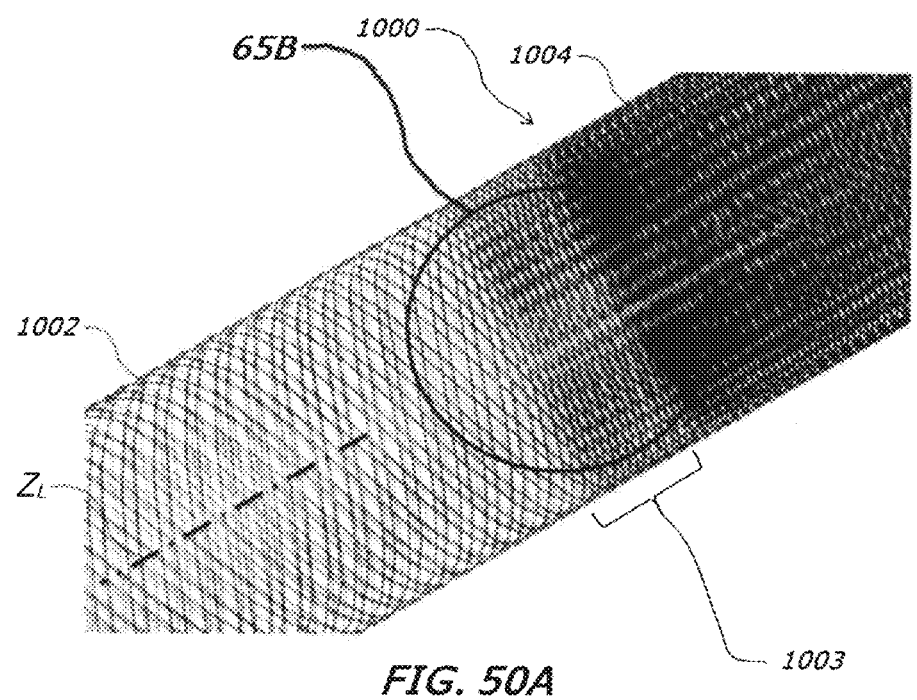
FIG. 50A illustrates a braided tubular member.
Figure 50B:
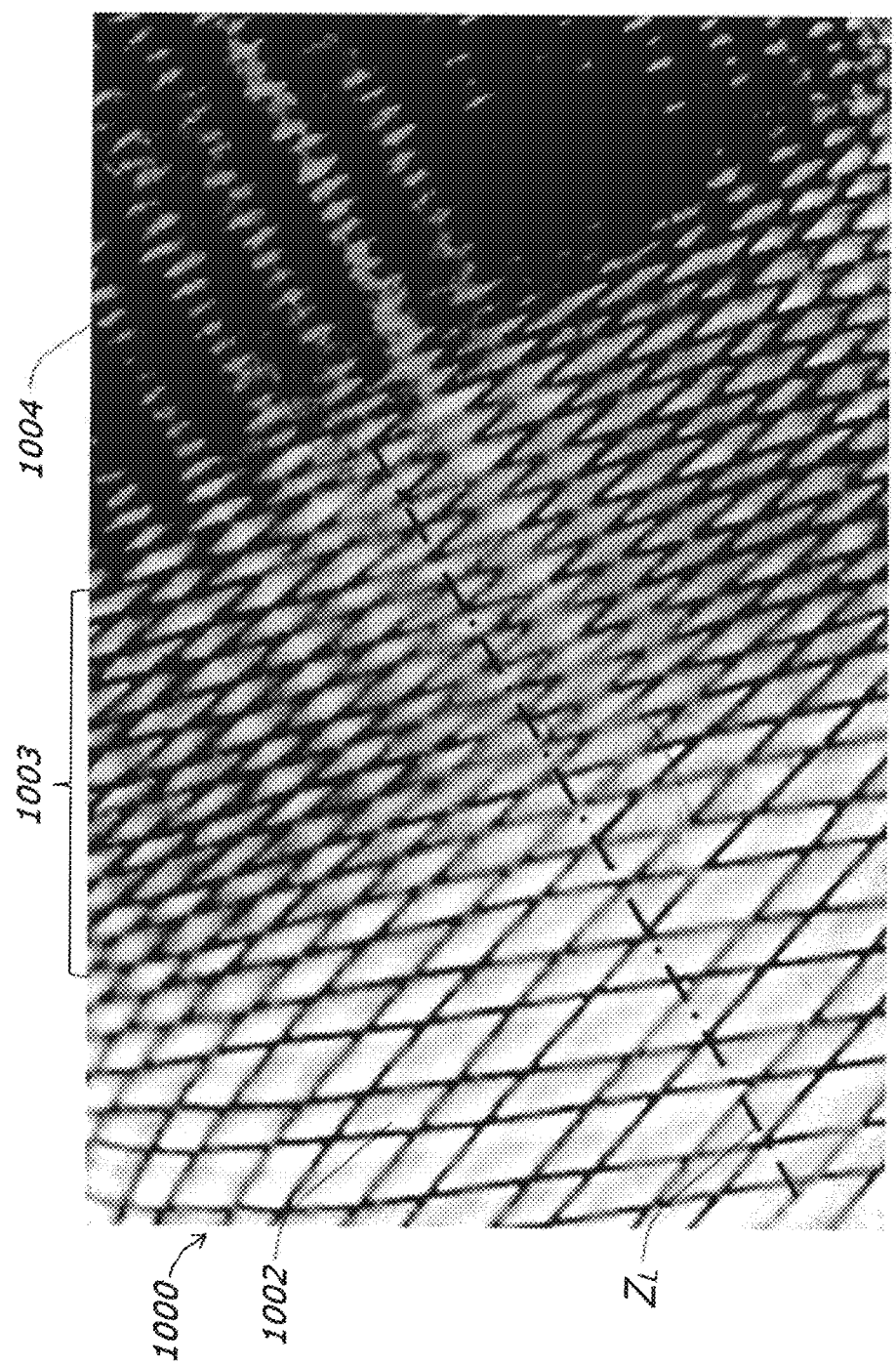
FIG. 50B is a detailed view of the braided tubular member of FIG. 50A.
Figure 50D:
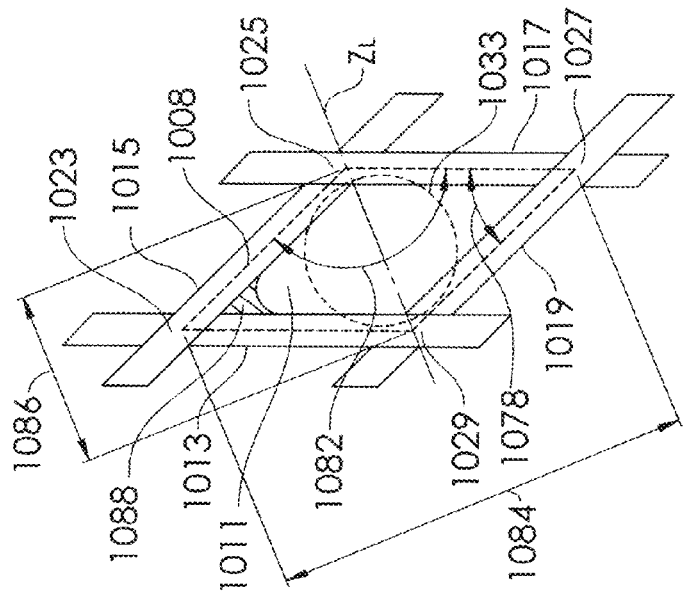
FIG. 50D is a single diamond-shaped module from the series of diamond-shaped modules of FIG. 50C.
Figure 50C:
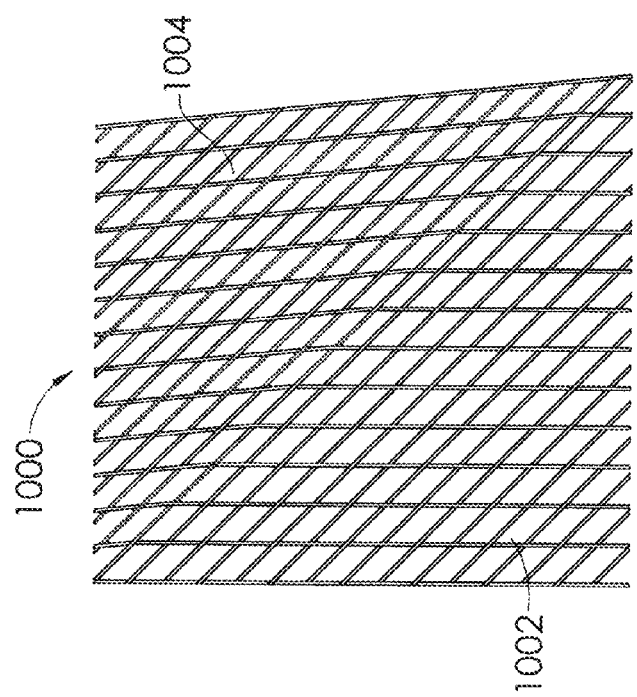
FIG. 50C is a two-dimensional depiction of a braided tubular member as a series of individual diamond-shaped modules.

FIGS. 50A and 50B illustrate a braided tubular member 1000 for producing a mesh device having a single layer with at least two distinct braided portions: a first braided portion 1002 having a first braid density ($BD_1$) and a second braided portion 1004 having a second braid density ($BD_2$). The braided tubular member extends along a longitudinal axis $Z_L$. A transition portion 1003 having a transitioning braid density ($BD_T$) is located between the first braided portion 1002 and the second braided portion 1004. As illustrated in FIGS. 50C and 50D, modular braid density ($BD_M$) is a two-dimensional representation of the percent area coverage of filaments in a substantially diamond-shaped module 1008 within the braid. Braid density (BD) as described herein is different from the traditional "braid wire density" which is described in picks per inch (PPI) or picks per centimeter. "Braid wire density" is not a ratio of areas, but rather the number of wire crossings within a particular length of a tubular section. "Braid wire density" is blind to the amount of material coverage within a certain area, because it does not take into account the wire diameter or diameters. Braid density (BD), on the other hand, is specific to the percent of material coverage within a certain area. The substantially diamond-shaped module 1008 is a two-dimensional area $A_M$ inside the diamond-shaped dashed lines in FIG. 50D. The substantially diamond-shaped module 1008 includes a substantially diamond-shaped opening 1011 having an area $A_O$, which is surrounded by four filaments: a first filament 1013, a second filament 1015, a third filament 1017, and a fourth filament 1019. As will be described further, the four filaments 1013, 1015, 1017, 1019 may comprise four individual wires, or alternatively, two or more filaments may be made from the same wire. The four filaments 1013, 1015, 1017, 1019 cross each other around the diamond-shaped opening 1011 at a first crossing 1023 between first filament 1013 and second filament 1015, a second crossing 1025 between second filament 1015 and third filament 1017, a third crossing 1027 between third filament 1017 and fourth filament 1019, and a fourth crossing 1029 between fourth filament 1019 and first filament 1013. The area $A_M$ within the diamond-shaped module 1008 and the area $A_O$ within the diamond-shaped opening 1011 may each be approximated by the formula for area of a parallelogram (base multiplied by height, where height is perpendicular to the base). The four dashed lines in FIG. 50D are each centered between the two outer extents of the filament transverse thickness (e.g., filament width or circular filament diameter). Therefore, the area $A_M$ of the diamond-shaped module 1008 includes the area $A_O$ of the diamond-shaped opening 1011 and the area of one-half of the thickness of each of the four filaments 1013, 1015, 1017, 1019 surrounding the diamond-shaped opening 1011. As mentioned, two or more of the filaments may have a different thickness from each other, or all may be the same thickness. The modular braid density ($BD_M$) calculated at a single module is:

$$BD_M=(A_M-A_O)/A_M$$

where $A_M$ is area of the diamond-shaped module, and $A_O$ is the area of the diamond-shaped opening.

In an embodiment of a braided tubular member 1000 having a fixed diameter, fixed circumference, and a fixed number of filaments, the number of diamond-shaped modules 1008 fitting within the fixed circumference will not change, regardless of how sparsely or densely the braid is formed. Therefore, the module width 1084 will remain the same dimension, regardless of how sparsely or densely the braid is formed. However, the module length 1086 will be shorter as the braid is formed more densely, and the module length 1086 will be longer as the braid is formed more sparsely. During braiding, to accommodate this change in the module length 1086 without a change in module width 1084, filament 1015 and filament 1017 will slide over one another at crossing 1025 and filament 1013 and filament 1019 will slide over one another at crossing 1029 while angle 1082 and the angle across from angle 1082 change. In conjunction with this, filament 1013 and filament 1015 will swivel in relation to one another at crossing 1023 and filament 1017 and filament 1019 will swivel in relation to one another at crossing 1027 while angle 1078 and the angle across from angle 1078 change. For example, as the braid is wound more densely, angle 1082 and the angle across from angle 1082 will both increase while angle 1078 and the angle across from angle 1078 both decrease. Moreover, as the braid is wound more sparsely, angle 1082 and the angle across from angle 1082 will both decrease while angle 1078 and the angle across from angle 1078 both increase. It should be noted that angle 1082 in braiding nomenclature would be two times the "braid angle".

The increase or decrease in module length 1086 with braiding "density" change, coupled with the constant module width 1084, means that the number of modules in a certain circumferential "row" will not change with a change in angles 1078, 1082, but the number of modules in a certain axial "column" will change. To calculate the cylindrical braid density ($BD_C$), one must sum both the numerators and denominators of all of the modular braid densities within the cylindrical area having k modules, and then take the ratio:

$$BDC=\Sigma(AMk-AOk)/\Sigma(A_Mk)$$

k=1, 2, 3, . . . , n where $A_M$ is area of the diamond-shaped module, and $A_O$ is the area of the diamond-shaped opening, and In the case that there is some variance in the modular braid densities ($BD_M$) over a specific portion of a braided tubular member 1000, or a mesh device made from a braided tubular member 1000, the cylindrical braid density ($BD_C$) may be calculated. A first example of varying modular braid densities ($BD_M$) is in a transition portion 1003, where modular braid densities ($BD_M$) increase or decrease along the longitudinal axis $Z_L$. A second example of varying modular braid densities ($BD_M$) is in a mesh device having a spherical or globular shape, where the modular braid densities ($BD_M$) decrease towards the outer radius of the mesh device and increase towards the center or longitudinal axis $Z_L$ of the mesh device. It is assumed that the key braid density (BD) in a braid portion that is located near the maximum flow into a vascular defect, such as an aneurysm, is the braid density (BD) at the most expanded diameter. The braid density (BD) inherently becomes greater towards the central axis of the mesh device, because the effective diameter (and thus circumference) decreases, thus leaving less space for the same number of filaments 1005, and thus decreasing the module width 1084 of each module.

In several embodiments of mesh devices, the mesh device is formed from a braided tubular member 1000 having at least two distinct braided portions 1002, 1004, so that the mesh device itself may have at least two distinct braided portions. One of the main purposes of having at least two braided portions, is that a more sparsely braided portion may be mechanically easier to diametrically constrain for delivery within the small lumen of a microcatheter 61 and provide a more flexible device for delivering through a tortuous path, while a more densely braided portion may be more effective in disrupting blood flow, for example, when the more densely braided portion is placed at the neck or opening of an aneurysm or other vascular defect. As the second braided portion 1004 is braided more densely (i.e., with increased angle 1082 and decreased angle 1078), the resistance to flow through the diamond-shaped opening 1011 increases. The flow through a diamond-shaped opening 1011 can be characterized by the hydraulic diameter ($D_H$) 1033, a theoretical circular diameter which represents the same flow characteristics as the diamond-shaped opening 1011. Hydraulic diameter ($D_H$) is typically used to represent flow through various non-circular lumens or openings, like the diamond-shape opening 1011. This is because non-circular openings may have low flow zones, like the low flow zone 1088 in the diamond-shaped opening 1011. The formula for hydraulic diameter ($D_H$) is:

$$D_H=(4 \times A_O)/P_O$$

Where $A_O$ is the area of the diamond-shaped opening, and $P_O$ is the perimeter of the diamond-shaped opening.

Braid density (BD) may be used to compare one portion of the braided tubular member 1000 to another portion of the braided tubular member 1000. Braid density (BD) may also be used to compare a portion adjacent the longitudinal axis $Z_L$ of the braided tubular member 1000 with the most expanded section within the same portion of the braided tubular member. Braid density (BD) may be used to compare one portion of a mesh device constructed from the braided tubular member 1000 to another portion of the mesh device constructed from the braided tubular member, for example, the most expanded section of a first portion with the most expanded portion of a second portion. As mentioned, the most expanded section of a portion intended to disrupt flow (for example, at the neck of an aneurysm), is relevant in predicting the effectiveness in disrupting flow in a worst-case, high flow location. Braid density may also be represented as the average (i.e., mean, median) of several different portions of a braided tubular member 1000 of a mesh device made from the braided tubular member 1000. Braid density may also be represented as the average of measurements of the same portion of several braided tubular members 1000 or mesh devices constructed from braided tubular members 1000.

Mesh devices of several of the described embodiments are formed from a braided tubular member 1000, which is initially braided by at least one of braiding machines 1050, 1100. Braiding machines 1050, 1100, shown in the embodiment of FIG. 51 and the embodiment of FIG. 52, respectively, are of the vertical type, i.e., the braiding axis (Z) of a cylindrical braiding mandrel 1010, about which a tubular braid 1055 (see FIG. 54A) is formed, extends in the vertical direction. A vertical-type braiding apparatus provides more convenient access by the operator to various parts of the apparatus than a horizontal-type apparatus wherein the braid is formed about a horizontal axis. A vertical-type braiding apparatus also takes advantage of the aid of gravity, without the need of significant complexity, for example through the use of pulleys, weights or other mechanisms. The braiding machines 1050, 1100 include a circular disc 1020, from which the mandrel 1010 extends perpendicularly. The external diameter of the mandrel 1010 determines the internal diameter of the braid formed thereon. In some embodiments, the mandrel may range from about 2 mm to about 50 mm. Likewise, the length of the mandrel 1010 determines the length of the braid that can be formed. The uppermost end of the mandrel 1010 has a tip 1012 having a smaller diameter than the mandrel 1010 which forms a recess or notch 1014 (FIG. 54A) for loading a plurality of filaments on the tip of mandrel 1010. In use, a plurality of filaments 1005*a-n* is loaded onto mandrel tip 1012, such that each filament extends radially toward the circumferential edge 1022 of the disc 1020.

The filaments 1005 may be looped over mandrel 1010 such that the loop catches on the notch 1014 formed at the junction of tip 1012 and mandrel 1010. For example, a single wire 1007 can be looped over and affixed to the mandrel 1010 to create two individual braiding filaments 1005*a,b*. This offers better loading efficiency because the attachment of the filaments 1005 at the tip 1012 of the mandrel 1010 may be simplified. Alternatively, the filaments 1005 may be temporarily secured at the mandrel tip 1012 by a constraining band, such as a band of adhesive tape, an elastic band, an annular clamp, or the like. The filaments 1005*a-n* are arranged such that they are spaced apart around the circumferential edge 1022 of the disc 1020 and each engage the edge 1022 at a point that is spaced apart a circumferential distance d (FIG. 53) from the points engaged by the immediately adjacent filaments.

In some embodiments, the mandrel may be loaded with about 10 to 1500 filaments, alternatively about 10 to 1000 filaments, alternatively about 10 to 500 filaments, alternatively about 18 to 288 filaments, alternatively 104, 108, 144, 162, 180, 216, 288, 360, or 800 filaments. In the event that a wire 1007 is draped over the mandrel 1010, there would be ½ the number of wires 1007 because each wire 1007 results in two braiding filaments 1005. The filaments 1005*a-n* may have a transverse dimension or diameter of about 0.0005 to 0.005 inches (½ to 5 mils), alternatively about 0.0075 to 0.002 inches (¾ to 2 mils). In some embodiments, the braid may be formed of filaments 1005 of multiple sizes. For example, filaments 1005*a-n* may include large filaments having a transverse dimension or diameter that is about 0.001 to 0.005 inches (1-5 mils) and small filaments having a transverse dimension or diameter of about 0.0004 to 0.0015 inches (½-1.5 mils), more specifically, about 0.0004 inches to about 0.001 inches. In addition, a difference in transverse dimension or diameter between the small filaments and the large filaments may be less than about 0.005 inches, alternatively less than about 0.0035 inches, alternatively less than about 0.002 inches. For embodiments that include filaments of different sizes, the number of small filaments relative to the number of large filaments may be about 2 to 1 to about 15 to 1, alternatively about 2 to 1 to about 12 to 1, alternatively about 4 to 1 to about 8 to 1.

The circular disc 1020 defines a plane 1021 and a circumferential edge 1022. A motor 1018 (FIG. 54A), such as a stepper motor, is attached to disc 1020 to rotate the disc in discrete steps. The motor 1018 and control system may be housed in a cylindrical drum 1060 connected to the bottom side of the disc 1020, or may be located separate from the drum 1060, and coupled to the top or bottom of the drum 1060 and the disc 1020 by gearing, pulleys, or a chain drive. In some embodiments, the drum 1060 may have a diameter about equal to the disc 1020 such that the longitudinal side of the drum 1060 can act as a physical mechanism to stabilize the filaments 1005 extending over the edge of the disc 1020. For example, in some embodiments, the side of the drum 1060 may be made of an energy absorbing, slightly textured, grooved surface, or surface having projections such that when the filaments 1005 extend over the edge of the disc 1020, they will come to rest against the side of drum 1060 such that the filaments 1005 are substantially vertical, and not tangled.

Figure 53:
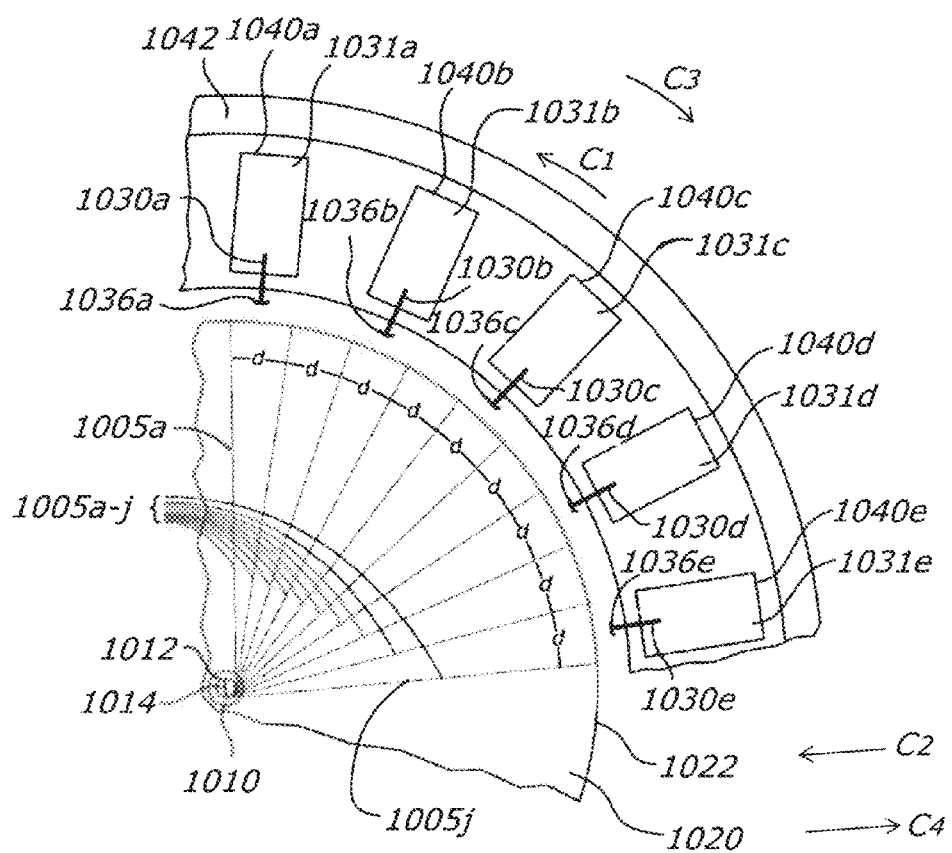
FIG. 53 is a plan view of a section of the braiding device of FIG. 52 illustrating the braiding machine loaded with a plurality of filaments.

A plurality of catch mechanisms 1030 (see FIG. 53) are positioned around the circumference of disc 1020, with each catch mechanism 1030 extending toward the circumferential edge 1022 of the disc 1020 and arranged to selectively capture an individual filament 1005 extending over the edge of disc 1020. The catch mechanisms 1030 may comprise hooks, barbs, magnets, or any other magnetic, suction, or mechanical component known in the art that is capable of selectively capturing and releasing one or more filaments 1005. For example, as shown in FIG. 53, in one embodiment, the catch mechanism 1030 may comprise a double headed hook 1036 at the distal end for engaging a filament 1005 located on either side of the catch mechanism 1030. The curve of the hooks may be slightly J-shaped, as shown, to encourage retention of the filament 1005 in the hook. Alternatively, the hooks may be more L-shaped to facilitate release of an engaged filament when the hook is rotated away from the filament 1005.

The number of catch mechanisms 1030 determines the maximum number of filaments 1005 that can loaded on the braiding machine 1050, 1100, and therefore, the maximum number of filaments 1005 in a braid 1055 made thereon. The number of catch mechanisms 1030 will generally be ½ the maximum number of filaments 1005. Each catch mechanism 1030 may handle two threads (or more); therefore, for example, a braiding machine 1050, 1100 having 144 double hook catch mechanisms 1030 extending circumferentially around disc 1020 can be loaded with a maximum of 288 filaments. Because each of catch mechanism 1030 is individually activated, however, the machine can also be operated in a partially loaded configuration loaded with any even number of filaments 1005 to create braids 1055 having a range of filaments 1005.

Each catch mechanisms 1030 is connected to an actuator 1040 that controls the movement of the catch mechanism 1030 toward and away from circumferential edge 1022 of the disc 1020 to alternately engage and release the filaments 1005 one at a time. The actuator 1040 may be any type of linear actuator known in the art such as electrical, electromechanical, mechanical, hydraulic, or pneumatic actuators, or any other actuators known in the art that are capable of moving the catch mechanism 1030 and an engaged filament 1005 a set distance both away from and toward the disc 1020. The catch mechanism 1030 and the actuators 1040 are positioned around the circumference of the disc 1020 such that the motion of the actuators 1040 causes the catch mechanisms 1030 to be moved in a generally radial direction away from and toward circumferential edge 1022 of disc 1020. The catch mechanisms 1030 are further positioned such that the catch mechanisms 1030 engage the selected filament 1005 as it extends over the circumferential edge 1022 of the disc 1020. For example, in some embodiments, the catch mechanisms 1030 are located in a horizontal plane and slightly beneath the plane defined by the disc 1020. Alternatively, the catch mechanisms 1030 may be angled such that when they are moved toward the disc 1020, they will intercept the filament 1005 at a point below the plane 1021 defined by disc 1020. As shown in FIGS. 51-54A, the plurality of catch mechanisms 1030 and actuators 1040 may be attached to a stationary track 1042 surrounding the circular disc 1020, and the circular disc configured to rotate. Alternatively to a rotatable disc 1020, the plurality of catch mechanisms 1030 and actuators 1040 may be attached to a rotatable circular track (not shown), which is configured to rotate around a stationary disc. A motor, such as a stepper motor, may be attached to the circular track to rotate the catch mechanisms 1030 in discrete steps relative to the disc 1020. An alternative embodiment having both a stationary track and a stationary disc 1020 is also possible. In this particular embodiment, the plurality of catch mechanisms 1030 and actuators 1040 may be driven in the manner of train cars around the inner diameter of the stationary track.

In use, as shown in FIG. 53, mandrel 1010 is loaded with a plurality of filaments 1005a-j, which extend radially over the circumferential edge 1022 of the circular disc 1020. Each of the filaments 1005a-j engages the circumferential edge 1022 of the disc 1020 at a discrete point a distance d from the point engaged by each immediately adjacent filament 1005. In some embodiments, the points of engagement may comprise of series of pre-marked locations specifically identified, for example, by a physical marker. In other embodiments, the points of engagement may further comprise a physical feature such as micro-features, texturing, grooves, notches, or other projections. Grooves 1066 are illustrated extending axially on the external circumference of the drum 1060 of FIG. 51. As shown in FIG. 53, the catch mechanisms 1030a-e are initially positioned equidistant between adjacent filaments 1005a-j, i.e., catch mechanism 1030a is positioned between filaments 1005a and 1005b, catch mechanism 1030b is positioned between filaments 1005c and 1005d, catch mechanism 1030c is positioned between filaments 1005e and 1005f, catch mechanism 1030d is positioned between filaments 1005g and 1005h and catch mechanism 1030e is positioned between filaments 1005i and 1005j. Each catch mechanism 1030 is further positioned with hooks located beyond the circumference of the disc 1020.

To engage a first set of filaments 1005a, c, e, g, and i, actuators 1040a,b,c,d,e attached to catch mechanisms 1030a,b,c,d,e are actuated to move each catch mechanism 1030 a discrete distance in a generally radial direction toward the disc 1020. The distal end of each catch mechanism 1030a-e preferably engages filaments 1005a, c, e, g and i at a point beneath the plane of the circular disc 1020 as the filaments extend over the edge 1022 of the disc 1020. For example, once the hooks 1036a-e have been moved toward the disc 1020 in the direction C2 (shown specifically in relation to hook 1036e and actuator 1040e) such that the tip of each hook 1036a-e extends past the hanging filaments 1005a, c, e, g, and i, the disc 1020 is rotated clockwise, in the direction of arrow C3, to cause the hooks 1036a-e to contact filaments 1005a, c, e, g, and i.

Once the filaments 1005a, c, e, g, and i are contacted by the hooks 1036a-e of the catch mechanisms 1030a-e, the actuators 1040a-e attached to catch mechanisms 1030a-e are again actuated to retract the catch mechanisms 1030a-e in the direction of arrow C4 (shown specifically in relation to hook 1036e and actuator 1040e), engaging filaments 1005a, c, e, g, and i in hooks 1036a-e and moving engaged filaments 1005a, c, e, g, and i, away from circumferential edge 1022 of disc 1020 in a generally radial direction to a point beyond edge 1022 of disc 1020.

Next, the disc 1020 is rotated counter-clockwise a distance of 2d, in the direction of arrow C1, to cross engaged filaments 1005a, c, e, g, and i over unengaged filaments 1005b, d, f, h, and j. Alternatively, as discussed above, the same relative motion can be produced by rotating the actuators 1040a-e and catch mechanisms 1030a-e in the direction of arrow C3, instead of rotating the disc 1020 in the direction of C1.

Next, the actuators 1040a-e attached to the catch mechanisms 1030a-e are again actuated to move the catch mechanisms a discrete distance in a generally radial direction toward disc 1020, as indicated by arrow C2. The hooks 1036a-e are thereby moved toward disc 1020 such that the tip of each hook 1036a-e extends inside the circumference formed by the hanging filaments 1005a-j. This will again place filaments 1005a, c, e, g, and i in contact with the edge 1022 of the disc 1020 and release the filaments 1005a,c,e,g, and i in addition, when the disc 1020 is rotated in a counter-clockwise direction, the filaments 1005d, f, h, and j are engaged by the double hooks 1036a-d on the catch mechanisms 1030a-d. The same steps can then be repeated in the opposite direction to cross filaments 1005b, d, f, h, and j over the unengaged filaments 1005a, c, e, g, and i to interweave the filaments in a one over-one under pattern.

Figure 54A:
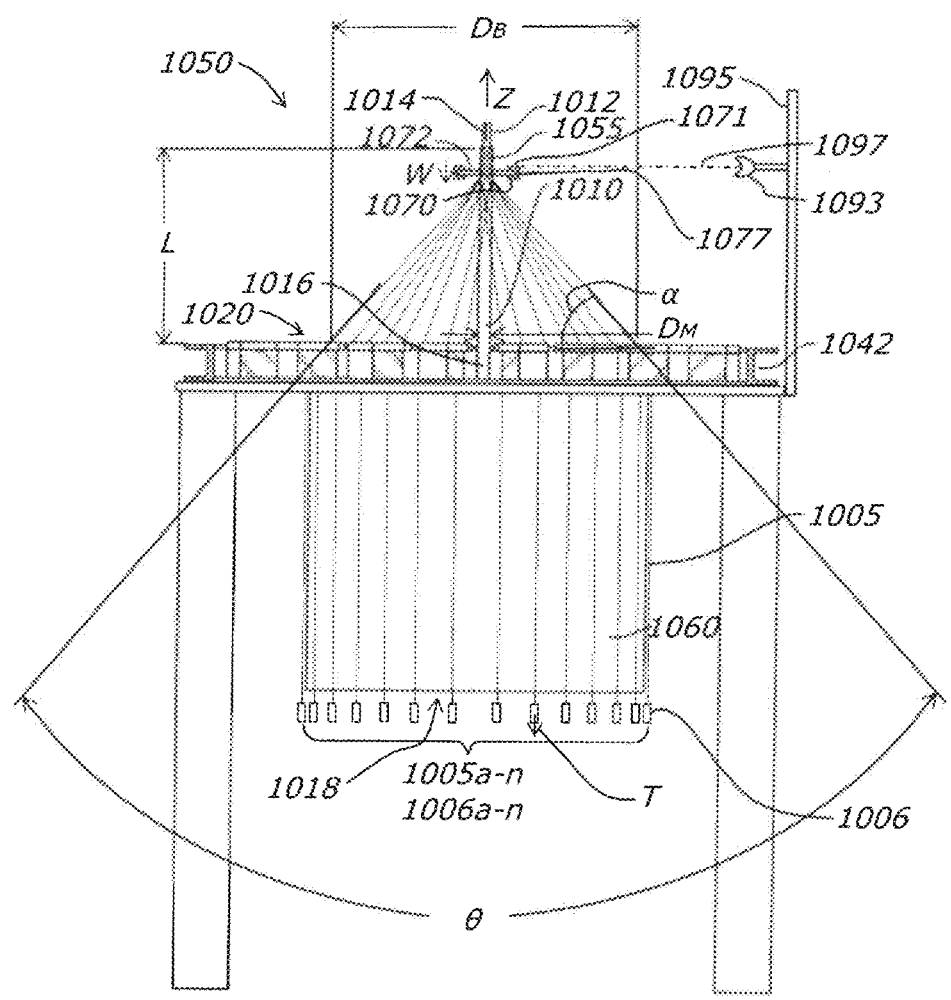
FIG. 54A illustrates a follower weight on the tubular braid being built on the mandrel of the embodiment shown in FIG. 52.

As shown in FIG. 54A, the filaments 1005a-n are thus progressively woven into braid 1055 about the mandrel 1010 from the uppermost tip 1012 towards the lower end 1016 of the mandrel 1010 extending from the circular disc 1020. The steps described create a braid 1055 in a one over-one under pattern, i.e., a diamond pattern, however, any number of braid patterns may be created by varying the subset of filaments 1005 engaged, the distances of rotation, and/or the pattern of repetition.

As shown in FIG. 54A, at the point where filaments 1005a-n converge to form the braid, i.e., the fell or braid point, a follower weight 1070 is used in combination with mandrel 1010 to affect the dimension and shape of the tubular braid (along with other important factors such as the number of filaments, the transverse dimension of the filaments, and the braiding pattern). A follower weight 1070, for example an adjustable former ring, can help to control the outside diameter of the braid 1055 and the mandrel 1010 helps to control the inside diameter. Ideally, the follower weight 1070 inner diameter is slightly larger than the outer cross section of mandrel 1010 approximating the diameter of the braid 1055. For example, about one-half millimeter to three-quarters of a millimeter larger. In this way, follower weight 1070 pushes the braided filaments 1005a-n a short distance to the mandrel 1010 with a short path of travel so that braid 1055 is pulled tightly against the mandrel 1010, thereby producing a uniform braid 1055 with high structural integrity. A follower weight 1070 having an adjustable inner diameter 1072, can be adjusted to closely match the outer diameter of selected mandrel 1010 and used to pull the braid 1055 tightly against the mandrel 1010. The adjustable follower weight 1070 is made by providing an adjustable inner diameter 1072, for example created by a plurality of overlapping leaves (not shown) in the form of an iris, which can be adjusted to provide a range of inner diameters. Such adjustable former rings are known in the art and more detail regarding the construction of such adjustable rings can be found in U.S. Pat. No. 6,679,152, entitled "Forming Ring with Adjustable Diameter for Braid Production and Methods of Braid Production," issued on Jan. 20, 2004.

Alternatively, a fixed follower weight having a predetermined and non-adjustable inner diameter that closely matches the outer diameter of mandrel 1010 can be used to pull the braid 1055 tightly against mandrel 1010. In some embodiments, the follower weight, may be not be significantly weighted. In other embodiments, the follower weight may be significantly weighted a specific amount, to provide an additional force pushing down on the filaments 1005a-n as they are pulled against the mandrel 1010 to form the braid 1055. For example, the follower weight 1070 may include a weight of between about 100 grams to 1000 grams, alternatively of between about 150 grams to 500 grams, depending on the type and size of filaments 1055 used, to provide an additional downward force on the filaments 1005a-n pulled through the follower weight 1070 and as pushed against the mandrel 1010 to create the braid 1055.

Figure 51:
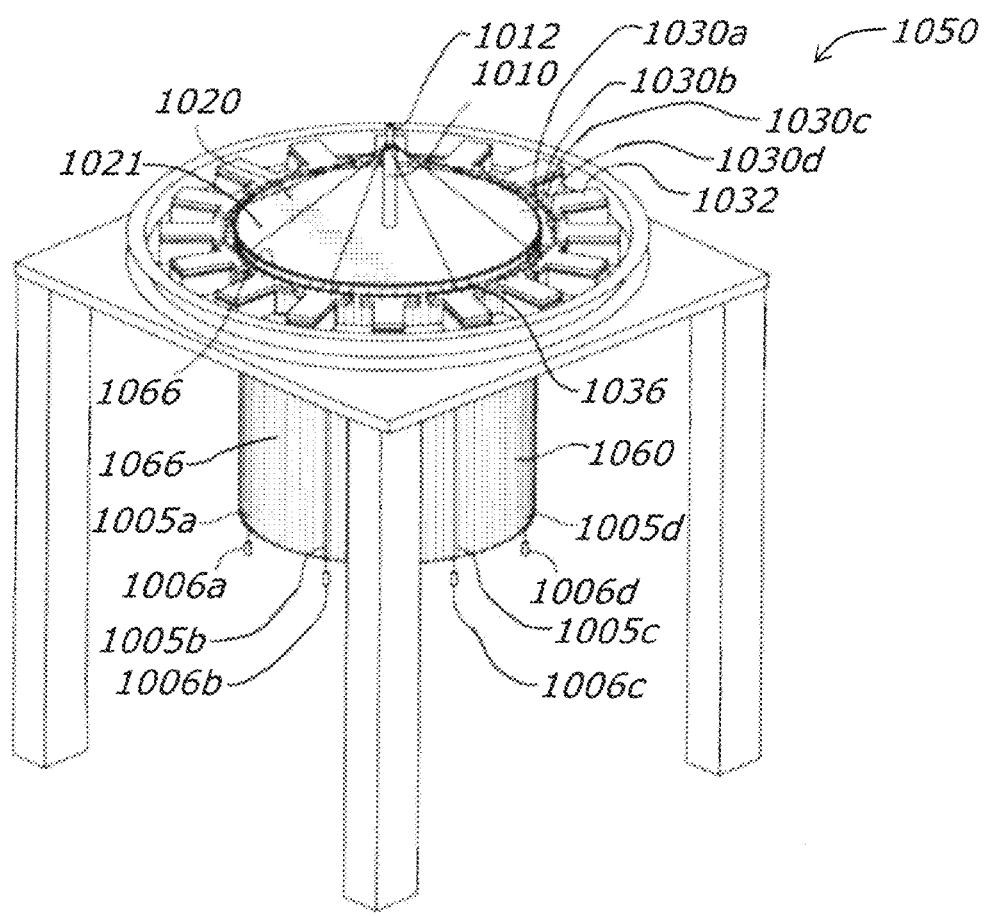
FIG. 51 illustrates an embodiment of a braiding device for braiding a plurality of filaments in a braided tubular member according to the present invention.
Figure 52:
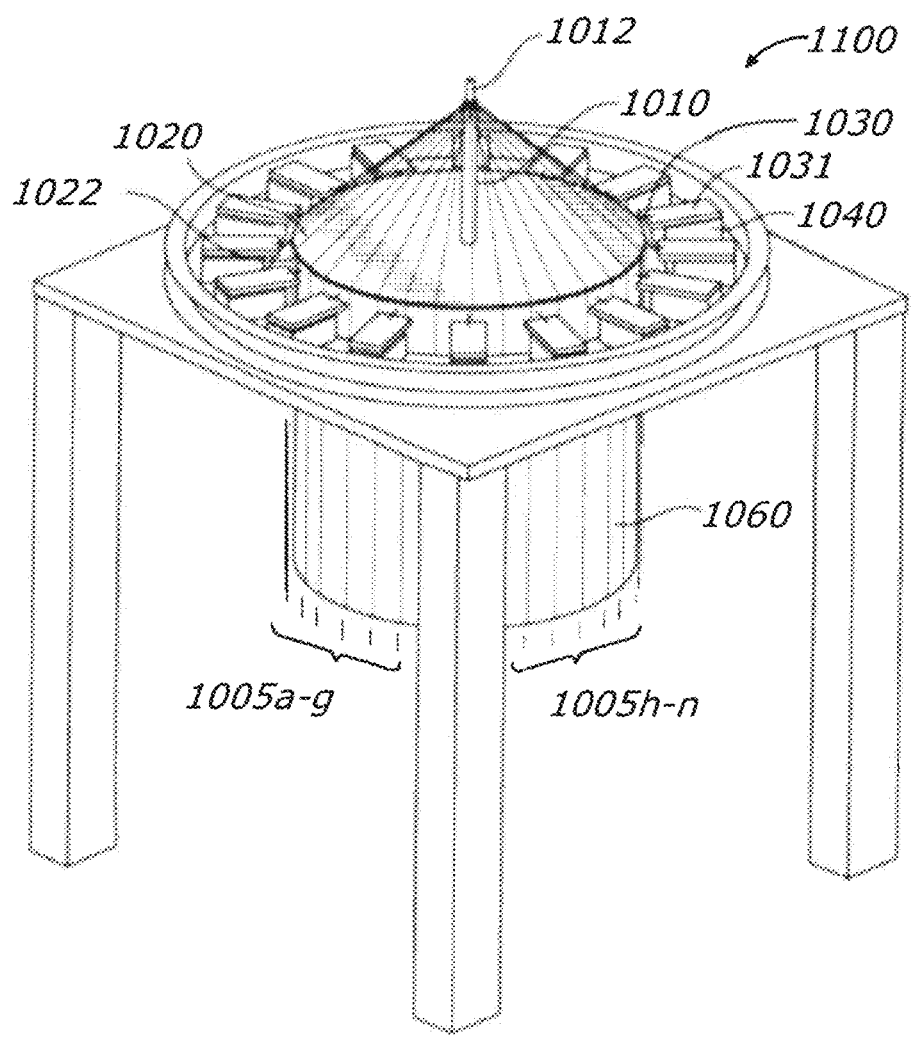
FIG. 52 illustrates another embodiment of a braiding device for braiding a plurality of filaments in a braided tubular member according to the present invention.

While in the braiding machine 1100 of FIG. 52, the catch mechanisms 1030 having double-headed hooks 1036 are secured to a moveable surface 1031 of each actuator 1040, the braiding machine 1050 of FIG. 51 comprises actuators 1040 having moveable rakes 1032, each rake 1032 having multiple double-headed hooks 1036, for example four double-headed hooks 1036.

FIGS. 51 and 54A illustrate a plurality of tensioning elements 1006a-n that are coupled to the end of each filament 1005a-n in order to control the tension in each filament 1005 during the braiding process. The tensioning elements 1006a-n may comprise weights attached to the end of each filament 1005, or may comprise any other tensioning element known in the art for applying between about 2 to 20 grams of weight, or alternatively between about 8 to 16 grams of weight, to each of the individual filaments 1005. Tensioning elements 1006a-n are sized to fit in the plurality of grooves 1066 on drum 1060. For example, each tensioning element 1006 may comprise an elongate cylindrical weight as illustrated in FIGS. 51 and 54A. Tensioning elements 1006a-n are separate for each filament 1005a-x and are individually connected to each filament 105a-x. Therefore the amount of tension applied can be varied for each filament 1005a-x. For example, a larger tensioning element 1006 can be attached to the smaller diameter filaments 1005 to apply more tension to the smaller diameter wires 1007 relative to the larger diameter wires 1007. The ability to individually tension each filament 1005 creates an accurate tensioning system that improves the uniformity and integrity of the braid 1055 and enables the braiding machine 1050, 1010 to operate with multiple diameter wires 1007. In some embodiments, the filaments 1005 may comprise a high strength nickel-titanium alloy, such as nickel-titanium-tungsten (Ni—Ti—W).

Figure 54C:
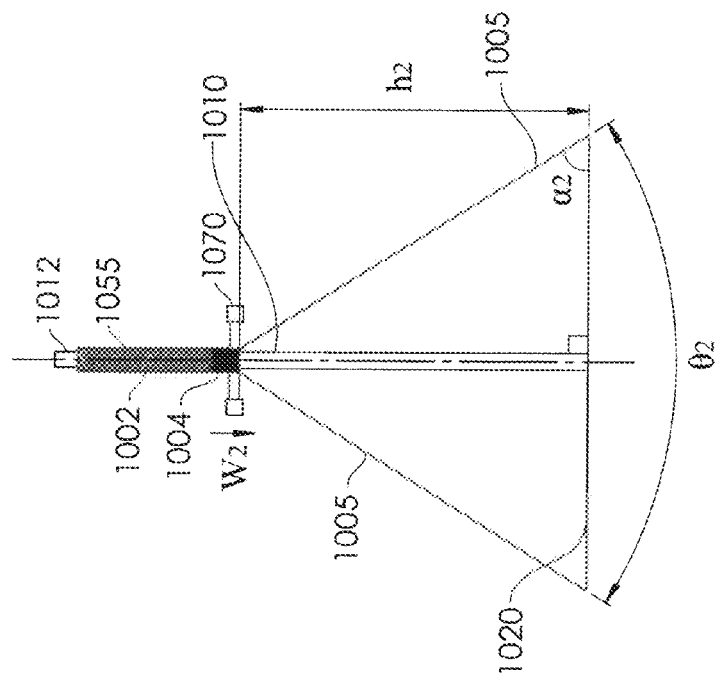
FIG. 54C is a detail of an upper portion of the braiding device of FIG. 54A with a first weight $W_2$.
Figure 54B:
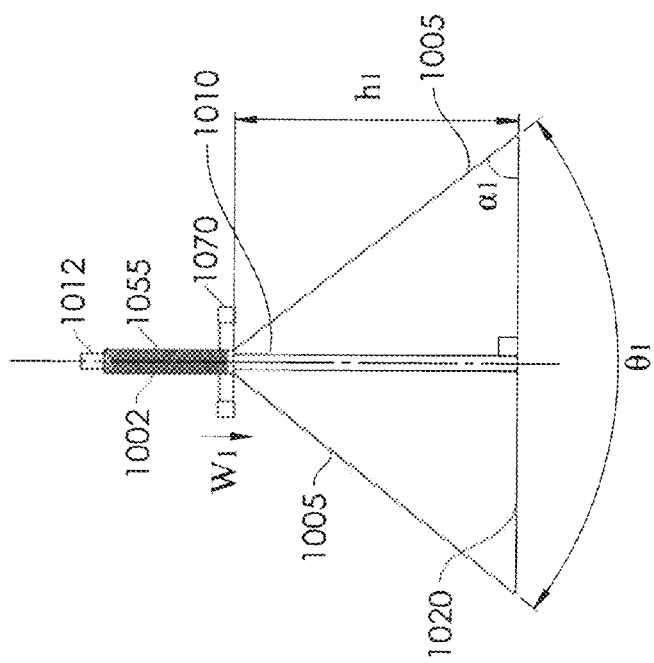
FIG. 54B is a detail of an upper portion of the braiding device of FIG. 54A with a first weight $W_1$.

Because of the variety of embodiments of braided devices that may be manufactured on the braiding machines 1050, 1010, the dimensions of the tubular braid 1055 can vary significantly. Some parameters that may be varied in order to produce the desired device or component for a device include mandrel 1010 diameter, filament 1005 diameter, number of filaments 1005, number of total crossings per unit length (i.e., pics per inch or pics per cm), and total length braided. FIGS. 54A-54C illustrates key braiding machine dimensions that can be affected by varying these parameters. For example, as the number of filaments 1005 increases, the diameter $D_B$ at which the hooks 1036 engage the filaments 1005 increases, because of the requirement of fitting all of the actuators 1040 and catch mechanisms 1030 around a circumference. Additionally, the included angle (θ) increases. This increase in the included angle (θ) is also affected, though to a much lesser extent, by a decrease in the diameter $D_M$ of the mandrel 1010. As the braid 1055 is made, the mandrel 1010 is configured to telescopically extend from the braiding machine 1050 in the direction Z, for example, indexing or jogging as an electronic sensor, such as an optical sensor 1093 (FIG. 54A) senses the progress of the braid, for example by the location of the follower weight 1070, 1075. For example, the optical sensor 1093 may be located on a post 1095 extending from the braiding machine 1050, and its sight line 1097 aimed at a side 1077 of the follower weight 1070. As long as the side 1077 of the follower weight 1070 is sensed by the optical sensor 1093, the mandrel 1010 is not given a command (for example from a controller) to axially extend. When, however, braiding has progressed sufficiently so that an upper edge 1071 of the follower weight 1070 falls below the sight line 1097, the controller gives a command to extend or index the mandrel 1010 upward, until the side 1077 of the follower weight 1070 is again within the sight line 1097. In reality, the effective included angle (θ), which is affected by the follower weight 1070, may be varied by controlling a variety of parameters: the effective weight imparted by the follower weight 1070, the rate of linear extension of the mandrel 1010 in the direction Z, and to a lesser extent, the effective tension created in the filaments by the tensioning elements 1006. One or more of these parameters may be purposely manipulated during the braiding process in order to create components having variable braid densities, such as the braided tubular member 1000 illustrated in FIGS. 50A-50D.

Cone angle (CA), α, is often the angle recorded in conjunction with the monitoring and operation of braiding machines 1050, 1100, instead of the included angle (θ) (FIG. 54A). Cone angle (α) is related to the included angle (θ) by the following equation:

$$CA=\alpha=90°-\theta/2$$

where α is the angle between horizontal (face of the disc 1020) and the extending filament 1005 at the point of engagement of the filament 1005 (at the circumferential edge 1022 of the disc 1020).

Angle α may be measured, for example with a mechanical or electronic level pressed along a portion of the extending filament 1005.

As seen in FIG. 50A, a braided tubular member 1000 having at least two distinct braided portions: a first braided portion 1002 having a first braid density ($BD_1$) and a second braided portion 1004 having a second braid density ($BD_2$), wherein the second braid density ($BD_2$) is different from the first braid density ($BD_1$), may be constructed, for example in the following manner. A plurality of filaments 1005 is loaded onto the mandrel 1010, and an initial tension $T_1$ is applied on each of a first subset of the filaments 1005 and on a second subset of the filaments 1005. For example weights having a weight of about 2 to about 20 grams, or more particularly about 8 to about 16 grams, or around 12 grams. A follower weight 1070 or another similar weighted structure is then placed over the filaments 1005 and the mandrel 1010. The follower weight 1070 has an inner diameter that closely matches a profile of the plurality of filaments over the mandrel and has weight $W_1$. A plurality of actuators 1040 are operated to engage the first subset of filaments 1005 and to move the engaged filaments 1005 in a generally radial direction to a radial position beyond the circumferential edge of the circular disc 1020. Either the circular disc 1020 or the plurality of actuators 1040 are then rotated (or both), thereby rotationally displacing the second subset of filaments 1005 and the first subset of filaments 1005 in relation to one another a discrete distance and crossing the filaments 1005 of the first subset over the filaments 1005 of the second subset. The plurality of actuators 1040 are then operated to move the first subset of filaments 1005 in a generally radial direction toward the circumferential edge of the circular disc 1020, wherein each filament 1005 in the first subset engages the circumferential edge 1022 of the circular disc 1020 at a point of engagement that is a circumferential distance from its previous point of engagement. The plurality of actuators 1040 are then operated to engage the second subset of filaments 1005 and to move the engaged filaments 1005 in a generally radial direction to a radial position beyond the circumferential edge of the circular disc 1020. Either the circular disc 1020 or the plurality of actuators 1040 are then rotated (or both), thereby rotationally displacing the second subset of filaments 1005 and the first subset of filaments 1005 in relation to one another a discrete distance and crossing the filaments 1005 of the second subset over the filaments 1005 of the first subset. The plurality of actuators 1040 are then operated to move the second subset of filaments 1005 in a generally radial direction toward the circumferential edge of the circular disc 1020, wherein each filament 1005 in the second subset engages the circumferential edge 1022 of the circular disc 1020 at a point of engagement that is a circumferential distance from its previous point of engagement. The steps above are repeated to form a tubular braid having a first braid density $BD_1$. The follower weight 1070 is then replaced with a different follower weight having a different weight, or is modified to that it has a different weight $W_2$, or any equivalent manner so that the effect of the follower weight 1070 on the filaments 1005 extending from the tubular braid is changed, for example, changing the effective cone angle (CA) and the included angle ($\theta$). The above steps are repeated to continue to form the tubular braid, but at a second braid density $BD_2$, different from the first braid density $BD_1$.

For a braided tubular member 1000 having 144 0.001 inch nitinol filaments, braided in a one over one pattern, a 5 mm inner diameter variable braid having two distinct portions, having a first braid density $BD_1$ and a second braid density $BD_2$, a weight $W_1$ of 263 grams and a weight $W_2$ of 175 grams may be used, or a weight $W_1$ about 50% higher than weight $W_2$ (FIGS. 54B-54C). The portion braided using the weight $W_1$ of 263 grams will be braided with a comparably larger included angle ($\theta_1$) and a comparably smaller cone angle ($\alpha_1$), and will thus have a lower braid density BD, than the portion braided using the weight $W_2$ of 175 grams. The portion braided using the weight $W_2$ of 175 grams will thus be braided with a comparably smaller included angle ($\theta_2$) and a comparably larger cone angle ($\alpha_2$). Weight $W_1$, may also be more than 50% higher than weight $W_2$. Along with the change from weight $W_1$ to weight $W_2$, the initial tension $T_{i1}$ on the filaments may be changed to a secondary tension $T_{s1}$. For example, by attaching additional weights (tensioning elements 1006) to one or more of the filaments 1005, or by removing at least a portion of weights (tensioning elements 1006) that are attached to one or more of the filaments 1005. A first braided portion 1002 having a first braid density $BD_1$ is shown being formed in FIG. 54B with weight $W_1$ in place, as the mandrel 1010 indexes in the positive Z direction (FIG. 54A). Weight $W_1$ is replaced by lighter weight $W_2$ in FIG. 54C, and a second braided portion 1004 having a second braid density $BD_2$ is formed, the second braid density $BD_2$ higher than the first braid density $BD_1$.

Figure 54D:
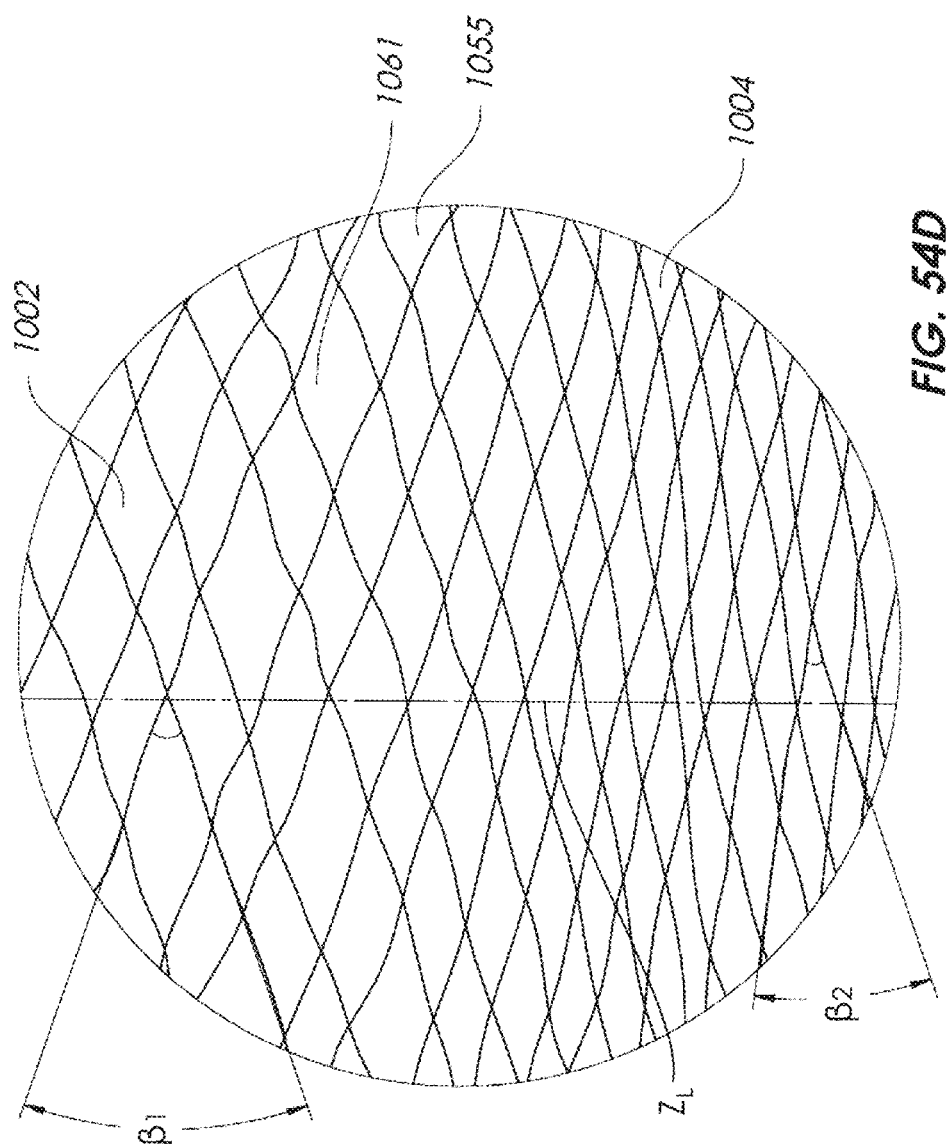
FIG. 54D is a detail of a section of the tubular braid.

The tubular braid 1055 illustrated in FIG. 54D is oriented between a first end and a second end along axis $Z_L$. The tubular braid 1055 has a plurality of diamond shapes 1061. The angle $\beta_1$ oriented at the 3 o'clock position within the first braided portion 1002 is greater than the angle $\beta_2$ oriented at the 3 o'clock position within the second braided portion 1004. In some embodiments, the angle $\beta_2$ may be between about 25° and about 45°, or between about 30° and about 40°, or about 35°. In some embodiments, the angle $\beta_1$ may be between about 35° and about 65°, or between about 45° and about 55°, or about 50°.

A mesh device 1200 made from braided tubular member 1000 and having a substantially spherical expanded configuration is illustrated in FIG. 55 in its expanded configuration. The mesh device 1200 has a first braided portion 1202 having a first average braid density $BD_{avg1}$ and a second braided portion 1204 having a second average braid density $BD_{avg2}$. The second average braid density $BD_{avg2}$ is greater than the first average braid density $BD_{avg1}$. The braid density BD transitions from the first braided portion 1202 to the second braided portion 1204 over a transition zone TZ 1206. In some embodiments, the transition zone TZ 1206 may be less than about two millimeters in length (or height), or less than about one millimeter in length. In some embodiments, the transition zone TZ 1206 may be as small as about 300 microns in length, or even as small as about 100 microns in length. In some embodiments, the ratio between the length (height) of the transition zone TZ 1206 and the total length (height) of the mesh device 1200 may be about 0.5% to about 20%, or about 1% to about 15%, or about 1% to about 10% or about 3% to about 8%.

In a mesh device 1200 made from a braided tubular member 1000 and having a first braided portion 1202 and a second braided portion 1204, it may be desirable to have a first braided portion 1202 braid density $BD_1$ in the range of about 0.10 to about 0.20, or more particularly from about 0.10 to about 0.15. Furthermore, it may be desirable to have a second braided portion 1204 braid density $BD_2$ in the range of about 0.15 to about 0.40, or more particularly from about 0.17 to about 0.30. The second braided portion 1204 furthermore may have a plurality of openings having an average hydraulic diameter $D_H$ of 200 µm or less. The ratio of second braided portion 1204 braid density $BD_2$ to first braided portion 1202 braid density $BD_1$, or $BD_2/BD_1$, may desirably be in the range of about 1.25 to about 5.0, or more particularly between about 1.25 and about 2.5, or even more particularly between about 1.50 and about 2.0. Referring to FIGS. 7 and 8, in some embodiments, a majority of the plurality of openings or pores 64 in the second braided portion 1204 have a circular shape (100) diameter of between about 0.005 inches and about 0.010 inches. In some embodiments, a majority of the plurality of openings or pores 64 in the second braided portion 1204 have a circular shape (100) diameter of between about 0.006 inches and about 0.009 inches. In some embodiments, a majority of the plurality of openings or pores 64 in the second braided portion 1204 have a circular shape (100) diameter of between about 0.007 inches and about 0.008 inches. In some embodiments, the diameter of the pore in the first braided portion 1202 may be between about 300 µm and about 900 µm, or between about 300 µm and about 700 µm, or between about 300 µm and about 500 µm. In some embodiments, the diameter of the pore in the second braided portion 1204 may be between about 50 µm and about 200 µm, or between about 100 µm and about 200 µm.

The mesh device 1200 has a proximal end 1208 and a distal end 1210, the first braided portion 1202 adjacent the distal end 1210 and the second braided portion 1204 adjacent the proximal end 1208. Individual filaments 1212 that constitute the braided tubular member 1000 from which the mesh device 1200 is made are secured together at the proximal end 1208 by a marker band 1214, for example, a marker band comprising a radiopaque material such as platinum or a platinum alloy. Alternatively, the individual filaments 1212 may be held together by welding, adhesives, epoxies or any other joining method. The adhesive or epoxy may be doped with radiopaque material, such as tantalum, in order to increase visualization. The mesh device 1200, when used for the purpose of treating a vascular defect such as a cerebral aneurysm, is placed into the aneurysm so that the second braided portion 1204 covers the neck of the aneurysm. The second average braid density $BD_{avg2}$ of the second braided portion 1204 is above an average braid density $BD_{avg}$ that is in a range that effectively stagnates the flow of blood into the aneurysm when the mesh device 1200 is expanded within the aneurysm. In addition, the average hydraulic diameter $D_H$ of each of the diamond-shaped openings 1011 at the most expanded region 1205 of the second braided portion 1204 is 200 µm or less. The average hydraulic diameter $D_H$ of each of the diamond shaped openings 1011 at the most expanded region 1203 of the first braided portion 1202 may be greater than 300 µm, or even greater than 500 µm, with the mesh device 1200 retaining its mechanical characteristics, such as radial strength.

The filaments 1212 at the distal end 1210 of the mesh device 1200 are not gathered together in the same manner as at the proximal end 1208, but rather are free, unconnected ends 1216. Each end 1216 may be simply the bare termination of the particular filament 1212, or alternatively, it may be coated or capped with an adhesive or epoxy, in order to make it relatively more blunt.

A mesh device 1300 made from braided tubular member 1000 and having a more elongate expanded configuration than the mesh device 1200 of FIG. 55 is illustrated in FIG. 56 in its expanded configuration. The mesh device 1300 has a first braided portion 1302 having a first average braid density $BD_{avg1}$ and a second braided portion 1304 having a second average braid density $BD_{avg2}$. The second average braid density $BD_{avg2}$ is greater than the first average braid density $BD_{avg1}$. The braid density BD transitions from the first braided portion 1302 to the second braided portion 1304 over a transition zone TZ 1306. The mesh device 1300 has a proximal end 1308 and a distal end 1310, the first braided portion 1302 adjacent the distal end 1310 and the second braided portion 1304 adjacent the proximal end 1308. Individual filaments 1312 that constitute the braided tubular member 1000 from which the mesh device 1300 is made are secured together at the proximal end 1308 by a marker band 1314. The filaments 1312 at the distal end 1310 of the mesh device 1300 are not gathered together in the same manner as at the proximal end 1308, but rather are free, unconnected ends 1316. Each end 1316 may be simply the bare termination of the particular filament 1312, or alternatively, it may be coated or capped with an adhesive or epoxy, in order to make it relatively more blunt. The mesh device 1300, when used for the purpose of treating a vascular defect such as a cerebral aneurysm, is placed into the aneurysm so that the second braided portion 1304 covers the neck of the aneurysm. The braid density $BD_{avg2}$ at the most expanded region 1305 of the second braided portion 1304 is above an average braid density $BD_{avg}$ that is in a range that effectively stagnates the flow of blood into the aneurysm when the mesh device 1300 is expanded within the aneurysm. The braid density ranges and braid density ratios discussed in conjunction with the mesh device 1200 of FIG. 55 also apply here. In addition, the average hydraulic diameter $D_H$ of each of the diamond-shaped openings 1011 at the most expanded region 1305 of the second braided portion 1304 is 200 µm or less. The average hydraulic diameter $D_H$ of each of the diamond shaped openings 1011 at the most expanded region 1303 of the first braided portion 1302 may be greater than 300 µm, or even greater than 500 µm, with the mesh device 1300 retaining its mechanical characteristics, such as radial strength.

As illustrated in FIGS. 57 and 58, both mesh device 1200 and mesh device 1300, when used for the embolization of a cerebral aneurysm, are deployed so that distal ends 1210, 1310 stop short of, and avoid touching the dome 161 of aneurysm 160. This may be especially useful during the embolization of an aneurysm 160 whose dome 161 recently ruptured, because the mesh device 1200, 1300 will be less likely to rub along a healed rupture site 163, as depicted in FIG. 57. The direct contact of an implant with a healed rupture site 163 may shear off or force open a fibrous healed cap 165.

The advantages of braiding a mesh device 1200, 1300 having a relatively high braid density BD at the second braided portion 1204, 1304, which is configured to be placed adjacent the neck 167 of the aneurysm 160, have been described. Additionally, it is advantageous for the radially constrained, elongated state of the mesh device 1200, 1300 to be configured for delivery within a microcatheter having as small of an outer diameter, and thus, as small of an inner limen diameter as possible. Microcatheters having an inner lumen diameter of less than 0.033 inches, or less than 0.020 inches, and as small as 0.017 inches or less can be tracked into very distal and very tortuous vasculature. A mesh device 1200, 1300 made from a single layer braided tubular member 1000 can be radially constrained into a smaller diameter than a mesh device made from dual layer braided tubular members. The higher average braid density $BD_{avg2}$ of the second braided portion 1204, 1304 contains the smaller effective opening size in a dual layer mesh device, but does not have two layers that need to be constrained. Additionally, the relatively lower braid density $BD_{avg1}$ of the first braided portion 1202, 1302 may allow the mesh device 1200, 1300 to be radially constrained into a smaller diameter, and fit through a smaller microcatheter lumen than a mesh device having a single layer braided portion whose entire length has a higher average braid density. The capability of forming a single layer mesh device 1200, 1300 made from a braided tubular member 1000 having a variable braid further allows the total number of filaments to be dropped, thus further reducing the constrained diameter of the mesh device, and allowing it to be placed in a smaller microcatheter lumen. A mesh device 1200, 1300 made from a single braided tubular member 1000 having 108 filaments 1005 or fewer, each having a transverse dimension of about 0.0005 inches to about 0.001 inches, and braided in a manner so that it has a variable braided structure having a first braided portion and a second braided portion, the second braided portion having a braid density $BD_2$ that is greater than the braid density $BD_1$ of the first braided portion, can be constrained and passed through a microcatheter having an inner lumen diameter of 0.017 inches.

Referring particularly to FIG. 57, axis r represents the radial location at the neck 167 of the aneurysm 160. At the center of the neck, r=0 and at the outer extents of the neck, r is at a maximum. As illustrated, a typical orientation of the mesh device 1200 is such that a less expanded portion 1207 of the second braided portion 1204 is closer to the center of the neck (i.e., closer to r=0) and the most expanded portion 1205 of the second braided portion 1204 is at an outer extent where r is a maximum, or in the case of FIG. 57, beyond the outer extent of the neck 167. The braid density at the most expanded portion 1205 of the second braided portion 1204 is inherently higher than the braid density at a less expanded portion 1207 of the second braided portion 1204. Also, it is common in a high flow basilar tip aneurysm that the blood flow impingement velocity $V_1$ at a portion toward the center of the neck 167 (i.e., closer to r=0) is higher than the blood flow impingement velocity $V_2$ toward the outer extents of the neck (i.e., closer to r=maximum). Therefore, it is desired to form a mesh device 1200 such that the hydraulic diameter $D_H$ of openings 1011 at the most expanded portion 1205 of the second braided portion 1204 is 200 µm or less. In this way, all or virtually all of the openings 1011 in the second braided portion 1204 will have a hydraulic diameter $D_H$ of 200 µm or less. In certain anatomies, due to vessel tortuosity, disease, or other reasons, the blood flow impingement velocity $V_2$ may be higher than the blood flow impingement velocity $V_1$. In these cases, the hydraulic diameter $D_H$ will still be 200 µm or less at the maximum impingement velocity location.

The mesh device 1200, 1300 may be made from one, two, three or even more different types of filaments 1005, including different filament materials or filament transverse dimensions. In one particular three filament combination embodiment, larger diameter wires (for example 0.001 inches to 0.002 inches) may be included to supply mechanical support. Smaller diameter wires (0.0005 inches to 0.001 inches) may be included to assure a higher braid density portion may be made, for example the portion configured to be placed adjacent the neck 167 of the aneurysm 160. There may also be "medium" filaments with diameters between around 0.00075 inches and 0.00125 inches, to supply radiopacity. For example, these filaments may be made from platinum or platinum alloy, or may be drawn filled tubes (DFT) which comprise an outer shell of nickel titanium and an inner core of platinum or platinum alloy. The "medium" filaments may be included in variable percentages (in relation to the total number of filaments) in order to achieve a specific stiffness characteristic. The "medium" filaments may also be included in a particular percentage to impart the desired minimum tensile strength. Composite wire technology including Cobalt-Chromium (CoCr) may be used. For example, DFT filaments comprising Cobalt-Chromium (CoCr) in the external shell with platinum or platinum alloy cores supply strength, stiffness and radiopacity. Nickel Titanium shells with Cobalt-Chromium cores supply formability and strength.

A mesh device 1400 having a substantially spherical expanded configuration and a substantially closed distal apex 1415 is illustrated in FIG. 59 in its expanded configuration. The mesh device 1400 has a first braided portion 1402 having a first average braid density $BD_{avg1}$ and a second braided portion 1404 having a second average braid density $BD_{avg2}$. The second average braid density $BD_{avg2}$ is greater than the first average braid density $BD_{avg1}$. The braid density BD transitions from the first braided portion 1402 to the second braided portion 1404 over a transition zone TZ 1406.

The mesh device 1400 has a proximal end 1408 and a distal end 1410, the first braided portion 1402 adjacent the distal end 1410 and the second braided portion 1404 adjacent the proximal end 1408. Individual filaments 1412 that constitute an alternative braided member from which the mesh device 1400 is made are secured together at the proximal end 1408 by a marker band 1414, for example, a marker band comprising a radiopaque material such as platinum or a platinum alloy. Alternatively, the individual filaments 1412 may be held together by welding, adhesives, epoxies or any other joining method. The adhesive or epoxy may be doped with radiopaque material, such as tantalum, in order to increase visualization. The mesh device 1400, when used for the purpose of treating a vascular defect such as a cerebral aneurysm, is placed into the aneurysm so that the second braided portion 1404 covers the neck of the aneurysm. The second average braid density $BD_{avg2}$ of the second braided portion 1404 is above an average braid density $BD_{avg}$ that is in a range that effectively stagnates the flow of blood into the aneurysm when the mesh device 1400 is expanded within the aneurysm. The braid density ranges and braid density ratios discussed in conjunction with the mesh device 1200 of FIG. 55 also apply here. In addition, the average hydraulic diameter $D_H$ of each of the diamond-shaped openings 1011 at the most expanded region 1405 of the second braided portion 1404 is 200 µm or less. The average hydraulic diameter $D_H$ of each of the diamond shaped openings 1011 at the most expanded region 1403 of the first braided portion 1402 may be greater than 300 µm, or even greater than 500 µm, with the mesh device 1400 retaining its mechanical characteristics, such as radial strength.

Figure 61:
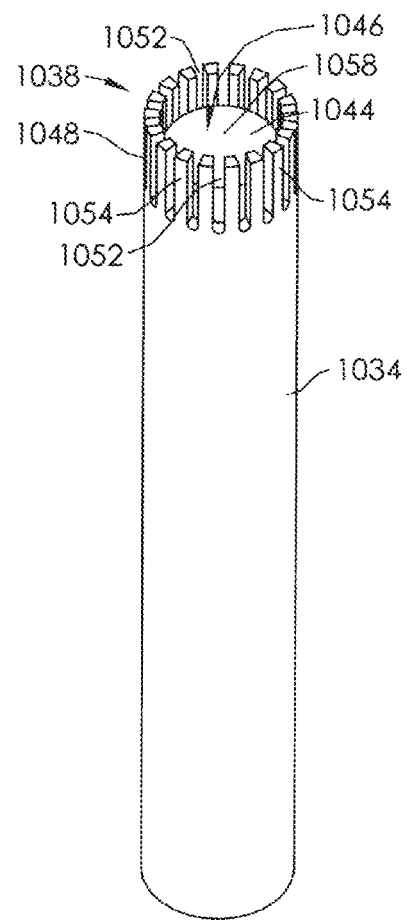
FIG. 61 is a castellated mandrel assembly used in the braiding process of the embodiments of the devices of FIGS. 58 and 59.
Figure 62:
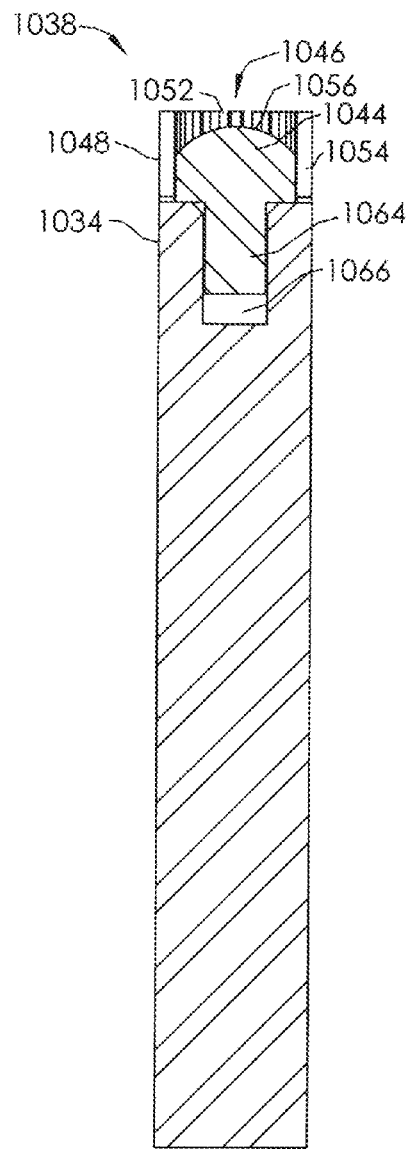
FIG. 62 is a section view of the castellated mandrel assembly of FIG. 61.

Turning to FIGS. 61 and 62, a castellated mandrel assembly 1038 is illustrated, and comprises a castellated mandrel 1034 having a radiused cap 1044 within its central cavity 1046. The castellated mandrel 1034 includes a cylindrical battlement-like structure 1048 having a plurality of slots, or crenels 1052, separated by a plurality of posts, or merlons 1054. The embodiment illustrated in FIGS. 61 and 62 comprises 18 crenels 1052 and 18 merlons 1054, however, alternative embodiments may include 27 crenels 1052 and 27 merlons 1054, or other quantities. The radiused cap 1044 has a convex radius 1056 whose surface 1058 is preferably contained within the portion of the central cavity 1046 surrounded by the battlement-like structure 1048. A pin 1064 extends from the radiused cap 1044, and extends into a hole 1066 within the castellated mandrel 1034. The radiused cap 1044 may be secured to the castellated mandrel 1034 by attaching the pin 1064 to the hole 1066 using a threaded screw, adhesive, epoxy, welding, or analogous methods. The radiused cap 1044 and the castellated mandrel 1034 may be made from rigid, durable materials, such as stainless steel.

Figures 63A, 63B:
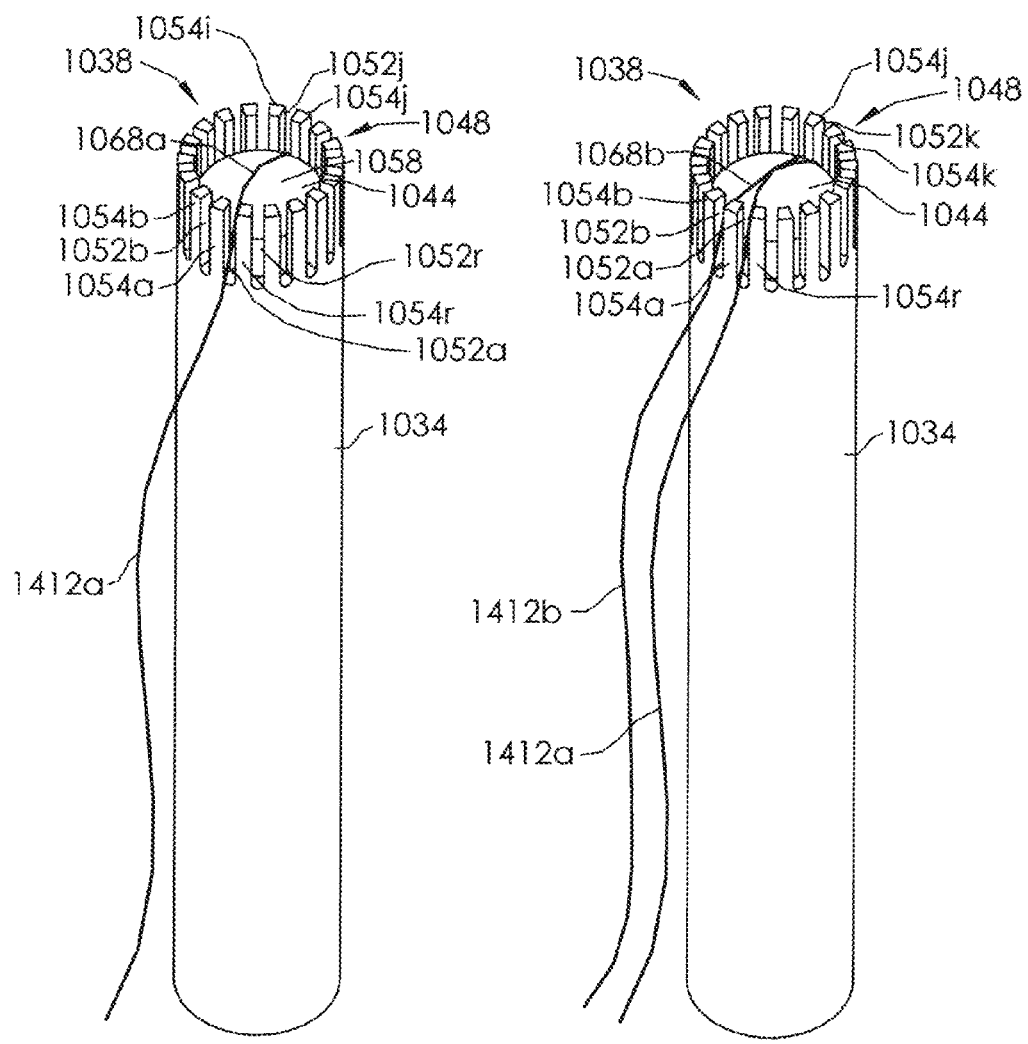
FIGS. 63A-63C illustrate the method of loading the castellated mandrel assembly of FIG. 61 for the braiding process for the device of FIG. 59.
Figure 63C:
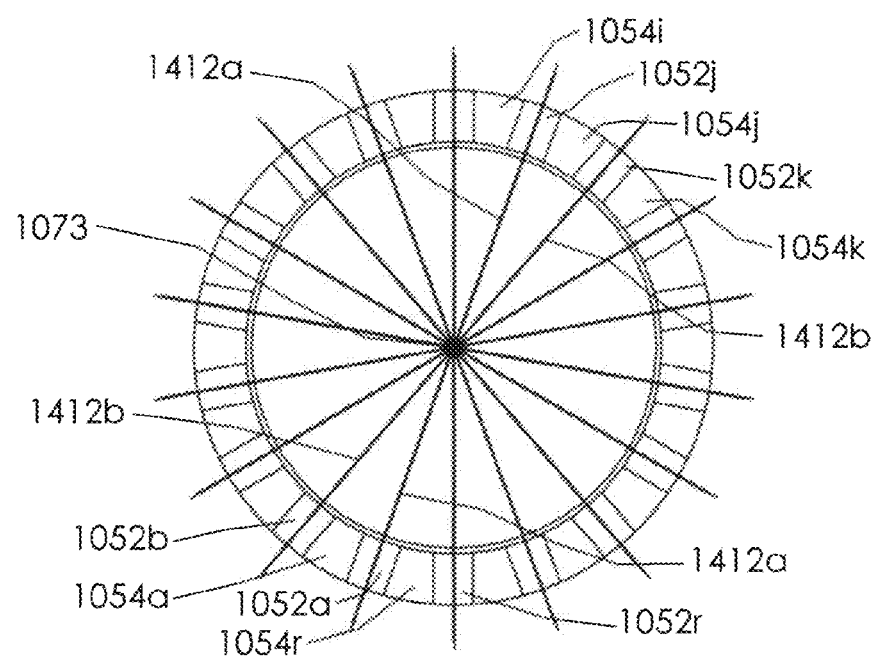

The loading of a castellated mandrel assembly 1038 for the process of constructing the mesh device 1400 of FIG. 59 is illustrated in FIGS. 63A-63C. Posts or merlons 1054a-r are circumferentially arrayed around the battlement-like structure 1048, with slots or crenels 1052a-r between each of the merlons 1054a-r. In FIG. 63A, a first filament 1412a is loaded in a downward direction into crenel 1052a (between merlons 1054r and 1054a) and crenel 1052j (between merlons 1054i and 1054j) and secured to the castellated mandrel assembly 1038. The first filament 1412a may be secured, for example, so that a central portion 1068a of the first filament 1412a is held snugly across the surface 1058 of the convex radius 1056 of the radiused cap 1044. In an 18-crenel embodiment of the castellated mandrel assembly 1038, the locations of crenel 1052a and 1052j are 180° from each other, approximating, for example, 12 o'clock and 6 o'clock locations on a clock face. However, other, non-180° configurations, such as the configuration of FIG. 63D, may be chosen for the filament 1412a, or subsequent filaments 1412 to be loaded. In FIG. 63B, a second filament 1412b is loaded in a downward direction into crenel 1052b (between merlons 1054a and 1054b) and crenel 1052k (between merlons 1054j and 1054k) and secured to the castellated mandrel assembly 1038. A central portion 1068b of the filament 1412b is crossed over the central portion 1068a of the first filament 1412a, and held snugly across the convex radius 1056 of the radiused cap 1044. This loading is continued until all filaments 1412 are loaded and secured to the castellated mandrel assembly 1038. Multiple filaments 1412 may be loaded into each of the crenels 1052, or only certain selected crenels 1052. After loading all of the filaments 1412 into the crenels 1052 and securing the filaments 1412 to the castellated mandrel assembly 1038, the filaments 1412 are ordered and extended radially, as are the filaments 1005 in FIGS. 51-54, and the braiding process is performed as previously described in relation to these figures. The resulting mesh device 1400 of FIG. 59 has substantially closed distal apex 1415, because of the manner in which the filaments 1412 are layered over each other at the radiused cap 1044. The mesh device 1400 of FIG. 59 may be made with, for example, 72 to 216 filaments 1412, but because the loading of the mandrel produces the equivalent of two filaments 1412 from a single piece of wire, there are only 36 to 108 pieces of wire required. The mesh device 1400 may have only the single marker band 1414, as no securing of wires is required at the distal end 1410. A mixture of platinum or platinum alloy filaments with Nickel-Titanium filaments may be chosen to add radiopacity to the mesh device 1400, especially at the distal end 1410 where there is no marker band 1414. Alternatively, drawn filled tubes (DFT) having a radiopaque (e.g., platinum or platinum alloy) core may be used. In both the mesh device 1400 of FIG. 59 and the mesh device 1500 of FIG. 60, filament diameters may range from about 0.0005 inches to about 0.002 inches, or from about 0.00075 inches to 0.00125 inches FIG. 63C illustrates a top view of the loaded castellated mandrel assembly 1038 of the mesh device 1400, made in conjunction with the method described in FIGS. 63A-63B. Because each of the filaments 1412 crosses a center crossing point 1073, the substantially closed distal apex 1415 of the mesh device 1400 includes many layers of filaments 1412 at this center crossing point 1073. However, shaping and heat forming of the mesh device 1400 can at least partially reform some or all of the filaments 1412 at the center crossing point 1073, spreading them out in order to lessen the bulk at the center crossing point.

Figure 63D:
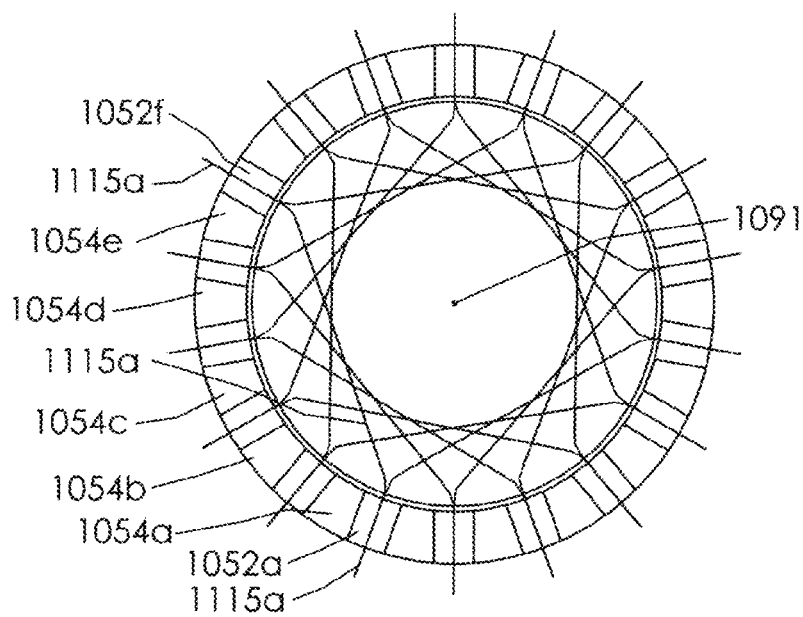
FIG. 63D illustrates an alternative embodiment for loading the castellated mandrel assembly of FIG. 61.

An alternative filament loading method is illustrated in FIG. 63D. Filaments 1115 are loaded in a staggered manner. Filament 1115a is loaded into crenels 1052a and 1052f; thus, it extends inside merlons 1054a, 1054b, 1054c, 1054d, and 1054e, and is held snugly across a portion of the convex radius 1056 of the radiused cap 1044. Filament 1115b is loaded into crenels 1052b and 1052g, and thus it extends inside merlons 1054b, 1054c, 1054d, 1054e, and 1054f, and crosses on top of filament 1115a. This is continued until all of the filaments 1115 are loaded, and the configuration of FIG. 63D is visible. In this embodiment, a central opening 1091 is formed, in contrast to the closed distal apex 1415 of the mesh device 1400. The size of the central opening 1091 can be varied, depending on both the diameter of the castellated mandrel 1034 at the battlement-like structure 1048, and the total number of crenels 1052 skipped when loading each filament 1115.

A mesh device 1500 having an open distal end 1510 is illustrated in FIG. 60 in its expanded configuration. The mesh device 1500 comprises a single layer braided tubular member having a first braided portion 1502 having a first average braid density $BD_{avg1}$ and a second braided portion 1504 having a second average braid density $BD_{avg2}$. The second average braid density $BD_{avg2}$ is greater than the first average braid density $BD_{avg1}$. The braid density BD transitions from the first braided portion 1502 to the second braided portion 1504 over a transition zone TZ 1506. The braid density ranges and braid density ratios discussed in conjunction with the mesh device 1200 of FIG. 55 also apply here.

The mesh device 1500 has a proximal end 1508 and a distal end 1510, the first braided portion 1502 adjacent the distal end 1510 and the second braided portion 1504 adjacent the proximal end 1508. Individual filaments 1512 that constitute an alternative braided tubular member from which the mesh device 1500 is made are secured together at the proximal end 1508 by a marker band 1514, for example, a marker band comprising a radiopaque material such as platinum or a platinum alloy. Alternatively, the individual filaments 1512 may be held together by welding, adhesives, epoxies or any other joining method. The adhesive or epoxy may be doped with radiopaque material, such as tantalum, in order to increase visualization. The mesh device 1500, when used for the purpose of treating a vascular defect such as a cerebral aneurysm, is placed into the aneurysm so that the second braided portion 1504 covers the neck of the aneurysm. The second average braid density $BD_{avg2}$ of the second braided portion 1504 is above an average braid density $BD_{avg}$ that is in a range that effectively stagnates the flow of blood into the aneurysm when the mesh device 1500 is expanded within the aneurysm. In addition, the average hydraulic diameter $D_H$ of each of the diamond-shaped openings 1011 at the most expanded region 1505 of the second braided portion 1504 is 200 µm or less. The average hydraulic diameter $D_H$ of each of the diamond shaped openings 1011 at the most expanded region 1503 of the first braided portion 1502 may be greater than 300 µm, or even greater than 500 µm, with the mesh device 1500 retaining its mechanical characteristics, such as radial strength.

Figures 64A, 64B:
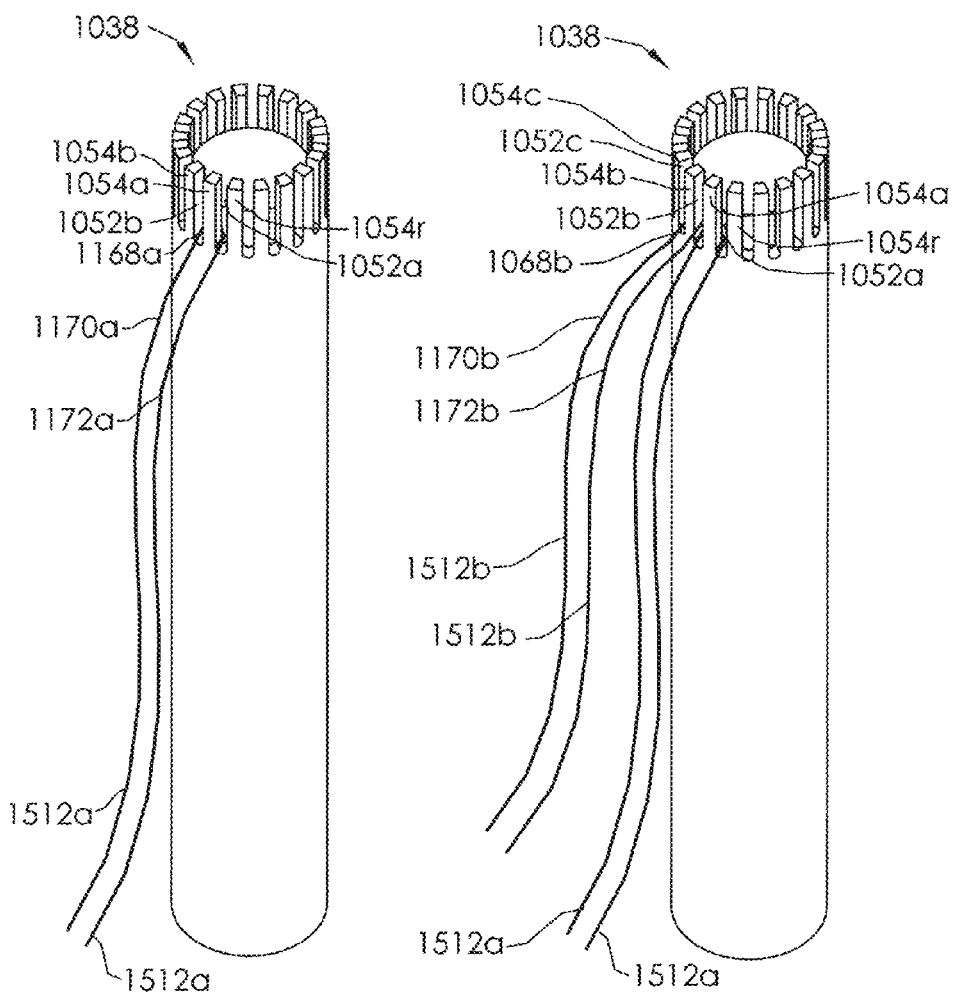
FIGS. 64A-64B illustrate the method of loading the castellated mandrel assembly of FIG. 61 for the braiding process for the device of FIG. 60.

An open portion 1518 at the distal end 1510 of the mesh device 1500 is surrounded by a plurality of loops 1516 that result from the initial loading of the filaments 1512 onto the castellated mandrel assembly 1038. The loading of a castellated mandrel assembly 1038 for the process of constructing a mesh device 1500 (FIG. 60) is illustrated in FIGS. 64A-64B. FIG. 64A, a first filament 1512a is loaded in a downward direction into crenel 1052a (between merlons 1054r and 1054a) and crenel 1052b (between merlons 1054a and 1054b). A central portion 1168a of the first filament 1512a is held snugly around the merlon 1054a and a first portion 1170a and a second portion 1172a of the filament 1512a are secured to the castellated mandrel assembly 1038. In FIG. 64B, a second filament 1512b is loaded in a downward direction into crenel 1052b (between merlons 1054a and 1054b) and crenel 1052c (between merlons 1054b and 1054c). A central portion 1168b of the second filament 1512b is held snugly around the merlon 1054b and a first portion 1170b and a second portion 1172b are secured to the castellated mandrel assembly 1038. This loading is continued until all the filaments 1512 are loaded and secured to the castellated mandrel assembly 1038. Multiple filaments 1512 may be loaded around each of the merlons 1054, or only certain selected merlons 1054. After loading all of the filaments 1512 into the crenels 1052 and securing the filaments 1512 to the castellated mandrel assembly 1038, the filaments 1512 are ordered and extended radially, as are the filaments 1005 in FIGS. 51-54, and the braiding process is performed as previously described in relation to these figures. A plurality of loops 1516, as shown in FIG. 60, result from the central portions 1168 of the filaments 1512 that are initially curved around the merlons 1054 of the castellated mandrel assembly 1038. The diameter of the castellated mandrel 1034 at the battlement-like structure 1048 may be varied, in order to control the diameter of the open portion

1518. The number and size of the merlons 1054 may be varied in order to control the number and size of the loops 1516. The loops 1516 may serve as a blunt leading portion as the mesh device 1500 is expanded within a vascular defect, increasing the safety of its use.

At the top (distal) end 1810 of a mesh device 1800 is illustrated in FIG. 63E which combines characteristics of the mesh device 1400 of FIG. 59 and the mesh device 1500 of FIG. 60. The mesh device 1800 is constructed using elements of both the process described in relation to FIGS. 63A and 63B, and the process described in relation to FIGS. 64A and 64B. A first subset of the filaments 1812a is braided with the process of FIGS. 63A and 63B, and forms a closed distal apex 1815. A second subset of the filaments 1812b is braided with the process of FIGS. 64A and 64B, and forms a plurality of loops 1816, each having an orifice 1893. Each of the subsets of filaments 1812a, 1812b are secured to the castellated mandrel assembly 1038 at the beginning of the braiding process in the manner described in relation to FIGS. 63A and 63B, and FIGS. 64A and 64B, respectively. The filaments 1812a cover what would otherwise be an open portion, but because they represent a smaller subset of the total number of filaments 1812, the central crossing point 1873 has fewer filaments 1812a that overlap, thus allowing a reduced distal profile (thickness) for ease of collapse and placement through a microcatheter. In some embodiments, there may be a total of 35 crossings of filaments 1812a at the central crossing point 1873, though the mesh device 1800 may incorporate about 76 or more filaments. In some embodiments, the ratio of the number of crossings at the central crossing point 1073 to the total number of filaments 1812 may range from about 3% to about 46%, or about 8% to about 19%. In some embodiments, the central crossing point 1873 may comprise multiple crossing points 1873a, 1873b, which may be achieved by performing the method of FIGS. 63A and 63B while extending the filaments 1812a between two or more pairs of crenels 1052 that are each less than 180° apart. The forming of multiple crossing points 1873a, 1873b, etc. may allow a reduced distal profile (thickness) for ease of collapse and placement through a microcatheter, or may create multiple closed areas at different portions of the closed distal apex 1815.

Figure 63F:
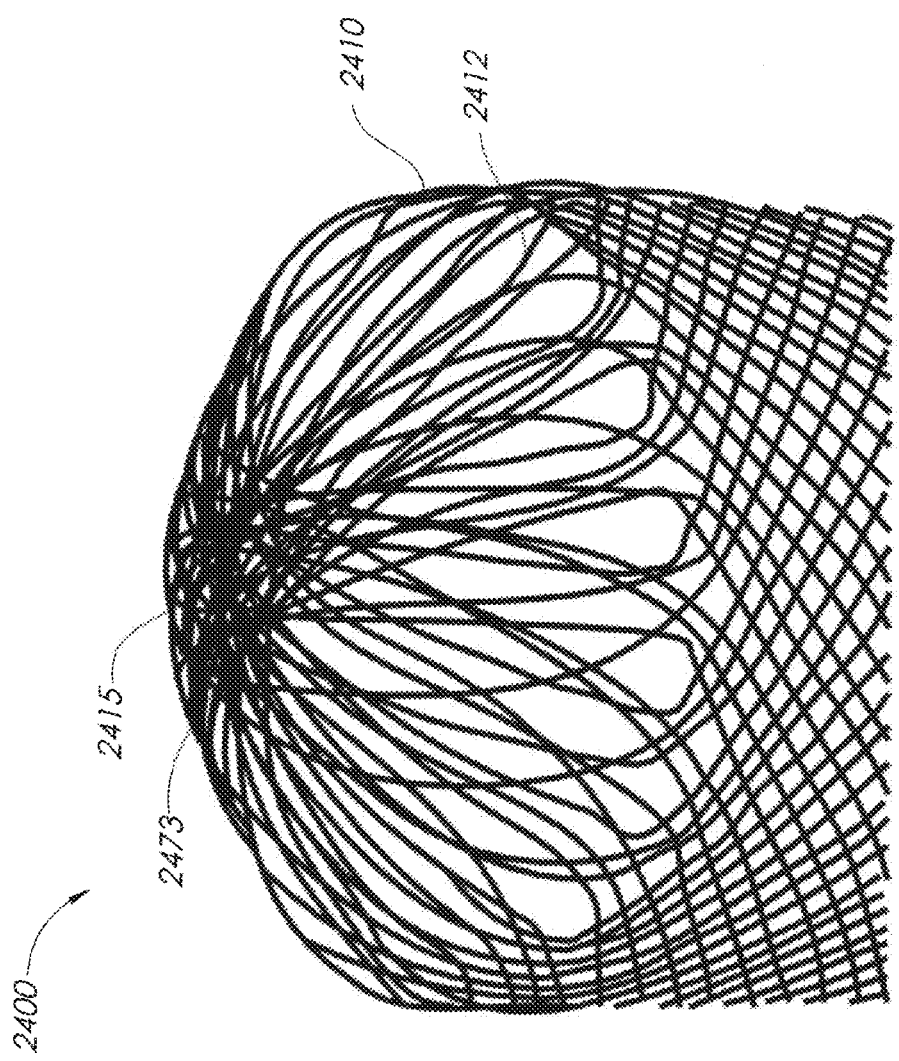
FIG. 63F is a perspective view an embodiment of a device for treatment of a patient's vasculature.

A top (distal) end 2410 of a mesh device 2400 is illustrated FIG. 63F. The mesh device 2400 is similar to the mesh device 1400 of FIG. 59 and may be constructed with the method described in relation to FIGS. 63A-63C, using the castellated mandrel assembly 1038 of FIGS. 61-62. Filaments 2412 are extended over the convex radius 1056 of the radiused cap 1044 to form a closed distal apex 2415 having a central crossing point 2473. In some embodiments, the mesh device 2400 may be constructed without using the variable braid density method of FIGS. 50A-54D, and in other embodiments, the mesh device 2400 may be constructed using the variable braid density method of FIGS. 50A-54D. The closed distal apex 2415 has no hub at the distal end 2410 holding the filaments 2412, and thus may be placed in a previously ruptured aneurysm with less risk of rerupture (repeated rupture at a healed or partially-healed rupture site), as there is only a smooth surface presented to the aneurysm dome. In addition, there would be less risk of rupture occurring at a new site.

Figure 63G:
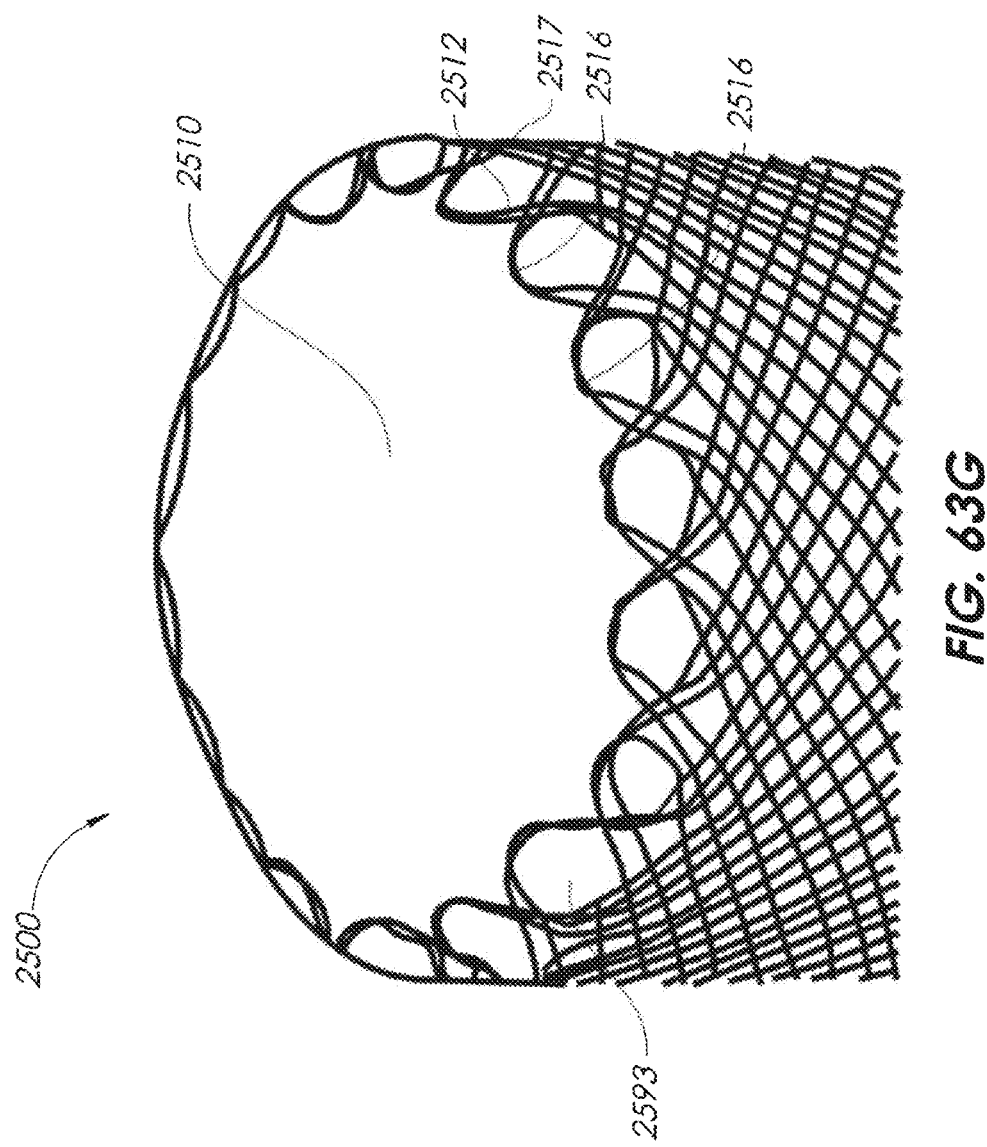
FIG. 63G is a perspective view an embodiment of a device for treatment of a patient's vasculature

A top (distal) end 2517 of a mesh device 2500 is illustrated in FIG. 63G. The mesh device 2500 is similar to the mesh device 1500 of FIG. 60 and may be constructed with the method described in relation to FIG. 63D, using the castellated mandrel assembly 1038 of FIGS. 61-62. Filaments 2512 are formed into loops 2516 having orifices 2593. On open portion 2510 is thus centrally located at the distal lend 2517 of the mesh device 2500. In some embodiments, the mesh device 2500 may be constructed without using the variable braid density method of FIGS. 50A-54D, and in other embodiments, the mesh device 2500 may be constructed using the variable braid density method of FIGS. 50A-54D. The open portion 2510 may be located in a ruptured aneurysm with less risk of rupture or rerupture, as there is no material contacting the aneurysm dome.

Figure 65:
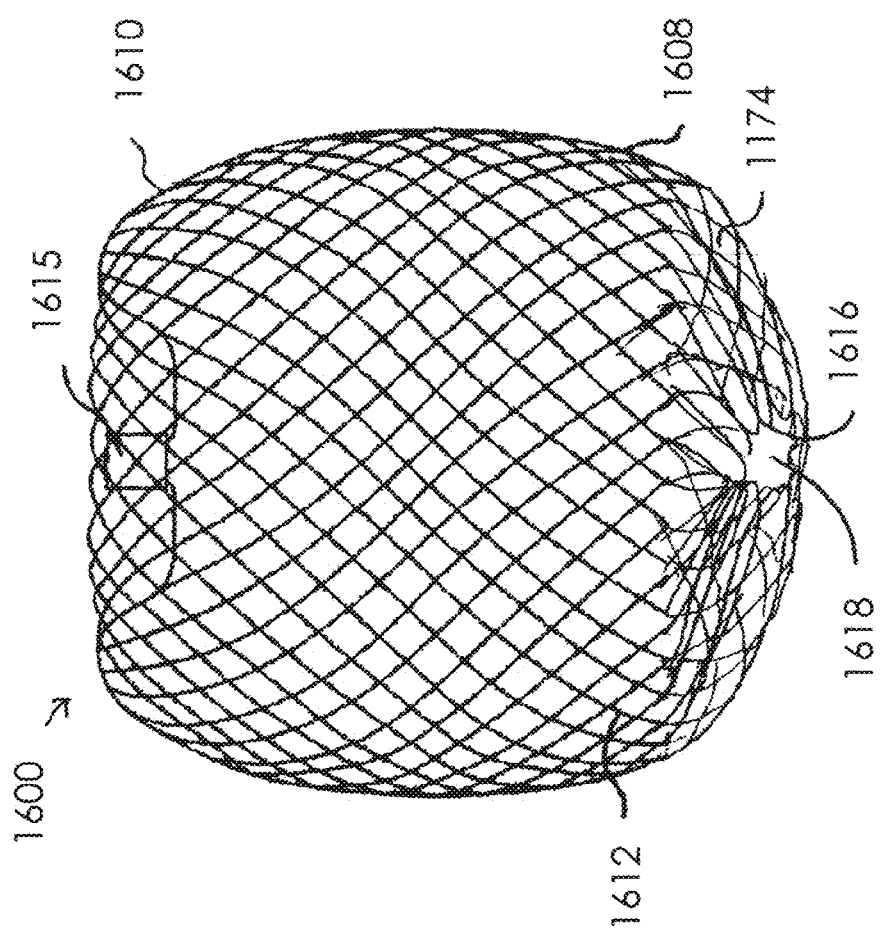
FIG. 65 is an elevation view of an embodiment of a device for treatment of a patient's vasculature.
Figure 66:
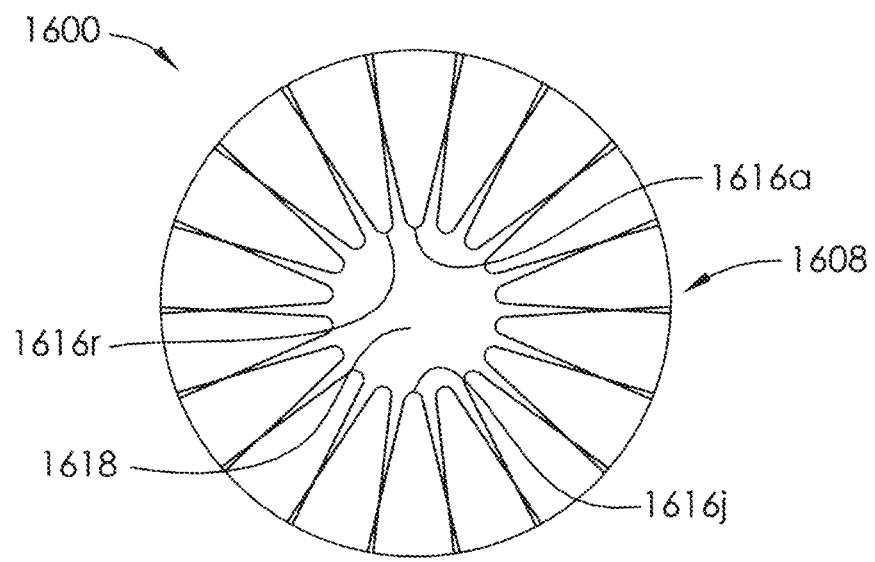
FIG. 66 illustrates a proximal end of the device of FIG. 65.

A mesh device 1600, illustrated in FIG. 65, is braided with filaments 1612 in a similar manner to the mesh device 1500 in FIG. 60. However, the distal end 1610 of the mesh device 1600, which has a marker band 1615 securing the filaments 1612, is more similar to the proximal end 1508 of the mesh device 1500 and the proximal end 1608 of the mesh device 1600 is braided in a similar manner (with a castellated mandrel assembly) to the distal end 1510 of the mesh device 1500. A relatively small castellated mandrel 1034 diameter at the battlement-like structure 1048 is used—or alternately the loading technique described in FIG. 63D—in order to create a small diameter open portion 1618. For example, a circular opening in the open portion 1618 of approximately 1 mm in diameter may be chosen. One purpose of the open portion 1618, is to allow the insertion of a microcatheter 1161 (FIGS. 67-71) after the mesh device 1600 has been deployed inside a vascular defect, for example an aneurysm. FIG. 66 illustrates loops 1616a-r-1616a, 1616j, and 1616r are labeled—arrayed circumferentially around the proximal end 1608 of the mesh device 1600, with the open portion 1618 in the center.

Figure 75:
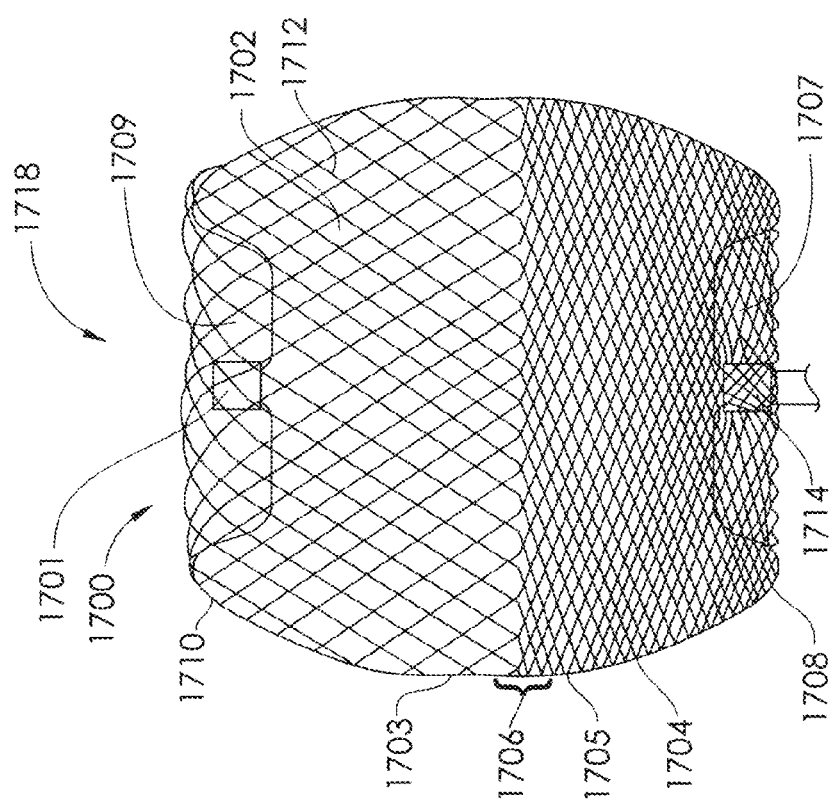
FIG. 75 is an elevation view of an embodiment of a device for treatment of a patient's vasculature.

A mesh device 1700 is illustrated in FIG. 75 in its expanded configuration. The mesh device 1700 comprises a single layer braided tubular member having a first braided portion 1702 having a first average braid density $BD_{avg1}$ and a second braided portion 1704 having a second average braid density $BD_{avg2}$. The second average braid density $BD_{avg2}$ is greater than the first average braid density $BD_{avg1}$. The braid density BD transitions from the first braided portion 1702 to the second braided portion 1704 over a transition zone TZ 1706. The braid density ranges and braid density ratios discussed in conjunction with the mesh device 1200 of FIG. 55 also apply here.

The mesh device 1700 has a proximal end 1708 and a distal end 1710, the first braided portion 1702 adjacent the distal end 1710 and the second braided portion 1704 adjacent the proximal end 1708. Individual filaments 1712 that constitute an alternative braided tubular member from which the mesh device 1700 is made are secured together at the proximal end 1708 by a marker band 1714, for example, a marker band comprising a radiopaque material such as platinum or a platinum alloy. Individual filaments 1712 that constitute an alternative braided tubular member from which the mesh device 1700 is made are also secured together at the distal end 1710 by a marker band 1701. Alternatively, the individual filaments 1712 may be held together by welding, adhesives, epoxies or any other joining method. The adhesive or epoxy may be doped with radiopaque material, such as tantalum, in order to increase visualization. In some embodiments, one or both of the marker bands 1714, 1701 are within a recessed portion 1707, 1709. The mesh device 1700, when used for the purpose of treating a vascular defect such as a cerebral aneurysm, is placed into the aneurysm so that the second braided portion 1704 covers the neck of the aneurysm. The second average braid density $BD_{avg2}$ of the second braided portion 1704 is above an average braid density $BD_{avg}$ that is in a range that effectively stagnates the flow of blood into the aneurysm when the mesh device 1700 is expanded within the aneurysm. In addition, the average hydraulic diameter $D_H$ of each of the diamond-shaped openings 1011 at the most expanded region 1705 of the second braided portion 1704 is 200 µm or less. The average hydraulic diameter $D_H$ of each of the diamond shaped openings 1011 at the most expanded region 1703 of the first braided portion 1702 may be greater than 300 µm, or even greater than 500 µm, with the mesh device 1700 retaining its mechanical characteristics, such as radial strength.

Figure 67:
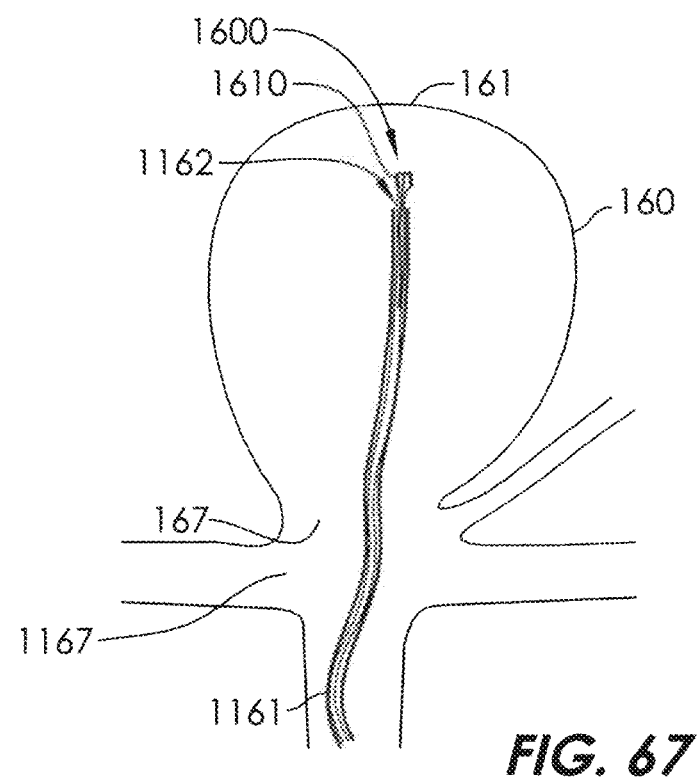
FIG. 67 is the embodiment of FIG. 65 being delivered into an aneurysm through a microcatheter.
Figure 68:
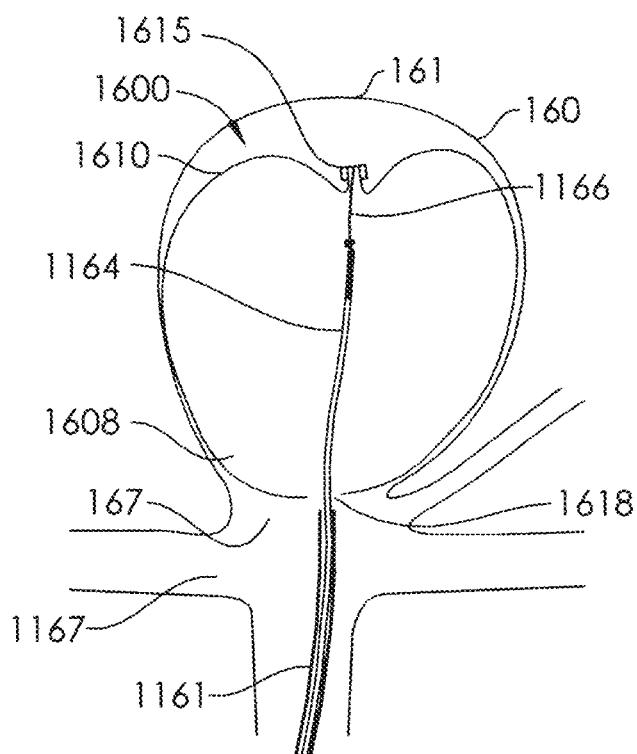
FIG. 68 is the embodiment of FIG. 65 immediately prior to detachment from a delivery apparatus.
Figure 69:
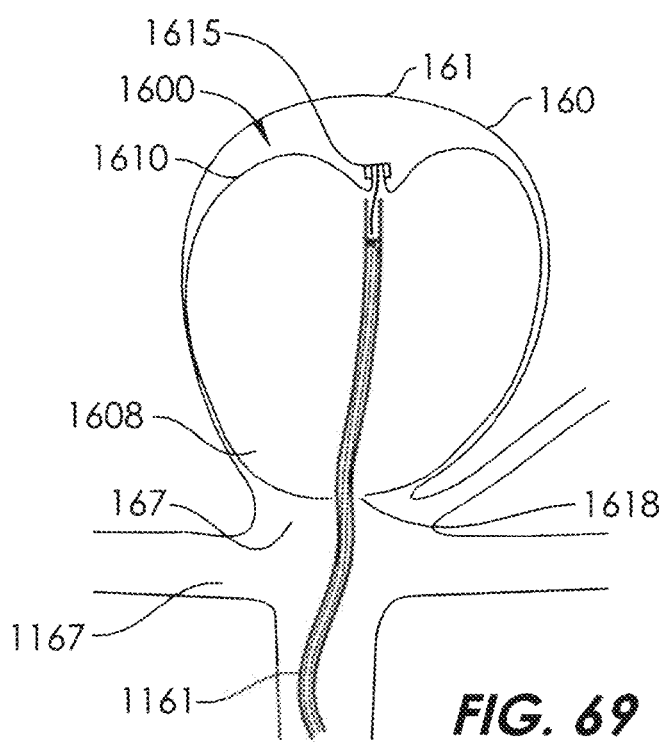
FIG. 69 is the embodiment of FIG. 65 following detachment from a delivery apparatus.
Figure 70:
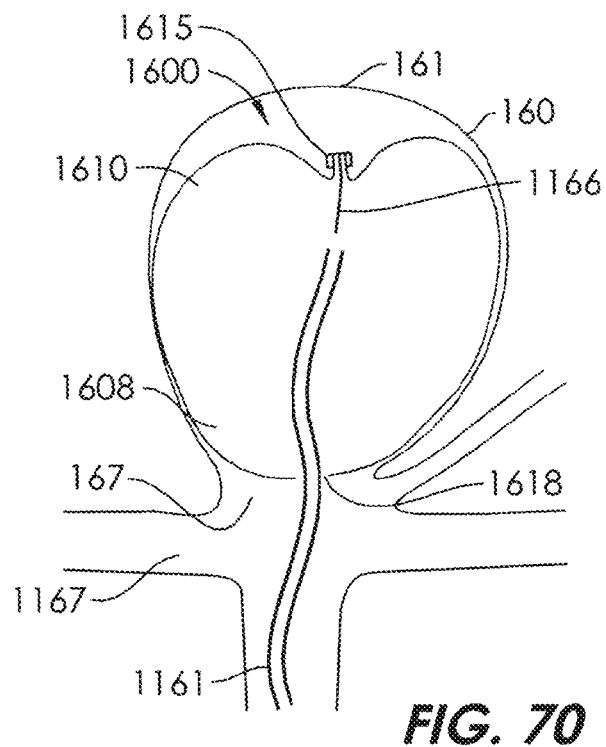
FIG. 70 is the embodiment of FIG. 65 during the repositioning of the microcatheter.
Figure 71:
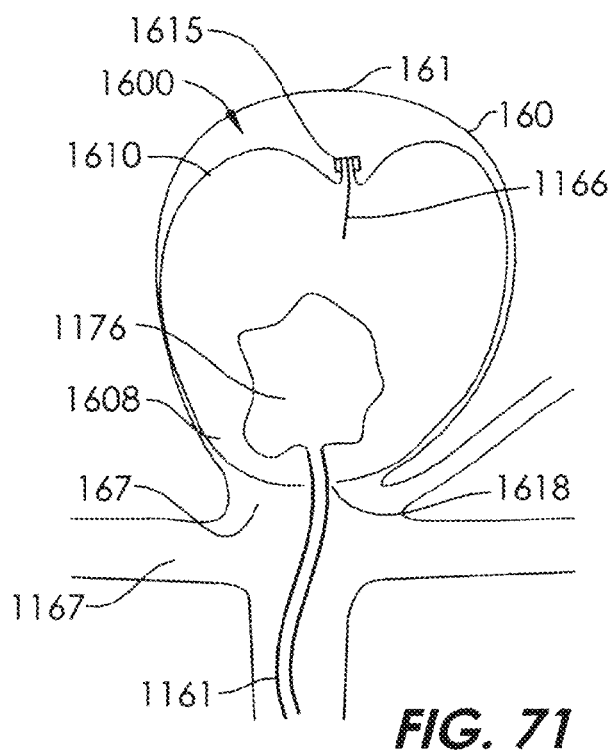
FIG. 71 is the embodiment of FIG. 65 during the delivery of an embolic material.

A method for embolizing a vascular defect, such as an aneurysm 160 with a neck 167 and a dome 161, with the mesh device 1600 and one or more adjunctive devices is illustrated in FIGS. 67-71. In FIG. 67 a microcatheter 1161 is navigated into the aneurysm 160 and the constrained mesh device 1600 is delivered through the lumen 1162 of the microcatheter 1161 until the distal end 1610 begins to exit the lumen 1162 of the microcatheter 1161. In FIG. 68, the microcatheter 1161 is carefully pulled back while maintaining a force on the proximal end of a delivery apparatus 1164, which is coupled to the mesh device 1600, thus allowing the mesh device 1600 to expand. The mesh device 1600 may be selected at a size slightly larger than the aneurysm 106 so that it is secure within the aneurysm 160 without causing any damage to the aneurysm 160. As shown in FIG. 69, the microcatheter 1161 is now tracked forward, through the open portion 1618 of the mesh device 1600 and over the delivery apparatus 1164. Detachment of the mesh device 1600 from the delivery apparatus 1164 is now performed, for example, using the embodiment described in conjunction with FIGS. 12-15, or alternatively, by embodiments described by Plaza et al. in U.S. Pat. No. 8,597,323, issued Dec. 3, 2013, titled "Delivery and Detachment Systems and Methods for Vascular Implants," incorporated herein by reference in its entirety. One difference is that the tether 1166 that is thermally severed is attached within the distal end 1610 of the mesh device 1600. After detachment, as illustrated in FIG. 70, the detached delivery apparatus 1164 is completely removed from the microcatheter 1161 and the microcatheter 1161 is carefully retracted to a more proximal location within the mesh device 1600. An adjunctive device is now used to further or complete the embolization of the aneurysm 160. For example, as in FIG. 71, an embolic material 1176 is injected through the lumen 1162 of the microcatheter 1161 to fill at least a proximal portion of the mesh device 1600. The mesh device 1600 thus serves as a constraint for keeping the embolic material 1176 contained, and stops it from embolizing into one or more of the native vessels, such as vessel 1167. The embolic material 1176 may serve to cover some of the openings 1174 (FIG. 65) at the proximal end 1608 of the mesh device 1600. The mesh device 1600 may also incorporate the variable braid density described in several of the prior embodiments, but this is not a required feature.

Figure 72:
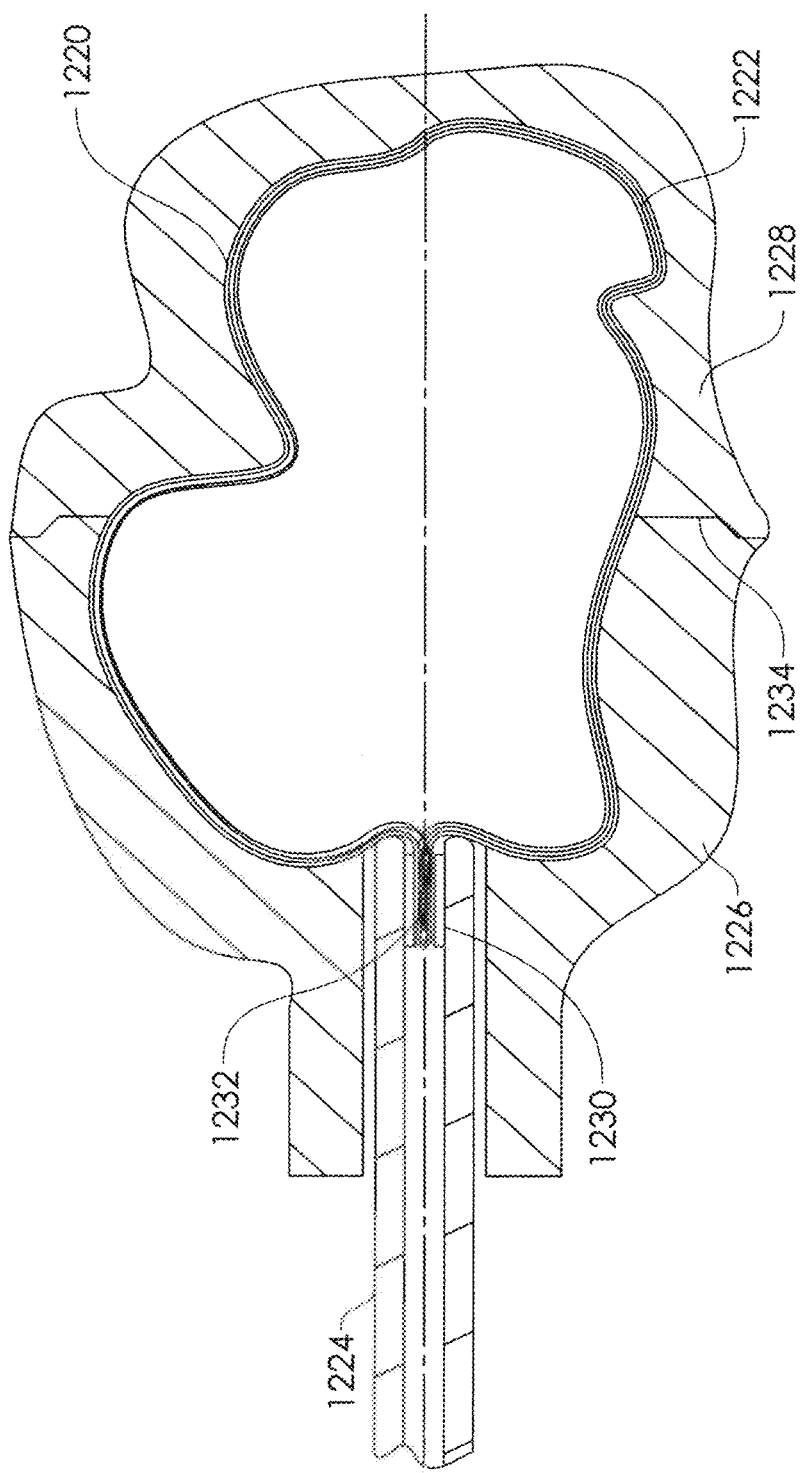
FIG. 72 illustrates tooling for forming a custom mesh device.
Figure 73:
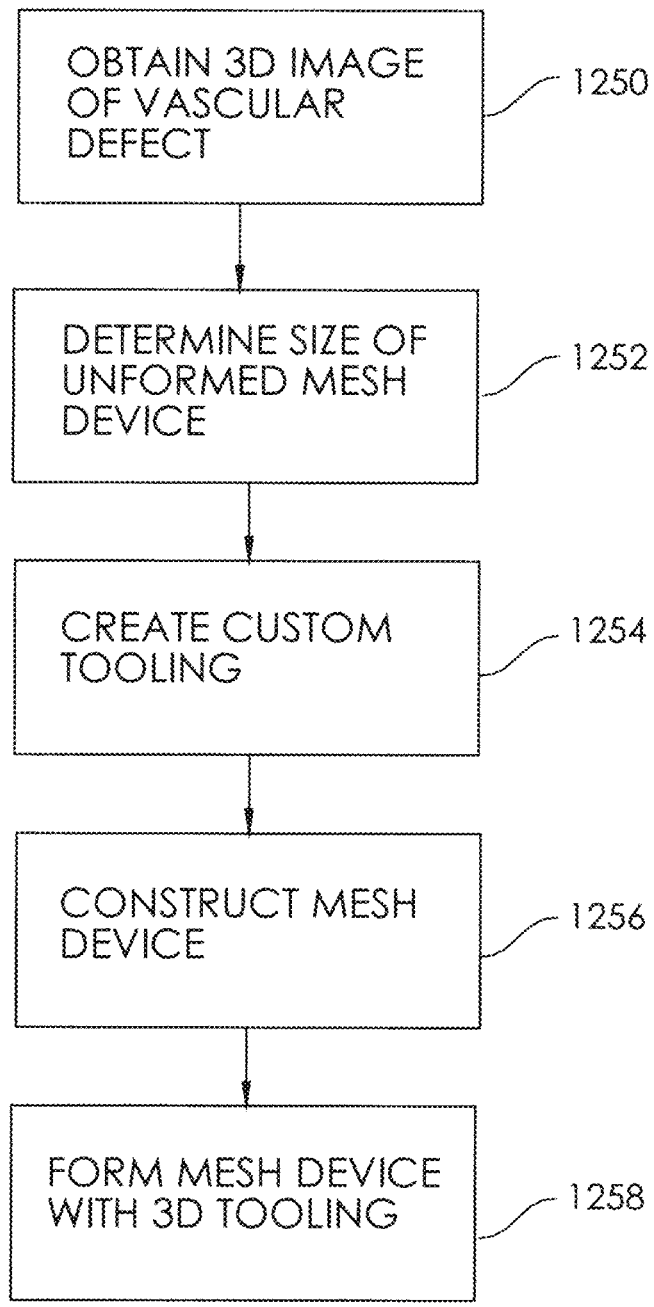
FIG. 73 is a method for forming a custom mesh device.

There are clinical cases in which a vascular defect is an odd non-uniform or non-symmetrical shape. FIGS. 72-73 illustrate an embodiment of a custom-shaped mesh device and a method for producing it. In step 1250, a three-dimensional image is obtained of a vascular defect, for example, a CT scan of an MRI. In step 1252 the size of an appropriate unformed mesh device 1220 to fit the vascular defect is determined by using information from the three-dimensional image. This includes the filament material, the filament transverse dimension(s), the number of filaments, the length of the braided tubular member 1000 to form the mesh device 1220, the length of the mesh device 1220, the diameter of the mesh device 1220 and the braiding method to form the mesh device 1220. This includes the number of over and under filaments, the density of the braid, the size of the braiding machine (i.e., disc diameter), and the weight of the follower weight and the tensioning members. In step 1254, custom tooling, comprising a first forming tool 1226 and a second forming tool 1228 are created. The three-dimensional image is used to create a three-dimensional computer model of the tooling. Parting line alignment 1234 of the tooling is chosen so that the two forming tools 1226, 1228 will be able to go together, and will be able to separate. Rapid prototyping processes are used to create the forming tools 1226, 1228 from high temperature materials, such as 3D printing, stereolithography, casting from stereolithography forms, etc. In step 1256, the mesh device 1220 is braided from filaments 1222, with filament ends 1232 secured within a marker band 1230. In step 1258 an end forming mandrel 1224 and the two forming tools 1226, 1228 are used to form the shape in the mesh device 1220 by forcing the mesh device 1220 inside each of the forming tools 1226, 1228 and exposing the mesh device 1220 to an elevated temperature, and subsequently cooling the mesh device. The end forming mandrel 1224 and the forming tools 1226, 1228 are then removed, leaving a mesh device 1220 that has a custom shape, configured to fit within the non-uniform vascular defect. For example, a mesh device 1220 formed from nitinol filaments may be formed at a temperature of around 500° C.

Figure 74:
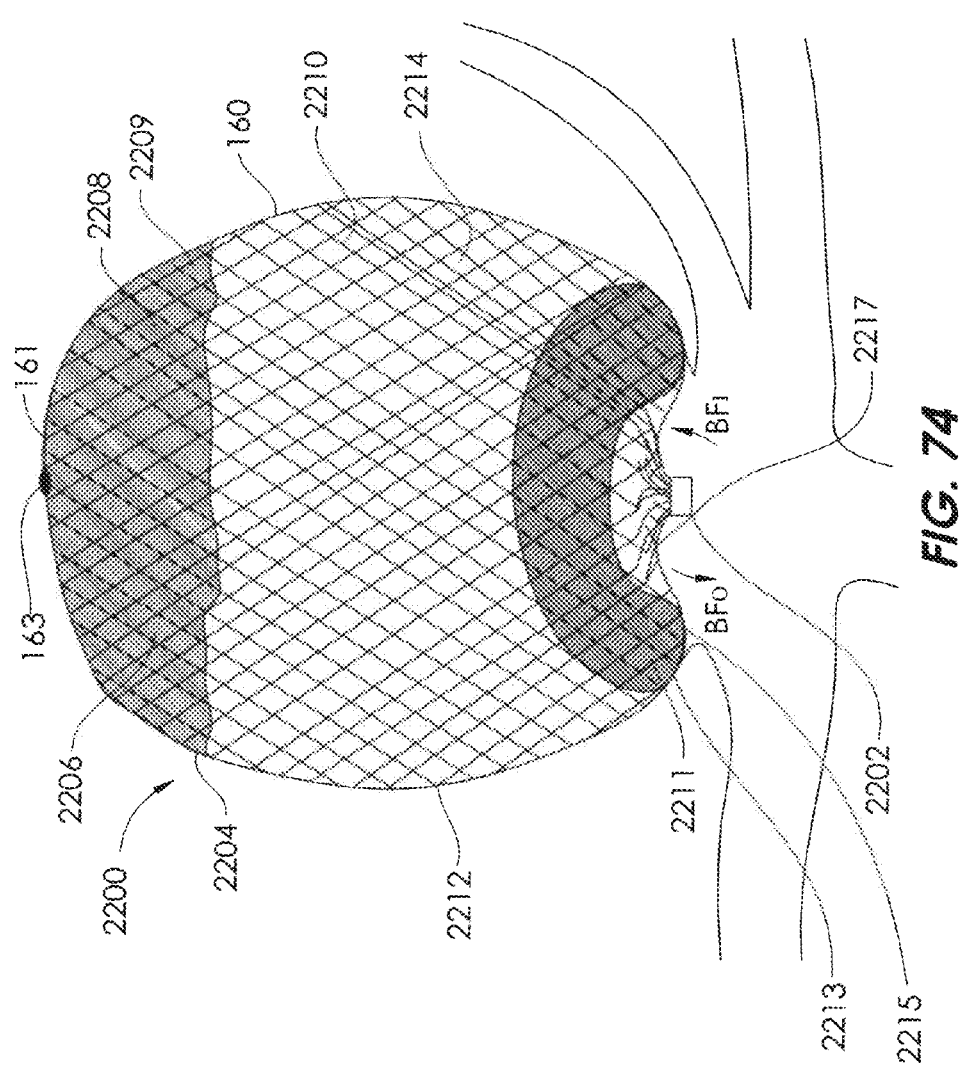
FIG. 74 is an embodiment of a mesh device for treatment of a patient's vasculature deployed within an aneurysm.

FIG. 74 illustrates a mesh device 2200 implanted within a vascular defect 160 (aneurysm) having a healed (or fresh, unhealed) rupture site 163 at its dome 161. In some embodiments the mesh device 2200 has a proximal hub 2202 but no distal hub. In some embodiments, the distal portion 2204 of the mesh device 2200 contains a first flexible filler material section 2206 between openings 2208 in the filaments 2210. The flexible filler material section 2206 comprises a flexible filler material 2209. In some embodiments, the flexible filler material 2209 may comprise silicone or polyurethane dip material. As seen in FIG. 74, in use, the distal portion 2204 of the mesh device 2200 having the flexible filler material section 2206 is placed adjacent the rupture site 163. As implanted in FIG. 74, the mesh device 2200 can protect rupture site 163, either aiding closure of the rupture site 163 or guarding against re-rupture. At the same time, in some embodiments, the proximal portion 2212, may comprise no flexible filler material section 2206 covering its openings 2214, and thus allows for some initial blood flow $B_{FI}$ into the aneurysm 160 and blood flow $B_{FO}$ out of the aneurysm 160, until the aneurysm 160 progresses through the occlusion process. In other embodiments, the proximal portion 2212 may include a second flexible filler material section 2211. In some embodiments, the second flexible filler material section 2211 may comprise the same flexible filler material 2209 as the first flexible filler material section 2206. In some embodiments, the second flexible filler material section 2211 may have a ring shape, such that an outer ring portion 2213 seats against the wall of the aneurysm 160, and an inner ring portion 2215 impedes at least some of the blood flow $B_{FI}$ into the aneurysm 160 and blood flow Br out of the aneurysm 160. An open section 2217, which has no filler material, may be included in a central portion, where the openings 2214 have relatively smaller sizes, and thus impede at least some flow into and/or out of the aneurysm 160.

Whether depicted or not, all of the embodiments of mesh devices depicted may incorporated a variable braid density. This includes mesh devices having two or more layers. For example, an inner structure of filamentary members may have a braided structure having at least two distinct portions, each with a different braid density, and an outer structure of filamentary members may have a less variable or non-variable braid density. Alternatively, an outer structure of filamentary members may have a braided structure having at least two distinct portions, each with a different braid density, and an inner structure of filamentary members may have a less variable or non-variable braid density. Yet still, both outer and inner structures may each have distinct portions variable braid densities. Also, in any of the embodiments, it is possible to include bioresorbable filaments, for example, filaments comprising (PGLA), (PGA), or (PLLA). In some embodiments, an outer shell of braided PGLA filaments surrounds an inner shell of nitinol or DFT filaments. The outer shell may be dissolvable in order to detach the mesh device. It is even possible to make a fully bioresorbable mesh device. Bioresorbable metals such as magnesium, magnesium alloys, iron, or iron alloy may also be used to make bioresorbable filaments. In any of the embodiments, it is possible to coat at least some of the permeable shell or filaments with a growth factor, for example a CE34 antibody, in order to encourage the growth of endothelial cells, to form a healing cap on an occluded aneurysm. The action of the CE34 antibody is to bind to an endothelial-derived growth factor.

In one embodiment, a device for treatment of an aneurysm a patient's vasculature is provided having a self-expanding resilient permeable shell having a proximal end, a distal end, and a longitudinal axis, the shell having a plurality of elongate resilient filaments having a variable braided structure, wherein the plurality of filaments are secured at at least one of the proximal end or the distal end thereof; wherein the permeable shell has a radially constrained elongated state configured for delivery within a microcatheter and an expanded relaxed state with a globular, axially shortened configuration relative to the radially constrained state, the permeable shell having a plurality of openings formed between the braided filaments; wherein the variable braided structure includes: a first braided portion adjacent the distal end and having a first braid density; a second braided portion adjacent the proximal end and having a second braid density, the second braid density being greater than the first braid density; and wherein the plurality of filaments span the first braided portion and the second braided portion in a continuous single layer. In some embodiments, the filaments have a transverse dimension of between 0.0005" and 0.002". In some embodiments the second braid density is in the range of about 1.25 to about 5.0 times the first braid density. In some embodiments, the second braid density is in the range of about 1.25 to about 2.5 times the first braid density. In some embodiments, the second braid density is in the range of about 1.50 to about 2.0 times the first braid density. In some embodiments, the second braid density is between about 0.15 and about 0.40. In some embodiments, the second braid density is between about 0.17 and about 0.30. In some embodiments, the first braid density is between about 0.10 and about 0.20. In some embodiments, the first braid density is between about 0.10 and about 0.15. In some embodiments, the second braided portion includes a plurality of openings, each opening having a hydraulic diameter, wherein the average hydraulic diameter of the plurality of openings in the second braided portion is 200 µm or less. In some embodiments, the first braided portion includes a plurality of openings, each opening having a hydraulic diameter, wherein the average hydraulic diameter of the plurality of openings in the first braided portion is greater than 200 µm. In some embodiments, the average hydraulic diameter of the plurality of openings in the first braided portion is greater than 300 µm. In some embodiments, the plurality of filaments includes filaments of at least two different transverse dimensions. In some embodiments, the plurality of filaments includes structural filaments, each having a first end, a second end, and a central section, and wherein the central section is curved back upon itself, and wherein the first and second ends are secured at the proximal end of the permeable shell. In some embodiments, the distal end of the permeable shell includes a plurality of loops formed from single filaments. In some embodiments, the proximal end of the permeable shell includes a plurality of loops formed from single filaments. In some embodiments, the distal end of the permeable shell includes a plurality of unsecured filament ends. In some embodiments, the plurality of unsecured filaments ends includes a plurality of ends having protective covers. In some embodiments, the device further includes a permeable layer having a proximal end, a distal end, and a longitudinal axis, the permeable layer including a plurality of elongate resilient filaments having a braided structure, the permeable layer disposed inside or outside of the permeable shell. In some embodiments, at least a portion of the permeable shell is coated with a growth factor. In some embodiments, the growth factor is a CE34 antibody. In some embodiments, at least some of the filaments include bioresorbable filaments. In some embodiments, the bioresorbable filaments include at least one of PGLA, PGA, and PLLA filaments.

In another embodiment, a device for treatment of an aneurysm a patient's vasculature is provided having a self-expanding resilient permeable shell having a proximal end, a distal end, and a longitudinal axis, the shell including a plurality of elongate resilient filaments having a braided structure, wherein the plurality of filaments are secured at at least one of the proximal end or the distal end thereof; wherein the permeable shell has a radially constrained elongated state configured for delivery within a microcatheter; wherein the permeable shell has an expanded relaxed state with a globular, axially shortened configuration relative to the radially constrained state, the permeable shell having a plurality of openings formed between the braided filaments; and wherein the plurality of filaments includes structural filaments, each having a first end, and second end, and a central section, and wherein the central section is curved back upon itself, and wherein the first end and second end are secured at the proximal end of the permeable shell. In some embodiments, the plurality of filaments includes filaments of at least two different transverse dimensions. In some embodiments, at least some of the filaments include platinum. In some embodiments, the distal end of the permeable shell includes a plurality of loops formed from single filaments. In some embodiments, the proximal end of the permeable shell includes a plurality of loops formed from single filaments. In some embodiments, the distal end of the permeable shell includes a plurality of unsecured filament ends. In some embodiments, the plurality of unsecured filaments ends includes a plurality of ends having protective covers. In some embodiments, the device further includes a permeable layer having a proximal end, a distal end, and a longitudinal axis, the permeable layer including a plurality of elongate resilient filaments having a braided structure, the permeable layer disposed inside or outside of the permeable shell. In some embodiments, at least a portion of the permeable shell is coated with a growth factor. In some embodiments, the growth factor is a CE34 antibody In some embodiments, at least some of the filaments include bioresorbable filaments. In some embodiments, the bioresorbable filaments include at least one of PGLA, PGA, and PLLA filaments. In some embodiments, the distal end of the permeable shell includes a closed structure.

In another embodiment, a device for treatment of an aneurysm a patient's vasculature is provided having a self-expanding resilient permeable shell having a proximal end, a distal end, and a longitudinal axis, the shell including a plurality of elongate resilient filaments having a braided structure, wherein the plurality of filaments are secured at at least one of the proximal end or the distal end thereof; wherein the permeable shell has a radially constrained elongated state configured for delivery within a microcatheter; wherein the permeable shell has an expanded relaxed state with a globular, axially shortened configuration relative to the radially constrained state, the permeable shell having a plurality of openings formed between the braided filaments; and wherein the plurality of filaments includes structural filaments, each having a first end, and second end, and a central section, and wherein the central section is curved back upon itself, and wherein the first end and second end are secured at the distal end of the permeable shell. In some embodiments, the plurality of filaments includes filaments of at least two different transverse dimensions. In some embodiments, at least some of the filaments include platinum. In some embodiments, the distal end of the permeable shell includes a plurality of loops formed from single filaments. In some embodiments, the proximal end of the permeable shell includes a plurality of loops formed from single filaments. In some embodiments, the device further includes a permeable layer having a proximal end, a distal end, and a longitudinal axis, the permeable layer including a plurality of elongate resilient filaments having a braided structure, the permeable layer disposed inside or outside of the permeable shell. In some embodiments, at least a portion of the permeable shell is coated with a growth factor. In some embodiments, the growth factor is a CE34 antibody. In some embodiments, at least some of the filaments include bioresorbable filaments. In some embodiments, the bioresorbable filaments include at least one of PGLA, PGA, and PLLA filaments. In some embodiments, the device further includes an opening at the proximal end. In some embodiments, the opening has a diameter of at least one millimeter. In some embodiments, the opening if configured to allow the passage of a microcatheter. In some embodiments, at least a portion of the permeable shell is configured to contain an embolic material.

In another embodiment, a device for treatment of an aneurysm a patient's vasculature is provided having a self-expanding resilient permeable shell having a proximal end, a distal end, and a longitudinal axis, the shell including a plurality of elongate resilient filaments having a variable braided structure, wherein the plurality of filaments are secured at at least one of the proximal end or the distal end thereof; wherein the permeable shell has a radially constrained elongated state configured for delivery within a microcatheter; wherein the permeable shell has an expanded state with a globular, axially shortened configuration relative to the radially constrained state, the permeable shell having a plurality of openings formed between the braided filaments; wherein the variable braided structure includes: a first braided portion adjacent the distal end and having a first braid density; a second braided portion adjacent the proximal end and having a second braid density greater than the first braid density; wherein the plurality of filaments span the first braided portion and the second braided portion in a continuous single layer; and wherein a majority of the plurality of openings formed between the braided filaments in the second braided portion have a diameter of between about 0.005 inches and about 0.01 inches. In some embodiments, a majority of the plurality of openings formed between the braided filaments in the second braided portion have a diameter of between about 0.006 inches and about 0.009 inches. In some embodiments, a majority of the plurality of openings formed between the braided filaments in the second braided portion have a diameter of between about 0.007 inches and about 0.008 inches.

In another embodiment, a device for treatment of an aneurysm a patient's vasculature is provided having a first self-expanding resilient permeable shell having a proximal end, a distal end, and a longitudinal axis, the first permeable shell including a plurality of elongate resilient filaments having a braided structure, wherein the plurality of filaments are secured at at least the proximal end thereof; wherein the first permeable shell has a radially constrained elongated state configured for delivery within a microcatheter; wherein the first permeable shell has an expanded state with an axially shortened configuration relative to the radially constrained state, the first permeable shell having a plurality of openings formed between the braided filaments; a second self-expanding resilient permeable shell having a proximal end, a distal end, and a longitudinal axis, the second permeable shell including a plurality of elongate resilient filaments having a braided structure, wherein the plurality of filaments are secured at at least the distal end thereof; wherein the second permeable shell has a radially constrained elongated state configured for delivery within a microcatheter; wherein the second permeable shell has an expanded state with an axially shortened configuration relative to the radially constrained state, the second permeable shell having a plurality of openings formed between the braided filaments; wherein braided structure of the first permeable shell has a first braid density and the braided structure of the second permeable shell has a second braid density, greater than the first braid density; and wherein the proximal end of the plurality of filaments of the first permeable shell are secured to the distal end of the plurality of filaments of the second permeable shell. In some embodiments, the proximal end of the plurality of filaments of the first permeable shell and the distal end of the plurality of filaments of the second permeable shell are each secured to a band. In some embodiments, the device further includes a third self-expanding resilient permeable shell having a proximal end, a distal end, and a longitudinal axis, the third permeable shell including a plurality of elongate resilient filaments having a braided structure, wherein the plurality of filaments are secured at at least the proximal end thereof; wherein the third permeable shell has a radially constrained elongated state configured for delivery within a microcatheter; wherein the third permeable shell has an expanded state with an axially shortened configuration relative to the radially constrained state, the third permeable shell having a plurality of openings formed between the braided filaments; wherein braided structure of the third permeable shell has a third braid density, greater than the first braid density; and wherein the distal end of the plurality of filaments of the first permeable shell are secured to the proximal end of the plurality of filaments of the third permeable shell. In some embodiments, the third braid density is different from the second braid density.

In another embodiment, a device for treatment of an aneurysm a patient's vasculature is provided having a self-expanding resilient permeable shell having a proximal end, a distal end, and a longitudinal axis, the shell including a plurality of elongate resilient filaments having a variable braided structure, wherein the plurality of filaments are secured at at least one of the proximal end or the distal end thereof; wherein the permeable shell has a radially constrained elongated state configured for delivery within a microcatheter and an expanded relaxed state with a globular, axially shortened configuration relative to the radially constrained state, the permeable shell having a plurality of openings formed between the braided filaments; wherein the variable braided structure includes a first braided portion adjacent the distal end and having a first porosity P1; a second braided portion adjacent the proximal end and having a second porosity P2, the first porosity P1 being greater than the second porosity P2; and wherein the plurality of filaments span the first braided portion and the second braided portion in a continuous single layer.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed:

1. A device for treating a cerebral aneurysm, comprising:
   an implant comprising a single layer of woven braided mesh, the implant having a proximal end with a hub, a distal end, and a longitudinal axis extending from the proximal end to the distal end, and a length;
   the implant having a distal region having a plurality of pores having an average diameter, a proximal region having a plurality of pores having an average diameter, and a transition region that lies substantially perpendicular to the longitudinal axis of the implant and extends between the distal and proximal regions and has a length;
   the implant having an expanded globular configuration when deployed, the expanded implant having a region of maximum diameter that extends from a proximal portion of the distal region through the transition region and to a distal portion of the proximal region,
   wherein the average diameter of the plurality of pores in the distal region is greater than the average diameter of the plurality of pores in the proximal region, and wherein the length of the transition region is about 0.5% to about 20% of the length of the implant.

2. The device of claim 1, wherein the average diameter of the plurality of pores in the distal region is greater than 250 μm.

3. The device of claim 1, wherein the average diameter of the plurality of pores in the distal region is greater than 400 μm.

4. The device of claim 1, wherein the average diameter of the plurality of pores in the distal region is between about 250 μm to about 500 μm or between about 300 μm to about 600 μm.

5. The device of claim 1, wherein the average diameter of the plurality of pores in the proximal region is 200 μm or less.

6. The device of claim 1, wherein the average diameter of the plurality of pores in the proximal region is between about 50 μm to about 200 μm.

7. The device of claim 1, wherein the average diameter of the plurality of pores in the proximal region is between about 100 μm to about 200 μm.

8. The device of claim 1, wherein the length of the transition region is about 1% to about 15% of the length of the implant.

9. The device of claim 1, wherein the length of the transition region is about 1% to about 10% of the length of the implant.

10. The device of claim 1, wherein the length of the transition region is about 3% to about 8% of the length of the implant.

11. A method for treating a cerebral aneurysm, comprising the steps of:
    providing an implant comprising a single layer of woven braided mesh, the implant having a proximal end with a hub, a distal end, and a longitudinal axis extending from the proximal end to the distal end, and a length,
    wherein the implant has a distal region having a plurality of pore having an average diameter, a proximal region having a plurality of pore having an average diameter, and a transition region that lies substantially perpendicular to the longitudinal axis of the implant and extends between the distal and proximal regions and has a length;
    wherein the implant has an expanded globular configuration when deployed, the expanded implant having a region of maximum diameter that extends from a proximal portion of the distal region through the transition region and to a distal portion of the proximal region,
    wherein the average diameter of the plurality of pores in the distal region is greater than the average diameter of the plurality of pores in the proximal region, and wherein the length of the transition zone may be about 0.5% to about 20% of the length of the implant;
    advancing the implant in the low profile radially constrained state within a microcatheter to a region of interest within a cerebral artery;
    deploying the implant within the cerebral aneurysm, wherein the distal and proximal permeable shells expand to their expanded shapes; and
    withdrawing the microcatheter from the region of interest after deploying the implant.

12. The method of claim 11, wherein the average diameter of the plurality of pores in the distal region is greater than 250 μm.

13. The method of claim 11, wherein the average diameter of the plurality of pores in the distal region is greater than 400 μm.

14. The method of claim 11, wherein the average diameter of the plurality of pores in the distal region is between about 250 μm to about 500 μm or between about 300 μm to about 600 μm.

15. The method of claim 11, wherein the average diameter of the plurality of pores in the proximal region is 200 μm or less.

16. The method of claim 11, wherein the average diameter of the plurality of pores in the proximal region is between about 50 μm to about 200 μm.

17. The method of claim 11, wherein the average diameter of the plurality of pores in the proximal region is between about 100 μm to about 200 μm.

18. The method of claim 11, wherein the length of the transition region is about 1% to about 15% of the length of the implant.

19. The method of claim 11, wherein the length of the transition region is about 1% to about 10% of the length of the implant.

20. The method of claim 11, wherein the length of the transition region is about 3% to about 8% of the length of the implant.

* * * * *